(12) United States Patent
Kristiansen et al.

(10) Patent No.: US 10,729,714 B2
(45) Date of Patent: Aug. 4, 2020

(54) BASIDIOMYCETE-DERIVED CREAM FOR TREATMENT OF SKIN DISEASES

(71) Applicant: Glycanova AS, Fredrikstad (NO)

(72) Inventors: Bjørn Kristiansen, Fredrikstad (NO); Anne Torill Hovland, Borgenhaugen (NO)

(73) Assignee: GLYCANOVA AS, Gamle Frederikstad (NO)

( * ) Notice: Subject to any disclaimer, the term of this patent is extended or adjusted under 35 U.S.C. 154(b) by 358 days.

(21) Appl. No.: 14/766,811

(22) PCT Filed: Feb. 10, 2014

(86) PCT No.: PCT/IB2014/058878
§ 371 (c)(1),
(2) Date: Aug. 10, 2015

(87) PCT Pub. No.: WO2014/122627
PCT Pub. Date: Aug. 14, 2014

(65) Prior Publication Data
US 2016/0015734 A1 Jan. 21, 2016

Related U.S. Application Data

(60) Provisional application No. 61/763,014, filed on Feb. 11, 2013.

(30) Foreign Application Priority Data

Feb. 11, 2013 (DK) .................................. 2013 70070

(51) Int. Cl.
| | |
|---|---|
| *A61K 8/99* | (2017.01) |
| *A61K 31/716* | (2006.01) |
| *A61K 36/07* | (2006.01) |
| *A61K 31/728* | (2006.01) |
| *A61K 9/00* | (2006.01) |
| *A61K 9/06* | (2006.01) |
| *A61K 35/644* | (2015.01) |
| *A61K 47/06* | (2006.01) |
| *A61K 47/10* | (2017.01) |
| *A61K 47/12* | (2006.01) |
| *A61K 47/26* | (2006.01) |
| *A61K 47/44* | (2017.01) |
| *A61K 9/70* | (2006.01) |

(52) U.S. Cl.
CPC .......... *A61K 31/716* (2013.01); *A61K 9/0014* (2013.01); *A61K 9/06* (2013.01); *A61K 31/728* (2013.01); *A61K 35/644* (2013.01); *A61K 36/07* (2013.01); *A61K 47/06* (2013.01); *A61K 47/10* (2013.01); *A61K 47/12* (2013.01); *A61K 47/26* (2013.01); *A61K 47/44* (2013.01); *A61K 9/0021* (2013.01); *A61K 9/7023* (2013.01)

(58) Field of Classification Search
None
See application file for complete search history.

(56) References Cited

U.S. PATENT DOCUMENTS

| | | |
|---|---|---|
| 5,997,875 A | 12/1999 | Zhou et al. |
| 7,514,085 B2 | 4/2009 | Kristiansen |
| 7,682,615 B2 | 3/2010 | Kristiansen |
| 7,947,283 B2 | 5/2011 | Tu et al. |
| 8,758,768 B2 | 6/2014 | Kristiansen |
| 9,072,776 B2 | 7/2015 | Kristiansen |
| 9,249,438 B2 | 2/2016 | Kristiansen |
| 10,471,135 B2 | 11/2019 | Kristiansen |
| 2008/0160043 A1 | 7/2008 | Kim et al. |
| 2017/0304415 A1 | 10/2017 | Kristiansen |

FOREIGN PATENT DOCUMENTS

| | | | |
|---|---|---|---|
| JP | 60-188402 | | 9/1985 |
| JP | 2006241130 | | 9/2006 |
| KR | 20090002678 A | * | 1/2009 |
| KR | 20100066694 A | * | 6/2010 |

OTHER PUBLICATIONS

Chen et al., "Effects of Ganoderma lucidum and it combined with Radix Salviae Miltiorrhizae, Radix Bupleuri, and Fructus Schisandrae Chinensis respectively on experimental hepatic injuries in mouse", Acta Academiae Medicinae Militaris Tertiae, May 2001, vol. 23, No. 5, pp. 567-570. (Including Assisted human translation).
Kagaku to Seibutsu, 1985, vol. 23, No. 12, pp. 797-802. (Including English translation of relevant part).
Mizuno et al., "Fractionation, Structural Features and Antitumor Activity of Water-Soluble Polysaccharide from "Reishi" the Fruit Body of Ganoderma lucidum", Nippon Nogeikagaku Kaishi, 1984, vol. 58, No. 9, pp. 871-880. (English abstract including English translation of relevant part of article provided).
Mizuno et al., "Fractionation, Chemical Modification and Antitumor Activity of Water-Insoluble Polysaccharides of the Fruiting Body of Ganoderma lucidum", Nippon Nogeikagaku Kaishi, 1985, vol. 59, No. 11, pp. 1143-1151. (English abstract including English translation of relevant part of article provided).
Mizuno et al., "Reishi, Ganoderma lucidum and Ganoderma tsugae: Bioactive Substances and Medicinal Effects", Food Reviews International, 1995, vol. 11, No. 1, pp. 151-166.
Rop et al., "Beta-glucans in higher fungi and their health effects", Nutrition Reviews, 2009, vol. 67, No. 11, pp. 624-631.
Zhou et al., "Ganodermataceae: Natural products and their related pharmacological functions", The American Journal of Chinese Medicine, 2007, vol. 35, No. 4, pp. 559-574.

* cited by examiner

*Primary Examiner* — Amy L Clark
(74) *Attorney, Agent, or Firm* — Merchant & Gould P.C.

(57) ABSTRACT

An extract of a liquid culture of *Ganoderma lucidum* is provided. The production process encourages the growing mycelium to export bioactive compounds such as beta glucans into the surrounding liquid. Thus, the beta glucan is soluble and easily absorbed. More importantly, the production process allows the beta glucan to retain its triple helix structure which is required to maintain a very high bioactive efficacy. The beta glucans from *Ganoderma lucidum* can be used in a cream for treatment of psoriasis.

17 Claims, 25 Drawing Sheets

A

B

A: Skin on human leg before treatment

B: Skin on same human leg after treatment

A) Patient BH: Right elbow pre and post treatment

B) Patient BH: Left elbow pre and post treatment

C) Patient RA: Right elbow pre and post treatment

D) Patient RA: Left elbow pre and post treatment

E) Patient RA: Right knee pre and post treatment

F) Patient RA: Left knee pre and post treatment

G) Patient JM: Right elbow pre and post treatment

H) Patient JM: Left elbow pre and post treatment

I) Patient JM: Right elbow pre and 1 month post treatment

J) Patient JM: Left elbow pre and 1 month post treatment

K) Patient JM: Right calf pre and post treatment

L) Patient PI: Right elbow pre and post treatment

M) Patient PI: Left elbow pre and post treatment

N) Patient JS: Right elbow pre and post treatment

O) Patient JS: Left elbow pre and post treatment

P) Patient NM: Right elbow pre and post treatment

Q) Patient NM: Left elbow pre and post treatment

R) Patient GY: Elbows pre and post treatment

S) Patient SG: Right elbow pre and post treatment

T) Patient SG: Left elbow pre and post treatment

U) Patient GO: Right elbow pre and post treatment

V) Patient GO: Left elbow pre and post treatment

W) Patient CB: Left elbow pre and post treatment

X) Patient PK: Right knee pre and post treatment

Y) Patient PK: Left knee pre and post treatment

Z) Patient CB: Right knee pre and post treatment

BASIDIOMYCETE-DERIVED CREAM FOR TREATMENT OF SKIN DISEASES

All patent and non-patent references cited in U.S. 61/763,014 as well as in this application are hereby incorporated by reference in their entirety. U.S. 61/763,014 is hereby also incorporated herein by reference in its entirety.

FIELD OF THE INVENTION

The product according to the present invention is produced in a production process using the mycelium of a mushroom like a Basidiomycete cell such as *Ganoderma lucidum*. The production process encourages the growing mycelium to export bioactive compounds such as beta glucans into the surrounding liquid. Thus, the beta glucan is soluble and easily absorbed. More importantly, the production process allows the beta glucan to retain its triple helix structure which is required for maintain a very high bioactive efficacy. The beta glucans from *Ganoderma lucidum* can be used in a cream for treatment of one or more skin diseases including psoriasis and eczema.

BACKGROUND

The medicinal mushroom *Ganoderma lucidum* has been used for a long time in China to prevent and treat various human diseases such as bronchitis, hepatitis, hypertension, tumorigenic diseases, immunological disorders and as an ingredient in skin creams. Ancient Chinese medical scholars suggested that *Ganoderma lucidum* could strengthen body resistance and consolidate the constitution of patients.

The main ingredients in the various *Ganoderma* products that lead to the bioactivity are beta glucans. These are part of the cell wall and are traditionally isolated in an extraction process. Unfortunately, the extraction process harms the bioactivity of the beta glucan and most applications are forced to use *Ganoderma* products in the form of a powder from the dried mushroom body. However, the beta glucan is not easily released from the powder so that it can be absorbed in the body and the biological efficacy of most *Ganoderma*-based products is affected by this.

The product according to the present invention can be produced in a production process using the mycelium of a mushroom such as *Ganoderma lucidum*. The production process encourages the growing mycelium to export bioactive compounds such as beta glucans into the surrounding liquid. Thus, the beta glucan is soluble and easily absorbed. More importantly, the production process allows the majority (such as more than 80%, more than 90% or more than 95%) or all of the beta glucan to retain its triple helix structure which is required for maintain a very high bioactive efficacy.

SUMMARY OF THE INVENTION

The present invention relates to novel bioactive agents such as polysaccharides like beta glucan as well as their use for treatment of one or more skin diseases such as psoriasis and eczema. The bioactive agents such as polysaccharides like beta glucan are derived from cells of the class Basidiomycete, for example microbial cells of the genera *Ganoderma*, *Agaricus*, *Schizophyllum*, *Lentinula*, *Trametes*, and *Grifola*. In particular *Ganoderma lucidum*, *Agaricus Blazei*, *Schizophyllum commune*, *Lentinula edodes*, *Trametes versicolor*, and *Grifola frondosa* are of interest.

In one embodiment, the polysaccharide according to the present invention has a molar ratio of galactose:mannose:glucose of 1:10 to 20:30 to 50, such as 1:12 to 18:35 to 45; for example 1:14 to 16:38 to 42, such as 1:about 15:about 40, for example 1:15:40. In another embodiment the polysaccharide according to the present invention has a molar ratio of galactose:mannose:glucose of 1:1 to 10:5 to 50 such as 1:2 to 8:5 to 15, such as 1:about 5:about 10.

In one embodiment, the polysaccharide according to the present invention has a molar ratio of galactose:mannose:glucose of 1:2 to 20:5 to 25, such as 1:3 to 18:5 to 20; for example 1:4 to 16:5 to 15, such as 1:about 5:about 10, for example 1:5:10. In another embodiment the polysaccharide according to the present invention has a molar ratio of galactose:mannose:glucose of 1:2 to 10:5 to 20 such as 1:4 to 6:8 to 12, such as 1:about 4 to 6:about 8 to 12.

The present invention also relates to methods for treating a skin disease, such as psoriasis and eczema with a skin cream comprising bioactive agents such as polysaccharides like beta glucan derived from cells of the class Basidiomycete, including *Ganoderma* such as *Ganoderma lucidum*.

There is also provided a method for enhancing a therapeutic effect of a skin disease medicament in an individual, said method comprising co-administering, simultaneously or sequentially in any order, said skin disease medicament in an effective amount with a bioactive agent according to the invention, such as a polysaccharide, or a composition according to the invention, wherein said bioactive agent or composition, when administered to said individual, enhances the therapeutic effect of said skin disease medicament.

In one aspect of the invention there is provided a method for cultivating a Basidiomycete cell in liquid culture medium, said method comprising the steps of providing a Basidiomycete cell capable of being cultivated in a liquid growth medium, and cultivating the Basidiomycete cell under conditions resulting in the production intracellularly or extracellularly of one or more bioactive agent(s) selected from the group consisting of oligosaccharides, polysaccharides, beta glucans, glycosylated peptides or polypeptides, oligonucleotides, polynucleotides, lipids, fatty acids, fatty acid esters, secondary metabolites such as polyketides, terpenes, steroids, shikimic acids, alkaloids and benzodiazepins.

In another embodiment is provided a composition comprising one or more polysaccharides, wherein:
a) a part such as the majority of the polysaccharides of the composition have a molecular weight of at least 10,000 Da such as at least 30,000 Da and wherein said mixture of polysaccharides can comprise the monosaccharides galactose, mannose and glucose e.g. in the ratio 1:0 to 25:1 to 50, and/or
b) a part such as the majority of the polysaccharides of the composition have a molecular weight of at least 50,000 Da such as at least 100,000 Da and wherein said mixture of polysaccharides can comprise the monosaccharides galactose, mannose and glucose e.g. in the ratio 0 to 0.5:0.5 to 10:0.5 to 50, and/or
c) a part such as the majority of the polysaccharides of the composition have a molecular weight of at least 1,000,000 Da and wherein said mixture of polysaccharides can comprise the monosaccharides galactose, mannose and glucose e.g. in the ratio 1:0 to 25:1 to 50.

In one embodiment the composition does essentially not comprise any polysaccharides with a molecular weight of less than 100,000 Da, less than 50,000 Da, less than 30,000 Da and/or less than 1,000 Da.

BRIEF DESCRIPTION OF THE DRAWINGS

FIG. 2.

FIG. 3A shows the state of a leg from a person with eczema as it normally appeared and FIG. 3B shows the same leg after two weeks with application of the skin cream comprising the beta glucan product from *Ganoderma lucidum*.

DEFINITIONS

Figure 1:
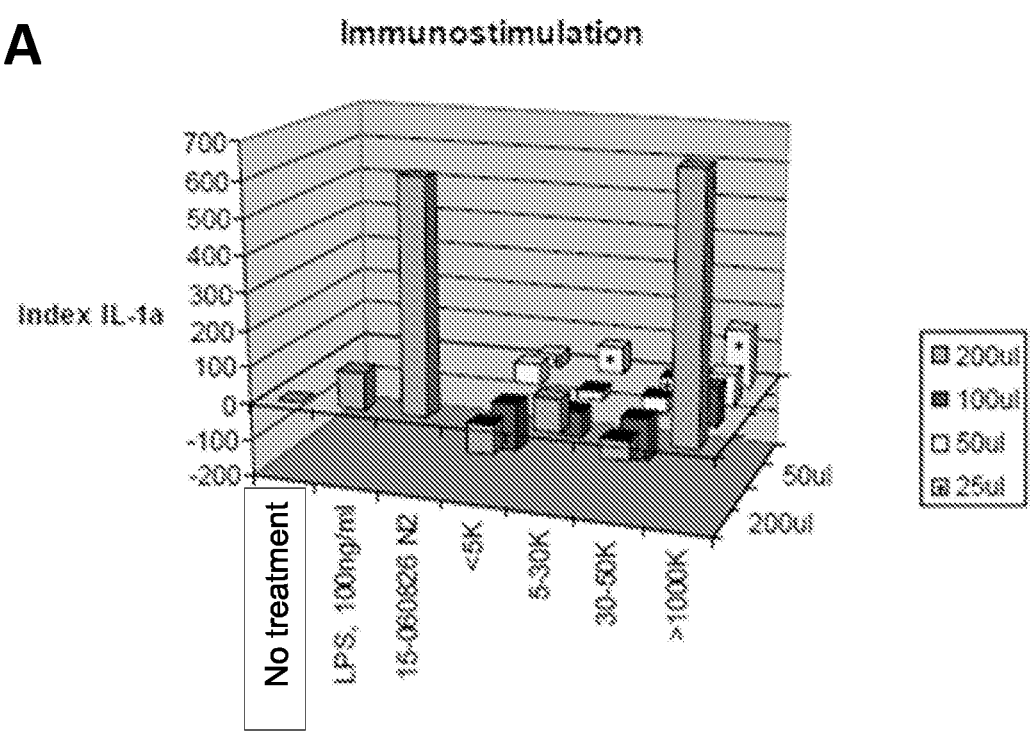
FIG. 1: Fractions of *Ganoderma* fermentation fluid were analysed as described in Example 2. The immune stimulatory effect was analysed for a dose response relationship for all the fractions. An immune stimulatory index was calculated relative to untreated cells (=index 0) and the positive control (LPS 100 ng/ml) (=index 100). It can be seen that the β-(1,3)-glucan is predominantly found in the high molecular weight fraction (>1000K).
Figure 1:
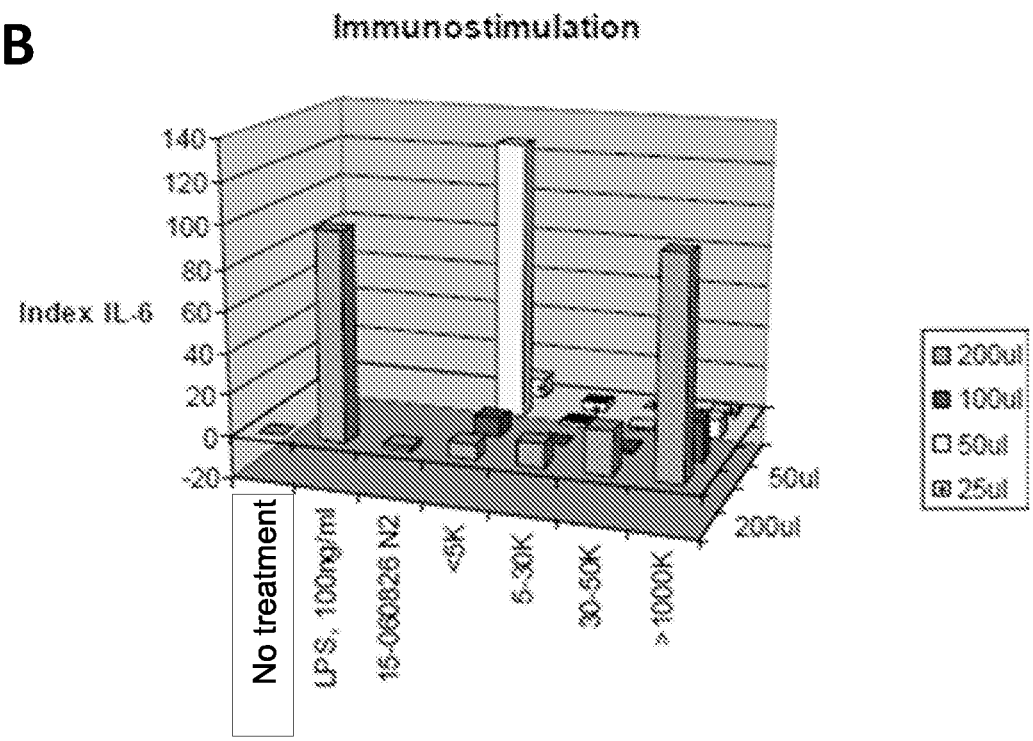

Basidiomycete cell: A cell from a fungus of the class Basidiomycete of the Phylum Basidiomycota, wherein the cell can be derived from any part of the fungus, such as fruiting body, hyphae, spores and mycelium. The Basidiomycete cell can be a single hyphae, spores, aggregates of mycelium, or partly differentiated mycelium, or comprised in fungal mycelium.

*Ganoderma* sp.: A basidiomycetous fungal species of the genus *Ganoderma* of the family Ganodermataceae and the order polyporales and the subclass agaricomycetidae.

*Agaricus* sp.: A basidiomycetous fungal species of the genus *Agaricus* of the family agaricaceae and the order agaricales and the subclass agaricomycetidae.

*Schizophyllum* sp.: A basidiomycetous fungal species of the genus *Schizophyllum* of the family schizophyllaceae and the order agaricales and the subclass agaricomycetidae.

*Lentinula* sp.: A basidiomycetous fungal species of the genus *Lentinula* of the family polyporaceae and the order polyporales and the subclass agaricomycetidae. *L. edodes* is also termed *Lentinula edodes*, which is placed in the family Marasmiaceae, in the order Agaricales and the subclass agaricomycetidae.

*Trametes* sp.: A basidiomycetous fungal species of the genus *Trametes* of the family polyporaceae and the order polyporales and the subclass agaricomycetidae.

*Grifola* sp.: A basidiomycetous fungal species of the genus *Grifola* of the family meripilaceae and the order polyporales and the subclass agaricomycetidae.

Bioactive agent: Any agent, drug, compound, composition of matter or mixture which provides a beneficial pharmacological effect that can be demonstrated in-vivo or in vitro. This includes beneficial pharmacological effects which can be demonstrated in an individual on a diet comprising an edible food, a food supplement, such as a composition of vitamins, a nutrient, or a nutriceutical comprising the bioactive agent. Also, the beneficial pharmacological effect can be observed in an individual being administered a medicament (drug), a combination of medicaments, a vaccine, or other beneficial agents comprising the bioactive agent. The bioactive agent can be provided in isolated and/or purified form, or in a solid or liquid composition, such as e.g. a solid composition comprising Basidiomycete biomass resulting from a submerged cultivation (i.e. when the bioactive agent is produced intracellularly), or preferably a liquid composition, such as e.g. extracellular growth medium comprising said bioactive agent (i.e. when the bioactive agent is secreted to the extracellular medium). The extracellular growth medium can be separated from the biomass, or from a part of said biomass, by e.g. filtration or centrifugation. There is also provided an Basidiomycete whole cell fermentation culture comprising both biomass and extracellular growth medium, said whole cell culture comprising said bioactive agent. The bioactive agent can be and/or comprise one or more polysaccharides and/or one or more beta glucans. As used herein, the bioactive agent can be any physiologically or pharmacologically bioactive agent from the Basidiomycete that produces a localized or systemic effect in an individual. Further examples of bioactive agents include, but not limited to agents comprising or consisting of an oligosaccharide, agents comprising or consisting of a polysaccharide, agents comprising or consisting of beta glucans, agents comprising or consisting of an optionally glycosylated peptide, agents comprising or consisting of an optionally glycosylated polypeptide, agents comprising or consisting of an oligonucleotide, agents comprising or consisting of a polynucleotide, agents comprising or consisting of a lipid, agents comprising or consisting of a fatty acid, agents comprising or consisting of a fatty acid ester and agents comprising or consisting of secondary metabolites.

Bioactive agents comprising an effect on one or more skin diseases: An agent derived from a Basidiomycete cell capable of counteracting or suppressing one or more skin diseases such as psoriasis and eczema.

Bioactive agents comprising an immune stimulating activity: Agents derived from a Basidiomycete cell effective in the stimulation or restoration of the ability of the immune system to fight infection and disease.

Bioactive agents comprising an anti-fungal activity: Inhibition or elimination of fungal growth in vitro or in vivo.

Bioactive agents comprising an anti-bacterial activity: Inhibition or elimination of bacterial growth in vitro or in vivo.

Bioactive agents comprising an anti-viral activity: Inhibition or elimination of viral replication in vitro or in vivo.

Bioactive agents comprising an anti-inflammatory activity: Agents capable of counteracting or suppressing tissue inflammation of an individual.

Bioactive agents comprising an anti-allergenic activity: Agents capable of counteracting or suppressing an allergy in an individual.

Beta glucans: beta glucans can consist of glucose only (i.e. a homopolymer), but preferable consists of glucose and other monosaccharides such as mannose and galactose (i.e. a heteropolymer). Accordingly, the term glucan can in one embodiment be the same as beta glycans. Beta glucans and beta glycans are used interchangably herein. The beta glucans/glycans can be linear and/or, branched. In a preferred embodiment the beta glucans/glycans comprise one or more 1,3 and/or 1,6 bindings. The 1,6 bindings can result in side chains in the beta glucans/glycans.

A glucan molecule is in one embodiment a polysaccharide of D-glucose monomers, linked by glycosidic bonds. Preferably, the beta glucan/glycan is compounds consisting of a large number of monosaccharides linked glycosidically. Glucans/glycans usually consist solely of 0-glycosidic linkages of monosaccharides. Glucans/glycans can be homo- or heteropolymers of monosaccharide residues, and can be linear or branched.

Liquid growth medium: The medium in which the Basidiomycete cell is cultivated. When used herein, the term "liquid culture" is used to indicate all forms of non-solid culture, including submerged culture and suspension culture. After cultivation, the initial composition of nutrients present in the liquid growth medium may have changed. Additionally, Basidiomycete extracellular products will be secreted from the mycelium to the extracellular growth medium during the cultivation. When used herein, the terms "biomass" and "extracellular" are intended to describe the cell-associated and non-cell-associated fractions of the liquid culture, respectively. "Removal of the biomass" indicates that a substantial part of the biomass is removed, preferably more than half, such as more than 90%, i.e. more than 96%, such as more than 98% of the biomass is removed.

Fruiting bodies or fruit bodies: Any one of a variety of complex, spore-bearing fungal structures.

Mycelium: Mass of hyphae constituting the body (thallus) of the fungus.

"Fermentation", cultivation" and "culturing" are used interchangeably herein.

Oligo: From 2 to 10, such as from 2 to 8, for example from 2 to 6, such as from 2 to 4. Examples include oligonucleotide and oligosaccharide.

Poly: More than 10.

Polysaccharide: Any biological polymer composed of monosaccharide (sub)units. The term "polysaccharide" as used herein is intended to cover polysaccharides as well as polysaccharides containing and/or covalently linked to peptides, polypeptides or the like, such as proteopolysaccharides. A polysaccharide is said to comprise monosaccharides, wherein said monosaccharides are covalently linked to form said polysaccharide. Hydrolysing a polysaccharide will yield the monosaccharides that formed said polysaccharide in free form. The monosaccharide content of a polysaccharide can thus be determined by hydrolysing the polysaccharide and measuring the presence of individual monosaccharides. The monosaccharide content of a mixture of polysaccharides is determined by determining the monosaccharide content of the entire mixture. When cited in combination with a molecular weight range or a monosaccharide content or ratio, "polysaccharide" shall also denote "polysaccharide(s) of the composition" or a "composition of polysaccharides" having molecular weight(s) falling within the cited molecular weight range.

Ratio: A polysaccharide or a mixture of polysaccharides are said to comprise e.g. arabinose, mannose, and glucose in a given ratio, when hydrolysation of said polysaccharide or said mixture of polysaccharide yields arabinose, mannose and glucose in said given ratio.

Molecular weight: Every polysaccharide of a composition is said to have a molecular weight of at least a given value, when said composition has been purified using a filtration step resulting in a molecular weight cut-off of said given value. Similarly, every polysaccharide of a composition is said to have a molecular weight within a given range, when said composition has been subjected to one or more filtration steps resulting in a lower molecular weight cut-off which is the lower value of the range and an upper molecular weight cut-off which is the upper value of the range. Said filtration step may for example be ultrafiltration, microfiltration, ultra-centrifugation or gel filtration.

However, a composition wherein every polysaccharide has a molecular weight of at least a given value or every polysaccharide is said to have a molecular weight within a given range may also be prepared by other methods.

Majority: The term "majority" can mean more than 50%, such as more than 60%, for example more than 70%, such as more than 80%, for example more than 90%, such as more than 95% or more than 99%.

Treatment: The terms "treating", "treatment" and "therapy" as used herein refer equally to curative therapy, prophylactic therapy, and preventative therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 90% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

The terms "enhancing" and "improving" a beneficial effect, and variations thereof, as used herein, refers to the therapeutic effect of the bioactive agent against placebo, or an increase in the therapeutic effect of a state-of-the-art medical treatment above that normally obtained when a pharmaceutical composition is administered without the bioactive agent of this invention. "An increase in the therapeutic effects" is manifested when there is an acceleration and/or increase in intensity and/or extent of the therapeutic effects obtained as a result of administering the bioactive agent(s). It also includes extension of the longevity of therapeutic benefits. It can also manifest where a lower amount of the pharmaceutical composition is required to obtain the same benefits and/or effects when it is co-administered with bioactive agent(s) provided by the present invention as compared to the administration in a higher amount of the pharmaceutical composition in the absence of bioactive agent. The enhancing effect preferably, but not necessarily, results in treatment of acute symptoms for which the pharmaceutical composition alone is not effective or is less effective therapeutically. Enhancement is achieved when there is at least a 5% increase in the therapeutic effects, such as at least 10% increase in the therapeutic effects when a bioactive agent of the present invention is co-administered with a pharmaceutical composition compared with administration of the pharmaceutical composition alone. Preferably the increase is at least 25%, more preferably at least 50%, even more preferably at least 75%, most preferably at least 90%.

"Co-administering" or "co-administration" of bioactive agent(s), or bioactive agents and state-of-the-art medicaments, as used herein, refers to the administration of one or more bioactive agents of the present invention, or administration of one or more bioactive agents of the present invention and a state-of-the-art pharmaceutical composition within a certain time period. The time period is preferably less than 24 hours, such as less than 12 hours, for example less than 6 hours. such as less than 3 hours. However, these terms also mean that the bioactive agent and a therapeutic composition can be administered together.

Individual: The term refers to vertebrates, particular members of the mammalian species, and includes, but is not limited to domestic animals, such as cattle, horses, pigs, sheep, mink, dogs, cats, mice, guinea pigs, rabbits, rats; sports animals, such as horses, poly ponies, dogs, camels, and primates, including humans.

Transdermal administration: is a route of administration wherein bioactive agent s are delivered across the skin for systemic distribution. Examples include transdermal patches e.g. used for medicine delivery, and transdermal implants e.g. used for medical or aesthetic purposes.

Transdermal patch: is a medicated adhesive patch comprising e.g. the bioactive agent according to the present invention that is placed on the skin to deliver a specific dose of medication through the skin and into the bloodstream. The patch provides a controlled release of the medication into the patient, usually through either a porous membrane covering a reservoir of medication or through body heat melting thin layers of medication embedded in the adhesive.

Psoriasis: is an autoimmune disease that affects the skin. It occurs when the immune system mistakes the skin cells as a pathogen, and sends out faulty signals that speed up the growth cycle of skin cells. There are five types of psoriasis: plaque, guttate, inverse, pustular, and erythrodermic. In plaque psoriasis, skin rapidly accumulates at these sites, which gives it a silvery-white appearance. Plaques frequently occur on the skin of the elbows and knees, but can affect any area, including the scalp, palms of hands and soles of feet, and genitals. In contrast to eczema, psoriasis is more likely to be found on the outer side of the joint.

Psoriasis is a chronic recurring condition that varies in severity from minor localized patches to complete body coverage. Fingernails and toenails are frequently affected (psoriatic nail dystrophy) and can be seen as an isolated sign. Psoriasis can also cause inflammation of the joints, which is known as psoriatic arthritis.

The cause of psoriasis is not fully understood, but it is believed to have a genetic component and local psoriatic changes can be triggered by an injury to the skin known as the Koebner phenomenon. Various environmental factors have been suggested as aggravating to psoriasis, including oxidative stress, stress, withdrawal of systemic corticosteroid, as well as other environmental factors, but few have shown statistical significance.

DETAILED DESCRIPTION OF THE INVENTION

The present invention in one embodiment relates to methods for cultivating a Basidiomycete cell in a liquid culture medium. The methods comprise the steps of providing a Basidiomycete cell capable of being cultivated in a liquid growth medium, and cultivating the Basidiomycete cell under conditions resulting in the production intracellularly and/or extracellularly of one or more bioactive agent(s) comprising or consisting of an agent selected from the group of agents consisting of oligosaccharides, polysaccharides, beta glucans, optionally glycosylated oligopeptides or polypeptides, optionally modified oligonucleotides, optionally modified polynucleotides, lipids, fatty acids, fatty acid esters, and secondary metabolites, such as polyketides, terpenes, steroids, shikimic acids, alkaloids and benzodiazepins.

In one embodiment it is preferred that the mixture of polysaccharides comprises the monosaccharides galactose, mannose, and glucose in the ratio (0-1.5):(0-0.5) to (15-35):(0.5-1.5) to (45-55), such as e.g. any of the following:
(0-1.5):(0-0.5) to (15-35):(0.5-1.5) to (45-55),
(0.8-1.2):(0-0.5) to (20-30):(0.5-1.5) to (45-55),
(0-1.5):(0-0.1) to (15-35):(0.5-1.5) to (45-55),
(0.8-1.2):(0-0.5) to (15-35):(0.5-1.5) to (45-55),
(0-1.5):(0-0.5) to (20-30):(0.5-1.5) to (48-52),
(0.8-1.2):(0-0.5) to (15-35):(0.5-1.5) to (48-52),
(0-1.5):(0-0.1) to (15-35):(0.5-1.5) to (48-52),
(0.8-1.2):(0-0.1) to (15-35):(0.5-1.5) to (48-52),
(0-1.5):(0-0.5) to (20-30):(0.5-1.5) to (49-51),
(0.8-1.2):(0-0.5) to (15-35):(0.5-1.5) to (49-51),
(0-1.5):(0-0.1) to (15-35):(0.5-1.5) to (49-51),
(0.8-1.2):(0-0.1) to (20-30):(0.5-1.5) to (49-51),
(0-1.5):(0-0.5) to (15-35):(0.5-1.5) to (45-55),
(0.8-1.2):(0-0.5) to (15-35):(0.5-1.5) to (45-55),
(0-1.5):(0-0.5) to (20-30):(0.5-1.5) to (48-52),
(0.8-1.2):(0-0.5) to (15-35):(0.5-1.5) to (48-52),
(0-1.5):(0-0.5) to (15-35):(0.5-1.5) to (49-51),
(0.8-1.2):(0-0.5) to (20-30):(0.5-1.5) to (49-51).
Production Method The production process uses an edible mushroom growing on edible ingredients which leads to a very safe product that can be ingested by humans. However, in this context, the beta glucan product can also be included in a skin cream which can be applied topically.

In the production process, the mushroom is encouraged to produce the product you are after, in this case the beta glucans, with no or limited unwanted by-products. In one embodiment the purification process is primarily removal the biomass, leaving a clear liquid product. In another aspect the purification of the beta glucans comprises one or more size fractionation steps such as gel filtration or ultracentrifugation. In one embodiment no solvents are used in the production process.

In one embodiment of the present invention the bioactive agent disclosed herein has been produced by a Basidiomycete cell. The bioactive agent can be utilised for many purposes when it is present in the extracellular, liquid growth medium, or the bioactive agent can optionally be purified from the extracellular environment of an Basidiomycete cell. The mycelium of the Basidiomycete cell is preferably cultivated in a liquid growth medium and the bioactive agent is preferably purified from said liquid growth medium.

It is thus preferred that the bioactive agent of the invention is either isolated and/or purified, or forms part of a solid or liquid composition which can be produced by a method comprising the initial steps of
  i) cultivating a Basidiomycete cell such as *Ganoderma* such as *Ganoderma lucidum* in a liquid growth medium, and
  ii) isolating the Basidiomycete biomass comprising said bioactive agent, and/or isolating a liquid composition comprising the bioactive agent, from said liquid growth medium.

The bioactive agent can subsequently be further extracted, isolated or purified from the liquid composition if needed—e.g. by one or more size fractionation steps. The liquid growth medium may be any of the liquid growth media described herein below.

The Basidiomycete biomass may be in the form of e.g. single hyphae, spores, aggregates of mycelium, and partly differentiated mycelium.

Preferably, the Basidiomycete cell is cultivated in a liquid growth medium. The Basidiomycete cell can be any fungal cell of the genus *Agaricus, Schizophyllum, Lentinula, Trametes, Ganoderma* such as *Ganoderma lucidum* and *Grifola*. Cultivating the fungus in a liquid growth medium in general involves dissolving nutrient compounds required for growth of said fungus in water, transferring the solution to a bioreactor and inoculating the bioreactor with cells or spores of the fungus, such as a fungal mycelium, or fractions thereof, to be cultivated. This is done under sterile conditions and with control of the environment in order to give the fungus a suitable chemical and physical environment. Cultivating fungi in liquid growth medium is also termed "liquid state" cultivation.

During "liquid-state" cultivation the medium with the fungal biomass is preferably agitated to reduce the occurrence of gradients and to ensure oxygen availability to the submerged cells. When fungi are grown in a bioreactor, oxygen may be supplied to the liquid medium and the level of dissolved oxygen may be controlled by known methods. The oxygen can be supplied in the form of air from the atmosphere or in the form of pure oxygen.

The liquid growth medium is an aqueous solution, preferably sterile water, comprising nutrient compounds. The liquid medium supports fungal growth and preferably stimulates the production of extracellular bioactive agents, such as immune modulating agents. The liquid growth medium may comprise one or more typical ingredients required for growth of microbial organisms such as malt extract, yeast extract, peptone, glucose, sucrose, salts providing phosphate, magnesium and potassium, corn-steep liquor and vitamins such as thiamine. More preferably, the medium comprises glucose and/or sucrose, corns steep liquor, phosphate and magnesium for mycelium growth and production of polysaccharides.

In a preferred embodiment for liquid cultivation the medium comprises malt extract. This embodiment is in particular relevant for production of food or feed products comprising biomass or a composition isolated from biomass. More preferably the medium may comprise malt extract, a sugar source and an amino acid source, even more preferably malt extract, glucose, yeast extract and peptone. The malt extract may preferably be at a concentration in the range of 1 to 20, such as 1 to 10, for example 2 to 4 g/l. Glucose may preferably be at a concentration of less than 40 g/l, such as in the range of 25 to 35, for example in the range of 28 to 32 g/l. Peptone may preferably be at a concentration of less than 20, such as in the range of 10 to 20, for example in the range of 12 to 18 g/l. Yeast extract may preferably be in a concentration of in the range of 1 to 10, preferably around 3 g/l.

For inoculation of the growth medium, fungal mycelium from agar plates containing for example malt extract, yeast extract, peptone and glucose can be used. Fungi can initially be cultivated on agar plates comprising the above nutrient compounds supporting the growth of the fungus. The plates are inoculated with mycelium and incubated at least until a visible growth is evident on the plates. Dependent on the fungus, this usually can take from about 7 days to about 24 days or from about 10 to 30 days, typically 14 days or up to 20 days, at a temperature in the range of from 18 to 32° C., preferably in the area of from 22 to 30° C., such as a temperature of about 23° C. to 27° C., such as around 25° C.

As an alternative to inoculation with mycelium from agar plates, inoculation of the growth medium can be carried out by using mycelium from a fermentation broth in e.g. a shake flask medium comprising nutrient compounds supporting cell growth. Shake flasks for cultivating fungal mycelium can initially be inoculated with the mycelium which is cultivated on agar plates. The mycelium is taken from the plates and transferred aseptically to shake flasks containing sterile water comprising dissolved nutrient compounds and nutrient salts supporting the growth of the fungal mycelium. A typical growth medium contains glucose and/or sucrose, corn steep liquor, phosphate and magnesium. The amount of inoculation material which gives the highest production of extracellular bioactive agent can be selected following initial experiments.

The time for incubation of the shake flasks depends on the specific fungus. Typically, the shake flasks can be incubated by shaking for 6 to 21 days, preferably from 7 to 18 days, more preferably from 8 to 14 days at a temperature in the range of from 18 to 32° C., preferably in the area of from 22 to 30° C., such as a temperature of about 23° C., for example 24° C., such as 25° C., for example 26° C., such as 27° C., for example 28° C., such as 29° C., for example 30° C. The shake flasks may also be incubated from 8-25 days, more preferably from 10-20 days, more preferably from 12-18 days. The temperature may also be from 18 to 37° C., preferably from 23 to 32° C. such as about 25° C.

The content of the shake flasks can be used for inoculating a bioreactor. In that case, the reactor comprises a sterile solution of nutrient compounds and nutrient salts in water for mono-culture cultivation of Basidiomycete mycelium.

The bioreactor fermentation period is typically in the range of from 50 hours to 300 hours, preferably in the range of from 80 hours to 270 hours, and the temperature is kept constant in the range of 18 to 32° C., preferably in the area of from 22 to 31° C. such as a temperature of about 23° C., for example 24° C., such as 25° C., for example 26° C., such as 27° C., for example 28° C., such as 29° C., for example 30° C. The temperature may also be from 18 to 37° C., preferably from 23 to 32° C. such as about 25° C.

The reactor is fitted with an inlet for supplying air to the fermentation broth, and the fermentation broth is preferably kept under continuous agitation either as a result of the addition of air, or by means of a mixer device suitable for providing a good mixing of the content of the reactor.

It is preferred to adjust the pH of the growth medium to from about 3 to about 7, such as a pH of from about 4.5 to about 6.5, for example a pH of about 6, before the growth medium is inoculated with fungal mycelium, or fractions thereof, such as *L. edodes* mycelium. After the initial adjustment, pH may be dropped naturally during the course of the fermentation, or controlled at a particular value in the range pH 3 to 7, using addition of suitable pH-control agents, such as acid and base. The temperature of the growth medium is preferably in the range of from 18 to 32° C., preferably in the area of from 22 to 31° C., such as a temperature of about 23° C., for example 24° C., such as 25° C., for example 26° C., such as 27° C., for example 28° C., such as 29° C., for example 30° C. The temperature may also be from 18 to 37° C., preferably from 23 to 32° C. such as about 25° C.

Samples can be obtained from the bioreactor and analysed for biomass, metabolic products and nutrient compounds, the determinations of which can assist the operator of the bioreactor in the running of the fermentation process. Typical analyses routinely carried out are determination of biomass, residual sugar concentration and extracellular polysaccharide concentration. A person skilled in the art knows the methods for analysis which can be employed in this respect.

Isolating the Bioactive Agent or a Composition Comprising a Bioactive Agent

Preferably, the method for preparing the products according to the invention involves a step of purifying the extracellular fraction of the liquid growth medium from the fungal mycelium. The extracellular fraction of the liquid fermentation medium is also termed the supernatant and this fraction can be separated from the fungal mycelium by e.g. centrifugation or filtration, or indeed by any other means available for obtaining a liquid fraction essentially without any fungal mycelium present therein. The term "essentially without any fungal mycelium present therein" shall denote that the concentration of fungal mycelium, including fractions thereof, has been reduced at least by a factor of $10^3$, such as reduced by a factor of at least $10^4$, for example a factor of at least $10^5$, such as reduced by a factor of at least $10^6$.

The methods for preparing the products according to the invention may further comprise isolating an extracellular composition comprising a survival enhancing agent. In preferred embodiments of the invention the isolation comprises at least one size fractionation step. Preferably, this size fractionation step is performed on the extracellular fraction. This size fractionation step may ensure that every polysaccharide of the composition has a molecular weight of at least a given value. The size fractionation step may be any size fraction known to the skilled person, for example ultracentrifugation, ultrafiltration, microfiltration or gel filtration. Thus in a preferred embodiment of the invention, the composition is purified from a liquid growth medium by a method involving one or more purification steps selected from the group consisting of ultracentrifugation, ultrafiltration, microfiltration and gel filtration. Preferably, the purification step(s) are selected from the group consisting of ultrafiltration, microfiltration and ultracentrifugation, even more preferably from the group consisting of ultrafiltration and microfiltration.

Ultrafiltration is a membrane based process where the membrane fractionates components of a liquid according to size. The membrane configuration is normally cross-flow wherein the liquid containing the relevant components are flowing across the membrane. Some of the liquid, containing components smaller than the nominal pore size of the membrane will permeate through the membrane. Molecules larger than the nominal pore size will be retained. The desired product may be in the retentate or the filtrate. If the ultrafiltration is performed in order to prepare a composition, wherein every polysaccharide within said composition has a molecular weight above a given value, the desired product is in the retentate. If a serial fractionation is made, the product may be in the retentate or filtrate.

Microfiltration is a membrane separation process similar to UF but with even larger membrane pore size allowing larger particles to pass through.

Gel filtration is a chromatographic technique in which particles are separated according to size. The filtration medium will typically be small gel beads which will take up the molecules that can pass through the bead pores. Larger molecules will pass through the column without being taken up by the beads.

Gel-filtration, ultrafiltration or microfiltration may for example be performed as described in R Hatti-Kaul and B Mattiasson (2001), *Downstream Processing in Biotechnology*, in Basic Biotechnology, eds C Ratledge and B Kristiansen, Cambridge University Press) pp 189.

The invention relates to a method of producing a composition according to the present invention, said method comprising the steps of
a) cultivating a fungus of the genus *Lentinula* or the genus *Ganoderma* in a liquid growth medium under appropriate conditions to provide a suitable chemical and physical environment supporting the growth of a fungus of the genus *Lentinula* or the genus *Ganoderma* in a liquid growth medium, and
b) separating the liquid growth medium from the fungus cells
c) isolating the composition according to the invention from said liquid growth medium by one or more fractionation steps such as one or more size fractionation steps and retaining said composition for further use.

In one embodiment the above cited method does not comprise alcohol extraction and/or alcohol precipitation e.g. to maintain all or the majority of the polysaccharides and/or beta glucans in their native conformation.

A non-limiting method of preparing the products according to the invention is described in the examples.

Composition

The present invention relates to composition comprising or consisting of beta glucans derived from the liquid growth medium of a liquid culture of one or more Basidiomycetes. The composition can be used for treatment of one or more skin diseases such as psoriasis and eczema.

The Basidiomycetes are preferably *Ganoderma* such as *Ganoderma lucidum*.

In one embodiment the liquid growth medium of a liquid culture of one or more Basidiomycetes is fractionated to obtain a fraction wherein the majority or all of the beta glucans have a molecular weight of e.g. at least 1 kDa, at least 30 kDa, at least 50 kDa, at least 100 kDa or at least 1000 kDa.

In one embodiment the composition—such as a cream or lotion—can comprise as the active ingredient growth medium from a liquid *Lentinula edodes* and/or *Ganoderma* culture (no size fractionation).

In one embodiment the composition—such as a cream or lotion—can comprise as the active ingredient a fraction of growth medium from a liquid *Lentinula edodes* and/or *Ganoderma* culture with MW>10 kDa.

In one embodiment the composition—such as a cream or lotion—can comprise as the active ingredient a fraction of growth medium from a liquid culture of *Lentinula edodes* and/or *Ganoderma* culture with MW>100 kDa.

In one embodiment the composition—such as a cream or lotion—can comprise as the active ingredient a fraction of growth medium from a liquid *Lentinula edodes* and/or *Ganoderma* culture with MW>1000 kDa.

In one embodiment the composition—such as a cream or lotion—can comprise as the active ingredient a fraction of growth medium from a liquid culture of *Ganoderma lucidum* with MW>100 kDa.

In one embodiment the composition—such as a cream or lotion—can comprise as the active ingredient an isolated composition comprising a mixture of polysaccharides, wherein the majority of the polysaccharides of the composition have a molecular weight of at least 30,000 Da, wherein a first part of said polysaccharides have a molecular weight of from 30,000 Da to 1,000,000 Da, wherein a second part of said polysaccharides have a molecular weight of at least 1,000,000 Da, wherein essentially no polysaccharides have a molecular weight of less than 30,000 Da, wherein said mixture of polysaccharides comprises the monosaccharides galactose, mannose and glucose e.g. in the ratio 1:0.033 to 500:1 to 50, and wherein the composition is produced by a method comprising the steps of a) cultivating a fungus e.g. of the genus *Lentinula* or the genus *Ganoderma* in a liquid growth medium under appropriate conditions to provide a suitable chemical and physical environment supporting the growth of a fungus of the genus *Lentinula* or the genus *Ganoderma* in a liquid growth medium, and b) isolating the composition from said liquid growth medium.

In one embodiment the composition—such as a cream or lotion—can comprise as the active ingredient an aqueous, liquid composition comprising a mixture of polysaccharides, wherein the majority of the polysaccharides of the composition have a molecular weight of at least 1,000,000 Da, wherein essentially no polysaccharides have a molecular weight of less than 1,000,000 Da, wherein said mixture of polysaccharides comprises the monosaccharides galactose, mannose and glucose e.g. in the ratio 1:0.033 to 500:1 to 50, and wherein the composition is produced by a method comprising the steps of a) cultivating a fungus of the genus *Lentinula* or the genus *Ganoderma* in a liquid growth medium under appropriate conditions to provide a suitable chemical and physical environment supporting the growth of a fungus of the genus *Lentinula* or the genus *Ganoderma* in a liquid growth medium, and b) isolating the composition from said liquid growth medium.

In one embodiment the composition—such as a cream or lotion—can comprise as the active ingredient an isolated, aqueous liquid immune stimulating composition comprising a mixture of polysaccharides comprising the monosaccharide units galactose, mannose and glucose, wherein: the majority of the polysaccharides of the composition have a molecular weight of at least 1,000 Da wherein a first part of said polysaccharides have a molecular weight of less than 1,000,000 Da, wherein a second part of said polysaccharides have a molecular weight of at least 1,000,000 Da, wherein said mixture of polysaccharides comprises the monosaccharides galactose, mannose and glucose e.g. in the ratio 1:0.033 to 500:1 to 50, and wherein the composition is produced by a method comprising the steps of; a) cultivating a fungus of the genus *Lentinula* or the genus *Ganoderma* in a liquid growth medium under appropriate conditions to provide a suitable chemical and physical environment supporting the growth of a fungus of the genus *Lentinula* or the genus *Ganoderma* in the liquid growth medium, b) isolating the composition from said liquid growth medium by one or more size fractionation steps, and c) retaining said composition for further use.

In one aspect of the invention the composition—such as a cream or lotion—comprises from 0.002 g/ml to 0.0002 g/ml of beta glucans such as beta glucans from *Ganoderma* such as beta glucans from *Ganoderma lucidum*.

The composition can in one embodiment comprise at least 0.00002 g/ml, such as at least 0.00004 g/ml, for example at least 0.00006 g/ml, such as at least 0.00008 g/ml, for example at least 0.0001 g/ml, such as at least 0.00015 g/ml, for example at least 0.0002 g/ml, such as at least 0.0004 g/ml, for example at least 0.0006 g/ml, such as at least 0.0008 g/ml, for example at least 0.001 g/ml, such as at least 0.002 g/ml, for example at least 0.004 g/ml, such as at least 0.006 g/ml, for example at least 0.008 g/ml, such as at least 0.010 g/ml or for example at least 0.1 g/ml of beta glucans such as beta glucans from *Ganoderma* such as beta glucans from *Ganoderma lucidum*.

The composition can in one embodiment comprise less than 0.1 g/ml, such as less 0.01 g/ml, for example less than 0.008, such as less 0.006 g/ml, for example less than 0.004, such as less 0.002 g/ml, for example less than 0.001, such as less 0.0008 g/ml, for example less than 0.0006, such as less 0.0004 g/ml, for example less than 0.0002, such as less 0.0001 g/ml, for example less than 0.00008, such as less 0.00006 g/ml, for example less than 0.00004, such as less 0.00002 g/ml, for example less than 0.00001, such as less 0.000001 g/ml or for example less than 0.0000001 of beta glucans such as beta glucans from *Ganoderma* such as beta glucans from *Ganoderma lucidum*.

The composition can comprise an amount of beta glucans selected from the group consisting of from 0.0000001 g/ml to 0.000001 g/ml, from 0.000001 g/ml to 0.00001 g/ml, from 0.00001 g/ml to 0.00002 g/ml, from 0.00002 g/ml to 0.00004 g/ml, from 0.00004 g/ml to 0.00006 g/ml, from 0.00006 g/ml to 0.00008 g/ml, from 0.00008 g/ml to 0.0001 g/ml, from 0.0001 g/ml to 0.00015 g/ml, from 0.00015 g/ml to 0.0002 g/ml, from 0.0002 g/ml to 0.0004 g/ml, from 0.0004 g/ml to 0.0006 g/ml, from 0.0006 g/ml to 0.0008 g/ml, from 0.001 g/ml to 0.002 g/ml, from 0.002 g/ml to 0.004 g/ml, from 0.004 g/ml to 0.006 g/ml, from 0.006 g/ml to 0.008 g/ml, from 0.008 g/ml to 0.01 g/ml, and from 0.01 g/ml to 0.1 g/ml of beta glucans such as beta glucans from *Ganoderma* such as beta glucans from *Ganoderma lucidum* or any combination of these intervals.

The composition according to the present invention can in one embodiment comprise one or more beta glucans from *Ganoderma* such as *Ganoderma lucidum*. The amount of the one or more beta glucans from *Ganoderma* such as *Ganoderma lucidum* can e.g. be selected from the group consisting of from 0.001% (w/w) to 0.01% (w/w), from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7%

(w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w) of one or more penetrants per weight of the composition, or any combination of these intervals.

The composition according to the present invention can further comprise coconut fat. In one embodiment the composition comprises an amount of coconut fat selected from the group consisting of from 0.02 g/ml to 0.05 g/ml, from 0.05 g/ml to 0.1 g/ml, from 0.1 g/ml to 0.15 g/ml, from 0.15 g/ml to 0.2 g/ml, from 0.2 g/ml to 0.25 g/ml, from 0.25 g/ml to 0.3 g/ml, from 0.3 g/ml to 0.35 g/ml, from 0.35 g/ml to 0.4 g/ml, from 0.4 g/ml to 0.45 g/ml, and from 0.45 g/ml to 0.5 g/ml of coconut fat.

The composition according to the present invention can further comprise paraffin such as liquid paraffin. In one embodiment the composition comprises an amount of paraffin such as liquid paraffin selected from the group consisting of from 0.005 g/ml to 0.01 g/ml, from 0.01 g/ml to 0.015 g/ml, from 0.015 g/ml to 0.02 g/ml, from 0.02 g/ml to 0.025 g/ml, from 0.025 g/ml to 0.03 g/ml, from 0.03 g/ml to 0.035 g/ml, from 0.035 g/ml to 0.04 g/ml, from 0.04 g/ml to 0.045 g/ml, from 0.045 g/ml to 0.05 g/ml, from 0.05 g/ml to 0.055 g/ml, from 0.055 g/ml to 0.06 g/ml, from 0.06 g/ml to 0.065 g/ml, from 0.065 g/ml to 0.07 g/ml, from 0.07 g/ml to 0.08 g/ml, from 0.08 g/ml to 0.09 g/ml, from 0.09 g/ml to 0.1 g/ml, from 0.1 g/ml to 0.2 g/ml, from 0.2 g/ml to 0.5 g/ml, or any combination of intervals.

The composition according to the present invention can further comprise stearic acid. In one embodiment the composition comprises an amount of stearic acid selected from the group consisting of from 0.005 g/ml to 0.01 g/ml, from 0.01 g/ml to 0.015 g/ml, from 0.015 g/ml to 0.02 g/ml, from 0.02 g/ml to 0.025 g/ml, from 0.025 g/ml to 0.03 g/ml, from 0.03 g/ml to 0.035 g/ml, from 0.035 g/ml to 0.04 g/ml, from 0.04 g/ml to 0.045 g/ml, from 0.045 g/ml to 0.05 g/ml, from 0.05 g/ml to 0.055 g/ml, from 0.055 g/ml to 0.06 g/ml, from 0.06 g/ml to 0.065 g/ml, from 0.065 g/ml to 0.07 g/ml, from 0.07 g/ml to 0.08 g/ml, from 0.08 g/ml to 0.09 g/ml, from 0.09 g/ml to 0.1 g/ml, from 0.1 g/ml to 0.2 g/ml, from 0.2 g/ml to 0.5 g/ml, or any combination of intervals.

The composition according to the present invention can further comprise glycerol. In one embodiment the composition comprises an amount of glycerol selected from the group consisting of from 0.005 g/ml to 0.01 g/ml, from 0.01 g/ml to 0.015 g/ml, from 0.015 g/ml to 0.02 g/ml, from 0.02 g/ml to 0.025 g/ml, from 0.025 g/ml to 0.03 g/ml, from 0.03 g/ml to 0.035 g/ml, from 0.035 g/ml to 0.04 g/ml, from 0.04 g/ml to 0.045 g/ml, from 0.045 g/ml to 0.05 g/ml, from 0.05 g/ml to 0.055 g/ml, from 0.055 g/ml to 0.06 g/ml, from 0.06 g/ml to 0.065 g/ml, from 0.065 g/ml to 0.07 g/ml, from 0.07 g/ml to 0.08 g/ml, from 0.08 g/ml to 0.09 g/ml, from 0.09 g/ml to 0.1 g/ml, from 0.1 g/ml to 0.2 g/ml, from 0.2 g/ml to 0.5 g/ml, or any combination of intervals.

The composition according to the present invention can further comprise honey. In one embodiment the composition comprises an amount of honey selected from the group consisting of from 0.005 g/ml to 0.01 g/ml, from 0.01 g/ml to 0.015 g/ml, from 0.015 g/ml to 0.02 g/ml, from 0.02 g/ml to 0.025 g/ml, from 0.025 g/ml to 0.03 g/ml, from 0.03 g/ml to 0.035 g/ml, from 0.035 g/ml to 0.04 g/ml, from 0.04 g/ml to 0.045 g/ml, from 0.045 g/ml to 0.05 g/ml, from 0.05 g/ml to 0.055 g/ml, from 0.055 g/ml to 0.06 g/ml, from 0.06 g/ml to 0.065 g/ml, from 0.065 g/ml to 0.07 g/ml, from 0.07 g/ml to 0.08 g/ml, from 0.08 g/ml to 0.09 g/ml, from 0.09 g/ml to 0.1 g/ml, from 0.1 g/ml to 0.2 g/ml, from 0.2 g/ml to 0.5 g/ml, or any combination of intervals.

The composition according to the present invention can further comprise benzoate, such as an amount of benzoate selected from the group consisting of from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7% (w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w), or any combination of these intervals.

The composition according to the present invention can further comprise sorbate, such as an amount of sorbate selected from the group consisting of from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7% (w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w), or any combination of these intervals.

The composition according to the present invention can further comprise hyaluronic acid, such as an amount of hyaluronic acid selected from the group consisting of from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7% (w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w), or any combination of these intervals.

The composition according to the present invention can further comprise propylene glycol, such as an amount of propylene glycol selected from the group consisting of from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7% (w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w), or any combination of these intervals.

The composition according to the present invention can further comprise one or more vasoconstricting substances. The amount of the one or more vasoconstricting substances can e.g. be selected from the group consisting of from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7% (w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w) of one or more vasoconstricting substances per weight of the composition, or any combination of these intervals.

The one or more vasoconstricting substances can be selected from the group consisting of Oxymetazoline, Otrivine, Amphetamines, Antihistamines, Cocaine, LSD, LSA, Methylphenidate, Mephedrone, Phenylephrine, Propylhexedrine, Pseudoephedrine, Caffeine, Tetrahydrozoline hydrochloride and Psilocybin.

The composition according to the present invention can further comprise one or more humectants. The amount of the one or more humectants can e.g. be selected from the group consisting of from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7% (w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w) of one or more humectants per weight of the composition, or any combination of these intervals.

The one or more humectants can be selected from the group consisting of hyaluronic acid, proteins, acids, polysaccharides, and various small molecules (e.g. glycerine, sorbitol, urea, aloe vera etc.).

The composition according to the present invention can further comprise one or more penetrants. The amount of the one or more penetrants can e.g. be selected from the group consisting of from 0.01% (w/w) to 0.02% (w/w), from 0.02% (w/w) to 0.04% (w/w), from 0.04% (w/w) to 0.06% (w/w), from 0.06% (w/w) to 0.08% (w/w), from 0.08% (w/w) to 0.1% (w/w), from 0.1% (w/w) to 0.2% (w/w), from 0.2% (w/w) to 0.3% (w/w), from 0.3% (w/w) to 0.4% (w/w), from 0.4% (w/w) to 0.5% (w/w), from 0.5% (w/w) to 0.6% (w/w), from 0.6% (w/w) to 0.7% (w/w), from 0.7% (w/w) to 0.8% (w/w), from 0.8% (w/w) to 0.9% (w/w), from 0.9% (w/w) to 1% (w/w), from 1% (w/w) to 2% (w/w), from 2% (w/w) to 5% (w/w) of one or more penetrants per weight of the composition, or any combination of these intervals.

The one or more penetrants can e.g. be propylene glycol.

Another option is to use an initial (e.g. in the first week) topical colloid dressing impregnated with the composition according to the present invention on the plaque of psoriasis to assist absorption and soften the plaque at the same time.

The composition disclosed herein above can be in any suitable form for treatment of a skin condition such in the form of a salve, balm, cream, lotion, ointment or spray.

The invention further relates to a pharmaceutical composition comprising the composition according to the present invention and a pharmaceutically acceptable carrier.

The invention also relates to a kit comprising the composition according to the present invention and a dosage regime instruction with guidelines for dose and time administration.

In one preferred embodiment the cream or lotion comprises or contains from 0.5 to 5 mg/ml of the one or more beta glucans from *Ganoderma* such as *Ganoderma lucidum* such as from 1 mg/ml to 2 mg/ml such as 1 mg/ml or 2 mg/ml.

Clinical Indications

The composition according to the present invention can be used a medicament.

Bioactive agents having pharmaceutically relevant activities are provided in accordance with the present invention. The pharmaceutically active agents can thus be administered to a human or animal with a view to obtaining a therapeutic effect. The bioactive agents can be administered on their own or as part of a combination treatment further involving at least one additional bioactive agent or medicament.

Various clinical conditions can be treated with the bioactive agents according to the present invention. One example is a skin disease or skin conditions such as psoriasis or eczema.

Accordingly, the present invention relates is one aspect to a method of treatment of one or more skin diseases such as psoriases comprising the step of
i) applying a composition according to the invention to the skin of an individual in need there of
and thereby treating said skin disease such as said psoriasis.

In one embodiment the one or more skin diseases or skin conditions can be selected from the group consisting of Acne, Actinic Keratosis, Alopecia Areata, Athlete's Foot, Atopic Dermatitis, Bed Bugs, Birthmarks and Other Skin Pigmentation Problems, Boils, Bruises, Bug Bites and Stings, Burns, Cellulitis, Chiggers (Bites), Corns, Cuts, Scrapes and Puncture Wounds, Cysts, Diaper Rash, Dry Skin, Eczema, Erythema Nodosum, Folliculitis, Freckles, Frostbite, Fungal Nails, Hair Loss, Heat Rash, Hematoma, Herpes Simplex Infections (Non-Genital), Hives, Hyperhidrosis, Ingrown Hair, Ingrown Toenail, Itch, Jock Itch, Keloid, Keratosis Pilaris, Lichen Planus, Lichen Sclerosus, Melasma, Moles, Molluscum Contagiosum, Pilonidal Cyst, Pityriasis Rosea, Poison Ivy, Psoriasis, Psoriatic Arthritis, Rash, Rhinoplasty, Ringworm, Rosacea, Rothmund-Thomson Syndrome, Scabies, Scalp Psoriasis, Scars, Seborrhea, Seborrheic Dermatitis, Shingles, Shingles and Pregnancy, Skin Cancer, Skin Tag, Spider Bites (Black Widow and Brown Recluse), Stretch Marks, Photosensitivity to Drugs, Sunburn and Sun Poisoning, Sweating (Perspiration), Tinea Versicolor, Varicose Veins, Vitiligo, Warts (Common Warts), Weber-Christian Disease, and Wrinkles.

Psoriasis

The present invention relates in one embodiment to treatment of any type of psoriasis including but not limited to Plaque-Type Psoriasis, Guttate Psoriasis, Pustular Psoriasis, Inverse Psoriasis, Erythrodermic Psoriasis, Nail Psoriasis, Psoriasis of the Scalp, and Psoriatic Arthritis.

In another embodiment the invention relates to treatment of selected types of psoriasis including but not limited to Plaque-Type Psoriasis, Guttate Psoriasis, Pustular Psoriasis, Inverse Psoriasis, Erythrodermic Psoriasis, Nail Psoriasis, Psoriasis of the Scalp, and Psoriatic Arthritis.

Psoriasis is a skin disease, often marked by red scaly patches. There are several different types of psoriasis. In most cases, people have one type at a time. Sometimes symptoms go away. Then, another type of psoriasis crops up in response to a trigger. Here is a brief overview of the main types of psoriasis that can be treated according to the present invention. The present invention relates to treatment of any or all or the types of psoriasis mentioned herein below.

Plaque Psoriasis

Plaque psoriasis is the most common type of psoriasis. About eight in 10 people with psoriasis have this type. It is also sometimes known as psoriasis vulgaris. Plaque psoriasis causes raised, inflamed, red skin covered by silvery white scales. These may also itch or burn. Plaque psoriasis can appear anywhere on your body but often appears in these areas: Elbows, Knees, Scalp, and Lower back. Rather than coming and going, plaque psoriasis may last for years.

Guttate Psoriasis

Guttate psoriasis often starts suddenly in childhood or young adulthood. It occurs is less than 2% of cases. This type causes small, pink-red spots on the skin. Usually less thick than plaque lesions, they often appear in these areas: Trunk, Upper arms, Thighs, and Scalp. These things may trigger guttate psoriasis: An upper respiratory infection such as strep throat or tonsillitis, Stress, Skin injury, and Certain drugs such as beta-blockers. This type of psoriasis may go away within a few weeks, even without treatment. However, some cases are more stubborn and require treatment.

Inverse Psoriasis

Inverse psoriasis appears as bright-red, smooth, shiny lesions. These don't have scales. Inverse psoriasis usually appears in these areas: in the armpits, in the groin, under the breasts, and in skin folds around the genitals or buttocks. Because of its location, inverse psoriasis may worsen from sweating and rubbing. For this reason, it can be hard on overweight people or those with deep skin folds. An overgrowth of yeast may trigger this type of psoriasis.

Pustular Psoriasis

Pustular psoriasis is uncommon and mostly appears in adults. Pustular psoriasis causes pus-filled bumps (pustules) surrounded by red skin. These may look infectious, but they are not. Reddening can appear first, followed by scaling and the formation of the pus-filled bumps.

This type of psoriasis may show up in one area of the body such as the hands and feet. Or it may cover most of the body (generalized). Pustular psoriasis can be very serious, so immediate medical attention is needed. Generalized pustular psoriasis can cause: Fever, Chills, Nausea, Fast heart rate, and Muscle weakness. These things may trigger pustular psoriasis: Topical or systemic medications, especially steroids, Sudden withdrawal of systemic medications or strong topical steroids, Overexposure to ultraviolet (UV) light, Pregnancy, Infection, Stress, and Exposure to certain chemicals.

Erythrodermic Psoriasis

This type of psoriasis is the least common, but it's very serious. Eyrthrodermic psoriasis affects most of the body and causes widespread, fiery skin redness that may appear burned. In addition, the patient may have: Severe itching, burning, or peeling, An increase in heart rate and Changing body temperature. This type of psoriasis can cause severe illness from protein and fluid loss. The patient may also develop an infection, pneumonia, or congestive heart failure. These things may trigger erythrodermic psoriasis: Sudden withdrawal from a systemic psoriasis treatment, An allergic drug reaction, Severe sunburn, Infection, and Medications such as lithium, anti-malarial drugs, cortisone, or strong coal tar products. Erythrodermic psoriasis may also occur if the patient has a long period where it is hard to control the psoriasis.

Nail Psoriasis

Up to half of those with psoriasis have nail changes. This is even more common in those who have a type of psoriasis that affects the joints (psoriatic arthritis).

These are common symptoms of nail psoriasis: Shallow or deep holes, Changes in nail shape, Thickening, Separation of the nail from the bed and Unusual color of the nails. With nail psoriasis, the patients are more likely to also have a fungal infection.

Psoriatic Arthritis

This is a condition where the patient has both psoriasis and arthritis (joint inflammation). In 70% of cases, people have psoriasis for about 10 years before developing psoriatic arthritis. About 90% of people with psoriatic arthritis will also have nail changes related to psoriasis. The most common joint symptoms of psoriatic arthritis are: Painful and stiff joints that are worse in the morning and after rest, Sausage like swelling of the fingers and toes, and Warm joints that may be discolored.

Psoriasis is a chronic relapsing disease of the skin that may be classified into nonpustular and pustular types as follows:

A) Nonpustular

Psoriasis vulgaris (chronic stationary psoriasis, plaque-like psoriasis). It affects 80 to 90% of people with psoriasis. Plaque psoriasis typically appears as raised areas of inflamed skin covered with silvery white scaly skin. These areas are called plaques.

Psoriatic erythroderma (erythrodermic psoriasis) involves the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. This form of psoriasis can be fatal, as the extreme inflammation and exfoliation disrupt the body's ability to regulate temperature and for the skin to perform barrier functions.

B) Pustular

Pustular psoriasis appears as raised bumps that are filled with noninfectious pus (pustules). The skin under and surrounding the pustules is red and tender. Pustular psoriasis can be localised, commonly to the hands and feet (palmoplantar pustulosis), or generalised with widespread patches occurring randomly on any part of the body. Types include:

Generalized pustular psoriasis (pustular psoriasis of von Zumbusch)

Pustulosis palmaris et plantaris (persistent palmoplantar pustulosis, pustular psoriasis of the Barber type, pustular psoriasis of the extremities)

Annular pustular psoriasis

Acrodermatitis continua

Impetigo herpetiformis

C) Other Types of Psoriasis

Additional types of psoriasis include:

Drug-induced psoriasis

Inverse psoriasis (flexural psoriasis, inverse psoriasis) appears as smooth inflamed patches of skin. It occurs in skin folds, particularly around the genitals (between the thigh and groin), the armpits, under an overweight abdomen (panniculus), and under the breasts (inframammary fold). It is aggravated by friction and sweat, and is vulnerable to fungal infections.

Napkin psoriasis

Seborrheic-like psoriasis

Guttate psoriasis is characterized by numerous small, scaly, red or pink, teardrop-shaped lesions. These numerous spots of psoriasis appear over large areas of the body, primarily the trunk, but also the limbs and scalp. Guttate psoriasis is often preceded by a streptococcal infection, typically streptococcal pharyngitis. The reverse is not true.

Nail psoriasis produces a variety of changes in the appearance of finger and toe nails. These changes include discolouring under the nail plate, pitting of the nails, lines going across the nails, thickening of the skin under the nail, and the loosening (onycholysis) and crumbling of the nail.

Psoriatic arthritis involves joint and connective tissue inflammation. Psoriatic arthritis can affect any joint, but is most common in the joints of the fingers and toes. This can result in a sausage-shaped swelling of the fingers and toes known as dactylitis. Psoriatic arthritis can also affect the hips, knees and spine (spondylitis).

The migratory stomatitis in the oral cavity mucosa and the geographic tongue that confined to the dorsal and lateral aspects of the tongue mucosa, are believed to be oral manifestations of psoriasis, as being histologically identical to cutaneous psoriasis lesions and more prevalent among psoriasis patients, although these conditions are quite common in the non-psoriatic population, affecting 1% to 2.5% of the general population.

One or more of the above listed types of psoriasis can be treated with the bioactive agent according to the present invention.

Eczema

Eczema, also called "dermatitis," is not one specific skin condition. Several types of eczema exist, and sometimes a person develops more than one type.

The present invention relates in one embodiment to treatment of any type of eczema including but not limited to Atopic dermatitis, Contact dermatitis, Dyshidrotic dermatitis, Hand dermatitis, Neurodermatitis, Nummular dermatitis, Occupational dermatitis, Seborrheic dermatitis and Stasis dermatitis.

In another embodiment the invention relates to treatment of selected types of eczema including but not limited to Atopic dermatitis, Contact dermatitis, Dyshidrotic dermatitis, Hand dermatitis, Neurodermatitis, Nummular dermatitis, Occupational dermatitis, Seborrheic dermatitis and Stasis dermatitis.

Atopic Dermatitis

Also known as "eczema", atopic dermatitis is a chronic (long-lasting) skin condition. It causes dry, itchy, irritated skin that can require daily care. Most people (90%) develop atopic dermatitis before age 5. This skin condition tends to run in families. People who get atopic dermatitis usually have family members who have eczema, asthma, or hay fever. Other Names include Eczema (Atopic dermatitis is often called "eczema."), Dermatitis and Atopic eczema.

Atopic dermatitis can be treated with the bioactive compound according to the present invention e.g. in combination with one or more of the following treatments:

While atopic dermatitis cannot be cured, most cases can be controlled with proper treatment. The goals of treatment are to hydrate the skin, reduce inflammation, decrease the risk of infection, and alleviate the itchy rash.

Signs and symptoms may be treated with:
  Emollients to help relieve dry skin
  Cold compresses applied directly to the skin to help relieve the itch
  Corticosteroids to help reduce inflammation; topical tacrolimus and pimecrolimus also may be used to reduce inflammation
  Antibiotics to treat a bacterial infection
  Sedative antihistamines to help the patient get a good night's sleep
  Phototherapy can help relieve moderate to severe cases
Effective treatment often requires a multifaceted treatment plan that includes medication, proper skin care, trigger avoidance, and coping mechanisms. While doing all of this may seem bothersome, adhering to a treatment plan can help the patient feel better and stop the atopic dermatitis from getting worse.
Despite the advertised claims, studies have not shown the following food supplements to be helpful—evening primrose oil, borage oil, zinc, B6 (pyridoxine), and vitamin E.
While atopic dermatitis may resolve without treatment in children, this does not tend to occur in adults.

Contact Dermatitis

Contact with everyday objects—from shampoo and jewelry to food—causes this very common type of eczema. When the contact leads to irritated skin, the eczema is called irritant contact dermatitis. If an allergic reaction develops on the skin after exposure, the eczema is called allergic contact dermatitis.

Contact dermatitis can be treated with the bioactive compound according to the present invention e.g. in combination with one or more of the following treatments:
  Avoiding the substance(s) causing the irritation or allergy. The patient must avoid the cause. Avoiding all substances that can trigger a flare-up can be difficult—if not impossible—when the person encounters these substances in the workplace. Dermatologists usually help their patients develop a strategy to circumvent exposure. This may include using a barrier cream, wearing gloves, and practicing glove hygiene.
  Therapy to help clear the skin. Treatment may include applying emollients and moisturizers frequently throughout the day, taking an oral antihistamine to help stop the itch, and applying a topical corticosteroid or calcineurin inhibitor to reduce inflammation. In more severe cases, phototherapy treatments may be used to suppress the person's overactive immune response. If an infection develops, antibiotics are necessary.
  If contact dermatitis persists despite treatment, oral or injectable corticosteroids can be used for a short time to get the inflammation under control.

Dyshidrotic Dermatitis

Occurring only on the palms of the hands, sides of the fingers, and soles of the feet, this common eczema typically causes a burning or itching sensation and a blistering rash. Some patients say the blisters resemble tapioca pudding. Other Names: Hand eczema, Pompholyx, Vesicular eczema and Vesicular palmoplantar eczema.

Dyshidrotic dermatitis can be treated with the bioactive compound according to the present invention e.g. in combination with one or more of the following treatments:
  Medications
  Topical corticosteroid and cold compresses are typically used first.
  Dermatologists may drain large blisters to relieve pain.
  Prescription antibiotics are used to treat an infection.
  Topical medication, such as pramoxine, can help relieve pain and itch.
  For severe cases that seem resistant to treatment, dermatologists may prescribe an oral corticosteroid or another immunosuppressive medication (e.g., methotrexate, cyclosporine, or mycophenolate mofetil) along with bedrest.
  PUVA therapy (a type of light treatment) helps some patients with chronic dyshidrotic dermatitis.
  Topical calcineurin inhibitors (e.g., pimecrolimus and tacrolimus), which are used to treat atopic dermatitis, can effectively reduce inflammation.
  Injections of botulinum toxin type A, a popular wrinkle treatment, have effectively cleared some patients. While the reason remains unclear, it is believed that the botulinum toxin type A may relax the muscles or inhibit nerve impulses.
  Lifestyle Changes
  Reduce stress. Some patients find that practicing stress-reduction techniques along with using medication as directed helps to clear their skin. For information about stress-reduction techniques that can help patients with eczema.

Avoid allergens and irritants. A medical test called "patch testing" can identify common substances to which the person is allergic. Patch testing cannot identify irritants; however, a dermatologist can ask a number of questions to help identify anything that is irritating the skin. Avoiding known allergens and irritants can help reduce flare-ups.

Follow a dermatologist-recommended skin care plan. Dermatologists often recommend that patients follow a recommended skin care plan. This can help prevent flare-ups.

Avoid excessive sweating and dry conditions. Both are believed to be triggers.

Protect the skin from further injury. Using gloves to protect the hands from irritants and allergens, wearing socks e.g. made of cotton, and avoiding strong soaps can help protect damaged skin.

Hand Dermatitis

Hand dermatitis is not one specific type of eczema as is atopic dermatitis or seborrheic dermatitis. Any type of eczema that develops on the hands can be classified as "hand dermatitis." Why this special classification? Hand dermatitis often has unique causes—frequently job-related—and can require special treatment considerations. Other Names: Hand eczema.

Hand dermatitis can be treated with the bioactive compound according to the present invention e.g. in combination with one or more of the following treatments:

Medication

Topical corticosteroids and tars. These medications help reduce inflammation. Available in various strengths ranging from mild to very potent, these medications should be used as instructed. Applying larger amounts or more often than directed can cause unwanted side effects, including thinning skin.

Topical calcineurin inhibitors. An alternative to topical corticosteroids, these medications also treat inflammation. Pimecrolimus, one type of topical calcineurin inhibitor, has relieved chronic hand dermatitis in some patients.

Antibiotics. A topical or oral antibiotic may be prescribed to clear an infection in the skin.

Botulinum toxin type A. Studies show that patients whose hands perspire excessively may get relief with periodic injections of this popular cosmetic treatment.

Phototherapy. A type of light therapy called PUVA, which combines a medication called psorlen with UVA light treatment, can help clear chronic hand dermatitis.

Oral corticosteroid, cyclosporine, methotrexate, and mycophenolate mofetil. These medications suppress the body's immune system and may be prescribed if other treatments have not effectively cleared a severe case of hand dermatitis.

Prevention

Apply emollients and moisturizers. These products help soften the skin and lock in moisture. For best results, these should be applied after bathing and frequently throughout the day.

Avoid allergens. If the results of the patch testing indicate an allergy, the patient should avoid all items that contain the allergen (substance causing the allergy). For example, if the patch test shows an allergy to nickel, the patient should avoid wearing costume jewelry and eating foods that contain nickel, such as tomatoes and canned foods. Some allergens are so common that it is best to ask a dermatologist for a list of products that contain the allergen.

Avoid irritants. After asking some questions, a dermatologist often can determine if an irritant is causing the reaction. If this is the case, the dermatologist will talk about options for avoiding the substance(s) that is irritating the skin.

Change work habits. A few days away from the job may clear a mild case. Changing a few habits can help keep the skin clear. For example, if the patient wears gloves at work, it is important to realize that substances on the hands can get inside the gloves and irritate the skin, especially when more than one substance gets inside the gloves.

Switch gloves. Sometimes a material used to make the gloves causes hand dermatitis. For example, some medical professionals develop raw, inflamed hands after wearing latex gloves. Switching to a glove that does not contain latex usually brings relief. A dermatologist can help a patient find alternative gloves by accessing a database that lists hundreds of gloves and alternatives that offer the same protection.

Neurodermatitis

This common eczema develops when nerve endings in the skin become irritated, triggering a severe itch-scratch-itch cycle. Common causes of nerve irritation include an insect bite and emotional stress.

Neurodermatitis can be treated with the bioactive compound according to the present invention e.g. in combination with one or more of the following treatments:

Topical corticosteroid. A mainstay of treatment, this medication helps reduce inflammation and itch. It is important to apply all corticosteroids as directed to get the full benefit and reduce the risk of side effects.

Topical antibiotic. When the skin is broken, this helps to prevent infection and to treat a mild infection.

Oral antibiotic. This helps clear a skin infection.

Topical keratolytic. This helps reduce thick skin. A preparation containing urea, salicylic acid, or lactic acid may be used.

Sedative or tranquilizer. In some cases, this can be helpful in reducing anxiety and help the patient to get restorative sleep.

Nummular Dermatitis

Often appearing after a skin injury, such as a burn, abrasion, or insect bite, the hallmark of this common eczema is unique, coin-shaped (nummular) or oval lesions. One or many patches can develop that may last for weeks or months. Other names: Discoid eczema, Nummular eczema and Nummular eczematous dermatitis.

Nummular dermatitis can be treated with the bioactive compound according to the present invention e.g. in combination with one or more of the following treatments:

Protecting the skin from further injury.

Hydrating the skin. Taking a short, lukewarm bath or shower once a day and immediately applying a cream or ointment to still-damp skin can help hydrate dry skin as well as relieve the itch and scaling. Adding a bath oil to the water also may help.

Using medication as directed. Topical corticosteroids and tar preparations help reduce inflammation and itch. If a bacterial skin infection develops, it is treated with an antibiotic. An antihistamine can help a patient sleep.

When a patient develops severe or generalized (widespread lesions) nummular dermatitis, treatment may require special dressings, phototherapy (treatment with ultraviolet light), oral antibiotics, systemic (taken by mouth or injected) corticosteroids, and bed rest in a cool, moist environment.

To prevent nummular dermatitis from recurring once the skin clears, dermatologists recommend:
  Moisturizing. Applying a moisturizer at least daily, and after bathing helps, especially in a dry climate. Moisturizer helps trap water in the skin. A dermatologist can recommend suitable products that will not irritate the skin.
  Avoiding certain activities. Anything that dries, heats, or irritates the skin, such as hot baths, frequent bathing, or sitting next to a fire, can cause a flare-up.
  Modifying skin care. Using only a mild, non-drying cleanser (not soap) when bathing helps.
  Using a humidifier. When heating or air-conditioning is necessary, use a humidifier to add moisture to the air.
  Dressing for success. Wear loose clothing, and avoid wearing rough fabrics, such as wool, which can irritate the skin.

Occupational Dermatitis

Occupational dermatitis is not one specific type of eczema. It is any type of eczema caused by a person's workplace. This distinct classification came about because occupational dermatitis has unique causes and a large number of people develop eczema on the job. Other Names: Occupational eczema Occupational dermatitis can be treated with the bioactive compound according to the present invention e.g. in combination with one or more of the following treatments:
  Avoiding the substance(s) causing the irritation or allergy. The patient must avoid the cause. Avoiding all substances that can trigger a flare-up can be difficult—if not impossible—when the person encounters these substances at work. Dermatologists can help their patients develop an effective "avoidance" strategy. This may include using a barrier cream and wearing gloves or doing some tasks differently. Sometimes changes also are needed at home. The condition can be worsened by direct exposure to things around the home, such as soaps and detergents.
  Treatment to help clear the skin. Treatment may include applying emollients and moisturizers frequently throughout the day, using a topical anti-itch product, taking an oral antihistamine to help stop the itch, and applying a topical corticosteroid or calcineurin inhibitor to reduce inflammation. In more severe cases, phototherapy treatments may be used to suppress the person's overactive immune response. If an infection develops, antibiotics are necessary.
    If contact dermatitis persists despite treatment, oral or injectable corticosteroids can be used for a short time to get the inflammation under control.
  Following a skin care program. The dermatologist may recommend a skin care program. Following this program can help prevent the condition from getting worse and prevent future outbreaks.

Seborrheic Dermatitis

Usually beginning on the scalp as oily, waxy patches, this common type of eczema sometimes spreads to the face and beyond. A severe case, while rare, produces widespread lesions. Like most types of eczema, seborrheic dermatitis tends to flare in cold, dry weather. Other Names: Seborrheic eczema, Cradle cap (occurs in infants aged 0 to 6 months), Dandruff and Seborrhea.

Seborrheic dermatitis can be treated with the bioactive compound according to the present invention e.g. in combination with one or more of the following treatments:
  Infants (scalp). Cradle cap, which only develops in infants, can usually be controlled by shampooing more frequently with a baby shampoo and by softly brushing away the scales. A dermatologist also may prescribe a mild corticosteroid or anti-fungal medication.
  Infants (beyond the scalp). When the condition spreads beyond the scalp in infants, dermatologists usually prescribe a topical medication, such as a mild corticosteroid or anti-fungal cream.
  Adolescents and adults (scalp). African-American patients often get relief by shampooing once a week with a product recommended by a dermatologist.
    Caucasian patients with seborrheic dermatitis may find that shampooing more frequently than usual and leaving the lather on the scalp for a longer time clears the condition. Shampoos specially formulated for dandruff relief are often effective. Sometimes getting results requires alternating dandruff shampoos so that a different shampoo is used every few days. A dermatologist can explain this process and recommend which shampoos a patient should use and when. To effectively treat the scalp, a dermatologist also may prescribe a topical corticosteroid or anti-fungal medication.
    A word of caution: While tar shampoos can effectively reduce skin cell buildup, they also tend to discolor blond and gray hair.
  Adolescents and adults (beyond the scalp). Medicated dandruff shampoos often provide relief beyond the scalp. A dermatologist can explain how to use shampoo to treat other affected areas. A topical corticosteroid or antifungal medication also may be prescribed. A severe case may require the addition of an oral antifungal medication or phototherapy.

Stasis Dermatitis

Developing in the lower legs, this common eczema occurs when circulation becomes sluggish. Poor blood flow causes fluids to build up, and the legs swell. Over time, this build up of fluids affects the skin, causing a rash that usually itches, painful sores, as well as thinning and discolored skin. Effective treatment involves treating not only the dermatitis but the circulatory problem as well. Other Names: Gravitational dermatitis, Venous eczema and Venous stasis dermatitis.

Stasis dermatitis can be treated with the bioactive compound according to the present invention e.g. in combination with one or more of the following treatments:
  Elevating the legs above the heart. When sitting and sleeping, this can improve circulation in the legs and decrease swelling.
  Wearing a compression stocking while awake. Sometimes compression boots are prescribed. Both the stockings and the boots can improve circulation.
  Treating congestive heart failure. Treatment may involve taking a low-dose diuretic to treat congestive heart failure or high blood pressure.
  Applying a low-dose topical steroid. This can reduce inflammation.
  Applying a topical antibiotic. This is necessary if the skin becomes infected.
  Avoiding scratching. This is necessary to clear the skin.
  Taking an oral antibiotic if cellulitis develops. An oral antibiotic can help heal open sores and prevent tissue damage.
  Following wound-care instructions.
  Getting the recommended bedrest. Sometimes strict bedrest is necessary.

Once the signs and symptoms have cleared, the patient may require lifelong preventive maintenance that includes:

Taking regular walks
Not standing for long periods
Elevating the legs when sitting or sleeping
Wearing compression stockings while awake
Moisturizing the legs regularly, usually with petroleum jelly Co-Administration with One or More Other Skin Medications In one embodiment the bioactive agent according to the present is co-administered to an individual in need there of with one or more other psoriasis medicaments/treatments such as one or more psoriasis medicaments/treatments listed herein below.

A) Topical Agents

Bath solutions (epsom salt) and moisturizers, mineral oil, and petroleum jelly may help soothe affected skin and reduce the dryness which accompanies the build-up of skin on psoriatic plaques. Medicated creams and ointments applied directly to psoriatic plaques can help reduce inflammation, remove built-up scale, reduce skin turn over, and clear affected skin of plaques. Ointment and creams containing coal tar, dithranol (anthralin), corticosteroids like desoximetasone (Topicort), fluocinonide, vitamin $D_3$ analogues (for example, calcipotriol), and retinoids are routinely used. Activated vitamin D and its analogues can inhibit skin cell proliferation.

B) Phototherapy

Phototherapy in the form of sunlight has long been used effectively for treatment for psoriasis. Wavelengths of 311-313 nm are most effective and special lamps have been developed for this application. The exposure time should be controlled to avoid over exposure and burning of the skin. The UVB lamps should have a timer that will turn off the lamp when the time ends. The amount of light used is determined by a person's skin type.

Psoralen and ultraviolet A phototherapy (PUVA) combines the oral or topical administration of psoralen with exposure to ultraviolet A (UVA) light. The mechanism of action of PUVA is unknown, but probably involves activation of psoralen by UVA light, which inhibits the abnormally rapid production of the cells in psoriatic skin. There are multiple mechanisms of action associated with PUVA, including effects on the skin immune system.

C) Systemic Agents

Psoriasis that is resistant to topical treatment and phototherapy can be treated by medications taken internally by pill or injection (systemic). Patients undergoing systemic treatment are required to have regular blood and liver function tests because of the toxicity of the medication.

The three main traditional systemic treatments of psoriasis are methotrexate, cyclosporine and retinoids. Methotrexate and cyclosporine are immunosuppressant drugs; retinoids are synthetic forms of vitamin A. Patients taking methotrexate are prone to ulcerations. Methotrexate exposure may contribute to post-surgical events.

Biologics are manufactured proteins that interrupt the immune process involved in psoriasis. Unlike generalised immunosuppressant therapies such as methotrexate, biologics focus on specific aspects of the immune function leading to psoriasis. These drugs (interleukin antagonists) are relatively new, and their long-term impact on immune function is unknown, but they have proven effective in treating psoriasis and psoriatic arthritis.

Two psoriasis drugs that target T cells are efalizumab and alefacept. Efalizumab is a monoclonal antibody which blocks the molecules that dendritic cells use to communicate with T cells. It also blocks the adhesion molecules on the endothelial cells that line blood vessels, which attract T cells. However, it suppressed the immune system's ability to control normally harmless viruses, which led to fatal brain infections.

Several monoclonal antibodies (MAbs) target cytokines, the molecules that cells use to send inflammatory signals to each other. TNF-α is one of the main executor inflammatory cytokines. Four MAbs (infliximab, adalimumab, golimumab and certolizumab pegol) and one recombinant TNF-α decoy receptor, etanercept, have been developed against TNF-α to inhibit TNF-α signaling. Additional monoclonal antibodies have been developed against pro-inflammatory cytokines IL-12/IL-23 and Interleukin-17 and inhibit the inflammatory pathway at a different point than the anti-TNF-α antibodies. IL-12 and IL-23 share a common domain, p40, which is the target of the recently FDA-approved ustekinumab. Ustekinumab (IL-12/IL-23 blocker) was shown to have higher efficacy than high-dose etanercept over a 12-week period in patients with psoriasis.

In 2008, the FDA approved three new treatment options available to psoriasis patients: 1) Taclonex Scalp, a new topical ointment for treating scalp psoriasis; 2) the Xtrac Velocity excimer laser system, which emits a high-intensity beam of ultraviolet light, can treat moderate to severe psoriasis; and 3) the biologic drug adalimumab (brand name Humira) was also approved to treat moderate to severe psoriasis. Adalimumab had already been approved to treat psoriatic arthritis. The most recent biologic drug that has been approved to treat moderate to severe psoriasis is ustekinumab (brand name Stelara).

Medications with the least potential for adverse reactions are preferentially employed. If the treatment goal is not achieved, then therapies with greater potential toxicity may be used. Medications with significant toxicity are reserved for severe unresponsive psoriasis. This is called the psoriasis treatment ladder. As a first step, medicated ointments or creams, called topical treatments, are applied to the skin. If topical treatment fails to achieve the desired goal, then the next step would be to expose the skin to ultraviolet (UV) radiation. This type of treatment is called phototherapy. The third step involves the use of medications which are taken internally by pill or injection. This approach is called systemic treatment.

D) Alternative Therapy

Some studies suggest psoriasis symptoms can be relieved by changes in diet and lifestyle. Fasting periods, low energy diets and vegetarian diets have improved psoriasis symptoms in some studies, and diets supplemented with fish oil (in this study cod liver oil) have also shown beneficial effects. Fish oils are rich in the two omega-3 fatty acids eicosapentaenoic acid (EPA) and docosahexaenoic acid (DHA) and contain Vitamin E, furthermore cod liver oil contains Vitamin A and Vitamin D.

The severity of psoriasis symptoms may also be influenced by lifestyle habits related to alcohol, smoking, weight, sleep, stress and exercise.

It has been suggested that *cannabis* might treat psoriasis, due to the anti-inflammatory properties of its cannabinoids, and their regulatory effects on the immune system. The adverse effects of *cannabis* might be avoided with a topical preparation or by the use of (a) more specific endocannabinoid receptor agonist(s).

In one embodiment the bioactive agent according to the present is co-administered to an individual in need there of with one or more other psoriasis medicaments such as one or more psoriasis medicaments listed in the table herein below.

| Drug Name/generic name/class |
|---|
| 8-MOP; generic name: methoxsalen; class: psoralens
Aclovate; generic name: alclometasone; class: topical steroids
Acthar; generic name: corticotropin; class: corticotropin
Ala-Cort; generic name: hydrocortisone; class: topical steroids
Ala-Scalp; generic name: hydrocortisone; class: topical steroids
Ala-Scalp HP; generic name: hydrocortisone; class: topical steroids
Amevive; generic name: alefacept; class: selective immunosuppressants
Analpram E; generic name: hydrocortisone/pramoxine; class: anorectal preparations
Analpram-HC; generic name: hydrocortisone/pramoxine; class: anorectal preparations
Anthraforte; generic name: anthralin; class: topical antipsoriatics
Anthrascalp; generic name: anthralin; class: topical antipsoriatics
Anucort-HC; generic name: hydrocortisone; class: topical steroids
Anumed-HC; generic name: hydrocortisone; class: topical steroids
Apexicon; generic name: diflorasone; class: topical steroids
ApexiCon E; generic name: diflorasone; class: topical steroids
Aquanil HC; generic name: hydrocortisone; class: topical steroids
Aristocort A; generic name: triamcinolone; class: topical steroids
Aristocort For Injection; generic name: triamcinolone; class: glucocorticoids
Aristocort R; generic name: triamcinolone; class: topical steroids
Aristospan; generic name: triamcinolone; class: glucocorticoids
Balnetar; generic name: coal tar; class: miscellaneous topical agents
Beta HC; generic name: hydrocortisone; class: topical steroids
Betatar Gel; generic name: coal tar; class: miscellaneous topical agents
Calcitrene; generic name: calcipotriene; class: topical antipsoriatics
Caldecort; generic name: hydrocortisone; class: topical steroids
Carb-O-Lac HP; generic name: ammonium lactate/urea; class: topical emollients
Carb-O-Lac5; generic name: ammonium lactate/urea; class: topical emollients
Carmol HC; generic name: hydrocortisone; class: topical steroids
Carrington Oral Wound Rinse; generic name: aloe vera; class: herbal products, topical emollients
Cetacort; generic name: hydrocortisone; class: topical steroids
Cinolar; generic name: triamcinolone; class: topical steroids
Clinacort; generic name: triamcinolone; class: glucocorticoids
Clinalog; generic name: triamcinolone; class: glucocorticoids
Clobevate; generic name: clobetasol; class: topical steroids
Clobex; generic name: clobetasol; class: topical steroids
Cloderm; generic name: clocortolone; class: topical steroids
Cordran; generic name: flurandrenolide; class: topical steroids
Cordran SP; generic name: flurandrenolide; class: topical steroids
Cordran Tape; generic name: flurandrenolide; class: topical steroids
Cormax; generic name: clobetasol; class: topical steroids
Cortaid; generic name: hydrocortisone; class: topical steroids
Cortaid Intensive Therapy; generic name: hydrocortisone; class: topical steroids
Cortaid Maximum Strength; generic name: hydrocortisone; class: topical steroids
Cortaid with Aloe; generic name: hydrocortisone; class: topical steroids
Cortalo with Aloe; generic name: hydrocortisone; class: topical steroids
Corticaine; generic name: hydrocortisone; class: topical steroids
Cortizone for Kids; generic name: hydrocortisone; class: topical steroids
Cortizone-10; generic name: hydrocortisone; class: topical steroids
Cortizone-10; Anal Itch Cream; generic name: hydrocortisone; class: topical steroids
Cortizone-10 Intensive Healing Formula, generic name: hydrocortisone class: topical steroids
Cortizone-10 Plus; generic name: hydrocortisone; class: topical steroids
Cortizone-5; generic name: hydrocortisone; class: topical steroids
Cotacort; generic name: hydrocortisone; class: topical steroids
Cutar; generic name: coal tar; class: miscellaneous topical agents
Cyclocort; generic name: amcinonide; class: topical steroids
Delonide; generic name: desonide; class: topical steroids
Deltasone; generic name: prednisone; class: glucocorticoids
Denorex Therapeutic Protection; generic name: coal tar; class: miscellaneous topical agents
Dermarest Dricort; generic name: hydrocortisone; class: topical steroids
Dermarest Eczema Medicated; generic name: hydrocortisone; class: topical steroids
Dermarest Plus Anti-Itch; generic name: hydrocortisone; class: topical steroids
Dermatop; generic name: prednicarbate; class: topical steroids
Dermovate; generic name: clobetasol; class: topical steroids
Dermtex HC; generic name: hydrocortisone; class: topical steroids
Desonate; generic name: desonide; class: topical steroids
DesOwen; generic name: desonide; class: topical steroids
DHS Tar Shampoo; generic name: coal tar; class: miscellaneous topical agents
Doak Tar; generic name: coal tar; class: miscellaneous topical agents
Doak Tar Oil; generic name: coal tar; class: miscellaneous topical agents
Dovonex; generic name: calcipotriene; class: topical antipsoriatics
Dritho-Scalp; generic name: anthralin; class: topical antipsoriatics
Drithocreme; generic name: anthralin; class: topical antipsoriatics
Elocon; generic name: mometasone; class: topical steroids
Elta Tar; generic name: coal tar; class: miscellaneous topical agents
Embeline; generic name: clobetasol; class: topical steroids
Embeline E; generic name: clobetasol; class: topical steroids
Enbrel; generic name: etanercept; class: antirheumatics, TNF alfa inhibitors
Enzone; generic name: hydrocortisone/pramoxine; class: anorectal preparations
Epifoam; generic name: hydrocortisone/pramoxine; class: anorectal preparations |

-continued

| Drug Name/generic name/class |
|---|
| Estar; generic name: coal tar; class: miscellaneous topical agents
Florone; generic name: diflorasone; class: topical steroids
Fluocinonide-E; generic name: fluocinonide; class: topical steroids
Fototar; generic name: coal tar; class: miscellaneous topical agents
G-TAR; generic name: coal tar; class: miscellaneous topical agents
Genasone/Aloe; generic name: hydrocortisone; class: topical steroids
Gengraf; generic name: cyclosporine; class: calcineurin inhibitors
Gly-Cort; generic name: hydrocortisone; class: topical steroids
Gynecort Maximum Strength; generic name: hydrocortisone; class: topical steroids
H.P. Acthar Gel; generic name: corticotropin; class: corticotropin
Halog; generic name: halcinonide; class: topical steroids
Halog-E; generic name: halcinonide; class: topical steroids
Halonate; generic name: halobetasol; class: topical steroids
HC Pram; generic name: hydrocortisone/pramoxine; class: anorectal preparations
HC Pramoxine; generic name: hydrocortisone/pramoxine; class: anorectal preparations
Hemorrhoidal HC; generic name: hydrocortisone; class: topical steroids
Hemril-30; generic name: hydrocortisone; class: topical steroids
Hemril-HC Uniserts; generic name: hydrocortisone; class: topical steroids
Humira; generic name: adalimumab; class: antirheumatics, TNF alfa inhibitors
Hycort; generic name: hydrocortisone; class: topical steroids
Hydrocortisone 1% In Absorbase; generic name: hydrocortisone; class: topical steroids
Hydrocortisone with Aloe; generic name: hydrocortisone; class: topical steroids
Hydropram; generic name: hydrocortisone/pramoxine; class: anorectal preparations
Hytone; generic name: hydrocortisone; class: topical steroids
Instacort; generic name: hydrocortisone; class: topical steroids
Ionil T; generic name: coal tar; class: miscellaneous topical agents
Ionil T Plus; generic name: coal tar; class: miscellaneous topical agents
Itch-X Lotion; generic name: hydrocortisone; class: topical steroids
Ken-Jec 40; generic name: triamcinolone; class: glucocorticoids
Kenalog; generic name: triamcinolone; class: topical steroids
Kenalog-10; generic name: triamcinolone; class: glucocorticoids
Kenalog-40; generic name: triamcinolone; class: glucocorticoids
Kerasal Ultra 20; generic name: ammonium lactate/urea; class: topical emollients
Keratol HC; generic name: hydrocortisone; class: topical steroids
Lacticare-HC; generic name: hydrocortisone; class: topical steroids
Lidex; generic name: fluocinonide; class: topical steroids
Lidex-E; generic name: fluocinonide; class: topical steroids
Locoid; generic name: hydrocortisone class: topical steroids
Locoid Lipocream; generic name: hydrocortisone; class: topical steroids
LoKara; generic name: desonide; class: topical steroids
Massengill Medicated Soft Cloth; generic name: hydrocortisone; class: topical steroids
Maxiflor; generic name: diflorasone; class: topical steroids
MD Hydrocortisone; generic name: hydrocortisone; class: topical steroids
Medotar; generic name: coal tar; class: miscellaneous topical agents
Meticorten; generic name: prednisone; class: glucocorticoids
MG 217 Psoriasis; generic name: coal tar; class: miscellaneous topical agents
MG217 Medicated Tar; generic name: coal tar; class: miscellaneous topical agents
Neoral; generic name: cyclosporine; class: calcineurin inhibitors
Neutrogena T-Scalp; generic name: hydrocortisone; class: topical steroids
Neutrogena T/Derm; generic name: coal tar; class: miscellaneous topical agents
Neutrogena T/Gel; generic name: coal tar; class: miscellaneous topical agents
Neutrogena T/Gel Extra Strength; generic name: coal tar; class: miscellaneous topical agents
Novacort; generic name: hydrocortisone/pramoxine; class: anorectal preparations
NuCort with Aloe; generic name: hydrocortisone class: topical steroids
Nutracort; generic name: hydrocortisone; class: topical steroids
NuZon; generic name: hydrocortisone; class: topical steroids
Olux; generic name: clobetasol; class: topical steroids
Olux-E; generic name: clobetasol; class: topical steroids
Olux/Olux-E Kit; generic name: clobetasol; class: topical steroids
OraMagic Rx; generic name: aloe vera; class: herbal products, topical emollients
Oxipor VHC; generic name: coal tar; class: miscellaneous topical agents
Oxsoralen-Ultra; generic name: methoxsalen; class: psoralens
Pandel; generic name: hydrocortisone; class: topical steroids
PC Tar; generic name: coal tar; class: miscellaneous topical agents
Pediaderm HC; generic name: hydrocortisone; class: topical steroids
Pediaderm TA; generic name: triamcinolone; class: topical steroids
Pentrax; generic name: coal tar; class: miscellaneous topical agents
Pentrax Gold; generic name: coal tar; class: miscellaneous topical agents
Polytar; generic name: coal tar; class: miscellaneous topical agents
Pramosone; generic name: hydrocortisone/pramoxine; class: anorectal preparations
Pramosone E; generic name: hydrocortisone/pramoxine; class: anorectal preparations
Prednicot; generic name: prednisone; class: glucocorticoids
Procto-Kit 1%; generic name: hydrocortisone; class: topical steroids
Procto-Kit 2.5%; generic name: hydrocortisone; class: topical steroids
Procto-Pak 1%; generic name: hydrocortisone; class: topical steroids
ProctoCare-HC; generic name: hydrocortisone; class: topical steroids
Proctocort; generic name: hydrocortisone; class: topical steroids |

-continued

| Drug Name/generic name/class |
| --- |
| Proctocream-HC; generic name: hydrocortisone; class: topical steroids |
| Proctofoam HC; generic name: hydrocortisone/pramoxine; class: anorectal preparations |
| Proctosert HC; generic name: hydrocortisone; class: topical steroids |
| Proctosol-HC; generic name: hydrocortisone; class: topical steroids |
| Proctozone HC; generic name: hydrocortisone; class: topical steroids |
| Proctozone-H; generic name: hydrocortisone; class: topical steroids |
| Psorcon; generic name: diflorasone; class: topical steroids |
| Psorcon E; generic name: diflorasone; class: topical steroids |
| Psoriasin; generic name: coal tar; class: miscellaneous topical agents |
| Psoriatec; generic name: anthralin; class: topical antipsoriatics |
| Psorigel; generic name: coal tar; class: miscellaneous topical agents |
| R A Acne; generic name: resorcinol; class: topical antipsoriatics |
| Raptiva; generic name: efalizumab; class: selective immunosuppressants |
| Recort Plus; generic name: hydrocortisone; class: topical steroids |
| Rectasol-HC; generic name: hydrocortisone; class: topical steroids |
| Rectocort HC; generic name: hydrocortisone/pramoxine; class: anorectal preparations |
| Rederm; generic name: hydrocortisone; class: topical steroids |
| Remicade; generic name: infliximab; class: antirheumatics, TNF alfa inhibitors |
| Resinol; generic name: resorcinol; class: topical antipsoriatics |
| Sarnol-HC; generic name: hydrocortisone; class: topical steroids |
| Scalacort; generic name: hydrocortisone; class: topical steroids |
| Scalp-Cort; generic name: hydrocortisone; class: topical steroids |
| Scalpicin; generic name: hydrocortisone; class: topical steroids |
| Scytera; generic name: coal tar; class: miscellaneous topical agents |
| Soriatane; generic name: acitretin; class: antipsoriatics |
| Soriatane CK; generic name: acitretin; class: antipsoriatics |
| Sorilux; generic name: calcipotriene; class: topical antipsoriatics |
| Stelara; generic name: ustekinumab; class: interleukin inhibitors |
| Sterapred; generic name: prednisone; class: glucocorticoids |
| Sterapred DS; generic name: prednisone; class: glucocorticoids |
| TAC 3; generic name: triamcinolone; class: glucocorticoids |
| Taclonex; generic name: betamethasone/calcipotriene; class: topical antipsoriatics |
| Taclonex Scalp; generic name: betamethasone/calcipotriene; class: topical antipsoriatics |
| Tarsum; generic name: coal tar/salicylic acid; class: miscellaneous topical agents |
| Tazorac; generic name: tazarotene; class: topical antipsoriatics |
| Tegrin Medicated; generic name: coal tar; class: miscellaneous topical agents |
| Tegrin Medicated Soap; generic name: coal tar; class: miscellaneous topical agents |
| Temovate; generic name: clobetasol; class: topical steroids |
| Temovate E; generic name: clobetasol; class: topical steroids |
| Texacort; generic name: hydrocortisone; class: topical steroids |
| Therapeutic; generic name: coal tar; class: miscellaneous topical agents |
| Theraplex T; generic name: coal tar; class: miscellaneous topical agents |
| Topicort; generic name: desoximetasone; class: topical steroids |
| Topicort LP; generic name: desoximetasone; class: topical steroids |
| Trexall; generic name: methotrexate; class: antimetabolites, antipsoriatics, antirheumatics, other immunosuppressants |
| Triacet; generic name: triamcinolone; class: topical steroids |
| Triam-Forte; generic name: triamcinolone; class: glucocorticoids |
| Triamcot; generic name: triamcinolone; class: glucocorticoids |
| Triamonide 40; generic name: triamcinolone; class: glucocorticoids |
| Trianex; generic name: triamcinolone; class: topical steroids |
| Triderm; generic name: triamcinolone; class: topical steroids |
| Tridesilon; generic name: desonide; class: topical steroids |
| U-Cort; generic name: hydrocortisone; class: topical steroids |
| U-Tri-Lone; generic name: triamcinolone; class: glucocorticoids |
| Ultralytic; generic name: ammonium lactate/urea; class: topical emollients |
| Ultralytic 2; generic name: ammonium lactate/urea; class: topical emollients |
| Ultravate; generic name: halobetasol; class: topical steroids |
| Ultravate PAC; generic name: ammonium lactate/halobetasol; class: topical steroids |
| Ultravate Pack Ointment; generic name: ammonium lactate/halobetasol; class: topical steroids |
| Vanos; generic name: fluocinonide; class: topical steroids |
| Vectical; generic name: calcitriol; class: topical antipsoriatics |
| Verdeso; generic name: desonide; class: topical steroids |
| Westcort; generic name: hydrocortisone; class: topical steroids |
| X-Seb T Plus; generic name: coal tar/salicylic acid; class: miscellaneous topical agents |
| Z-Xtra; generic name: benzocaine/pyrilamine/zinc oxide |
| Zetar; generic name: coal tar; class: miscellaneous topical agents |
| Zithranol-RR; generic name: anthralin; class: topical antipsoriatics |
| Zone-A; generic name: hydrocortisone/pramoxine; class: anorectal preparations |
| Zone-A Forte; generic name: hydrocortisone/pramoxine; class: anorectal preparations |

In another embodiment the bioactive agent according to the present is co-administered to an individual in need there of with one or more other eczema medicaments such as one or more eczema medicaments selected from the table herein below.

| Drug Name/generic name/class |
|---|
| Aclovate; generic name: alclometasone; class: topical steroids |
| Ala-Cort; generic name: hydrocortisone; class: topical steroids |
| Ala-Quin; generic name: clioquinol/hydrocortisone; class: topical steroids with anti-infectives |
| Ala-Scalp; generic name: hydrocortisone; class: topical steroids |
| Ala-Scalp HP; generic name: hydrocortisone; class: topical steroids |
| Alcortin A; generic name: aloe vera/hydrocortisone/iodoquinol; class: topical steroids with anti-infectives |
| Aloquin; generic name: aloe polysaccharides/iodoquinol; class: topical anti-infectives |
| Anucort-HC; generic name: hydrocortisone; class: topical steroids |
| Anumed-HC; generic name: hydrocortisone class: topical steroids |
| Apexicon; generic name: diflorasone; class: topical steroids |
| ApexiCon E; generic name: diflorasone; class: topical steroids |
| Aquanil HC; generic name: hydrocortisone; class: topical steroids |
| Baycadron; generic name: dexamethasone; class: glucocorticoids |
| Beta HC; generic name: hydrocortisone; class: topical steroids |
| Caldecort; generic name: hydrocortisone; class: topical steroids |
| Carb-O-Lac HP; generic name: ammonium lactate/urea; class: topical emollients |
| Carb-O-Lac5; generic name: ammonium lactate/urea; class: topical emollients |
| Carmol HC; generic name: hydrocortisone; class: topical steroids |
| Carrington Oral Wound Rinse; generic name: aloe vera; class: herbal products, topical emollients |
| Cetacort; generic name: hydrocortisone; class: topical steroids |
| Cloderm; generic name: clocortolone; class: topical steroids |
| Cordran; generic name: flurandrenolide; class: topical steroids |
| Cordran SP; generic name: flurandrenolide; class: topical steroids |
| Cordran Tape; generic name: flurandrenolide; class: topical steroids |
| Cortaid; generic name: hydrocortisone; class: topical steroids |
| Cortaid Intensive Therapy; generic name: hydrocortisone; class: topical steroids |
| Cortaid Maximum Strength; generic name: hydrocortisone; class: topical steroids |
| Cortaid with Aloe; generic name: hydrocortisone; class: topical steroids |
| Cortalo with Aloe; generic name: hydrocortisone; class: topical steroids |
| Corticaine; generic name: hydrocortisone; class: topical steroids |
| Cortizone for Kids; generic name: hydrocortisone; class: topical steroids |
| Cortizone-10; generic name: hydrocortisone; class: topical steroids |
| Cortizone-10 Anal Itch Cream; generic name: hydrocortisone; class: topical steroids |
| Cortizone-10 Intensive Healing Formula; generic name: hydrocortisone; class: topical steroids |
| Cortizone-10 Plus; generic name: hydrocortisone; class: topical steroids |
| Cortizone-5; generic name: hydrocortisone; class: topical steroids |
| Cotacort; generic name: hydrocortisone; class: topical steroids |
| Cyclocort; generic name: amcinonide; class: topical steroids |
| De-Sone LA; generic name: dexamethasone; class: glucocorticoids |
| Decadron; generic name: dexamethasone; class: glucocorticoids |
| Delonide; generic name: desonide; class: topical steroids |
| Deltasone; generic name: prednisone; class: glucocorticoids |
| Dermarest Dricort; generic name: hydrocortisone; class: topical steroids |
| Dermarest Eczema Medicated; generic name: hydrocortisone; class: topical steroids |
| Dermarest Plus Anti-Itch; generic name: hydrocortisone; class: topical steroids |
| Dermatop; generic name: prednicarbate; class: topical steroids |
| Dermazene; generic name: hydrocortisone/iodoquinol; class: topical steroids with anti-infectives |
| DermOtic Oil; generic name: fluocinolone; class: otic steroids |
| Dermtex HC; generic name: hydrocortisone; class: topical steroids |
| Desonate; generic name: desonide; class: topical steroids |
| DesOwen; generic name: desonide; class: topical steroids |
| Dexacen-4; generic name: dexamethasone; class: glucocorticoids |
| Dexacort Phosphate in Turbinaire; generic name: dexamethasone; class: glucocorticoids |
| Dexamethasone Intensol; generic name: dexamethasone; class: glucocorticoids |
| Dexasone; generic name: dexamethasone; class: glucocorticoids |
| Dexasone LA; generic name: dexamethasone; class: glucocorticoids |
| Dexpak Taperpak; generic name: dexamethasone; class: glucocorticoids |
| Elidel; generic name: pimecrolimus; class: miscellaneous topical agents |
| Elocon; generic name: mometasone; class: topical steroids |
| Evening Primrose Oil; generic name: evening primrose; class: herbal products |
| Florone; generic name: diflorasone; class: topical steroids |
| Genasone/Aloe; generic name: hydrocortisone; class: topical steroids |
| Gly-Cort; generic name: hydrocortisone; class: topical steroids |
| Gynecort Maximum Strength; generic name: hydrocortisone; class: topical steroids |
| Halog; generic name: halcinonide; class: topical steroids |
| Halog-E; generic name: halcinonide; class: topical steroids |
| Halonate; generic name: halobetasol; class: topical steroids |
| Hemorrhoidal HC; generic name: hydrocortisone; class: topical steroids |
| Hemril-30; generic name: hydrocortisone; class: topical steroids |
| Hemril-HC Uniserts; generic name: hydrocortisone; class: topical steroids |
| Hycort; generic name: hydrocortisone; class: topical steroids |
| Hydrocortisone 1% In Absorbase; generic name: hydrocortisone; class: topical steroids |
| Hydrocortisone with Aloe; generic name: hydrocortisone; class: topical steroids |
| Hytone; generic name: hydrocortisone class: topical steroids |
| Instacort; generic name: hydrocortisone class: topical steroids |
| Itch-X Lotion; generic name: hydrocortisone; class: topical steroids |
| Kerasal Ultra 20; generic name: ammonium lactate/urea; class: topical emollients |
| Keratol HC; generic name: hydrocortisone; class: topical steroids |

| Drug Name/generic name/class |
| --- |
| Lacticare-HC; generic name: hydrocortisone; class: topical steroids |
| Locoid; generic name: hydrocortisone; class: topical steroids |
| Locoid Lipocream; generic name: hydrocortisone; class: topical steroids |
| LoKara; generic name: desonide; class: topical steroids |
| Massengill Medicated Soft Cloth; generic name: hydrocortisone; class: topical steroids |
| Maxiflor; generic name: diflorasone; class: topical steroids |
| MD Hydrocortisone; generic name: hydrocortisone; class: topical steroids |
| Meticorten; generic name: prednisone; class: glucocorticoids |
| Neutrogena T-Scalp; generic name: hydrocortisone; class: topical steroids |
| NuCort with Aloe; generic name: hydrocortisone; class: topical steroids |
| Nutracort; generic name: hydrocortisone; class: topical steroids |
| NuZon; generic name: hydrocortisone; class: topical steroids |
| OraMagic Rx; generic name: aloe vera; class: herbal products, topical emollients |
| Pandel; generic name: hydrocortisone; class: topical steroids |
| Pediaderm HC; generic name: hydrocortisone class: topical steroids |
| Prednicot; generic name: prednisone; class: glucocorticoids |
| Primrose Oil; generic name: evening primrose; class: herbal products |
| Procto-Kit 1%; generic name: hydrocortisone; class: topical steroids |
| Procto-Kit 2.5%; generic name: hydrocortisone; class: topical steroids |
| Procto-Pak 1%; generic name: hydrocortisone; class: topical steroids |
| ProctoCare-HC; generic name: hydrocortisone; class: topical steroids |
| Proctocort; generic name: hydrocortisone; class: topical steroids |
| Proctocream-HC; generic name: hydrocortisone; class: topical steroids |
| Proctosert HC; generic name: hydrocortisone; class: topical steroids |
| Proctosol-HC; generic name: hydrocortisone; class: topical steroids |
| Proctozone HC; generic name: hydrocortisone; class: topical steroids |
| Proctozone-H; generic name: hydrocortisone; class: topical steroids |
| Prudoxin; generic name: doxepin; class: topical antihistamines |
| Psorcon; generic name: diflorasone; class: topical steroids |
| Psorcon E; generic name: diflorasone; class: topical steroids |
| R A Acne; generic name: resorcinol; class: topical antipsoriatics |
| Recort Plus; generic name: hydrocortisone; class: topical steroids |
| Rectasol-HC; generic name: hydrocortisone; class: topical steroids |
| Rederm; generic name: hydrocortisone; class: topical steroids |
| Resinol; generic name: resorcinol; class: topical antipsoriatics |
| Sarnol-HC; generic name: hydrocortisone; class: topical steroids |
| Scalacort; generic name: hydrocortisone; class: topical steroids |
| Scalp-Cort; generic name: hydrocortisone; class: topical steroids |
| Scalpicin; generic name: hydrocortisone; class: topical steroids |
| Solurex; generic name: dexamethasone; class: glucocorticoids |
| Solurex LA; generic name: dexamethasone; class: glucocorticoids |
| Sterapred; generic name: prednisone; class: glucocorticoids |
| Sterapred DS; generic name: prednisone; class: glucocorticoids |
| Texacort; generic name: hydrocortisone; class: topical steroids |
| Topicort; generic name: desoximetasone; class: topical steroids |
| Topicort LP; generic name: desoximetasone; class: topical steroids |
| Trexall, generic name: methotrexate; class: antimetabolites, antipsoriatics, antirheumatics, other immunosuppressants |
| Tridesilon; generic name: desonide; class: topical steroids |
| U-Cort; generic name: hydrocortisone; class: topical steroids |
| Ultralytic; generic name: ammonium lactate/urea; class: topical emollients |
| Ultralytic 2; generic name: ammonium lactate/urea; class: topical emollients |
| Ultravate; generic name: halobetasol; class: topical steroids |
| Ultravate PAC; generic name: ammonium lactate/halobetasol; class: topical steroids |
| Ultravate Pack Ointment; generic name: ammonium lactate/halobetasol; class: topical steroids |
| Verdeso; generic name: desonide; class: topical steroids |
| Vytone; generic name: hydrocortisone/iodoquinol; class: topical steroids with anti-infectives |
| Westcort; generic name: hydrocortisone; class: topical steroids |
| Z-Xtra; generic name: benzocaine/pyrilamine/zinc oxide class: |
| Zema Pak; generic name: dexamethasone; class: glucocorticoids |
| Zonalon; generic name: doxepin; class: topical antihistamines |

In another embodiment the bioactive agent according to the present is co-administered to an individual in need there of with one or more other skin medicaments such as one or more skin medicaments selected from the group consisting of acitretin-oral (Soriatane), adapalene (Differin), alcohol acetone-topical (Seba-Nil), alefacept (Amevive), aminolevulinic acid solution applicator (Levulan), amoxicillin (Amoxil, Polymox, Trimox), amoxicillin and clavulanic acid (Augmentin), anthralin lotion (for scalp)-topical (Dritho-Scalp), anthralin topical (Psoriatec), azelaic acid cream-topical (Azelex), benzoyl peroxide-topical (Vanoxide, Zoderm, Triaz and more), betamethasone dipropionate (Diprolene, Diprosone, Diprolene AF and more), betamethasone-calcipotriol-topical (Taclonex), betamethasone-topical foam (Luxiq), calcipotriene-topical (Dovonex, Sorilux), capsaicin-topical (Capsagel, Salonpas-Hot, Zostrix), cephalexin (Keftabs, Keflex), chloroxine-shampoo (Capitrol), ciclopirox (Penlac, Loprox), clindamycin and benzoyl peroxide combination (Z-Clinz), clindamycin and benzoyl peroxide gel (Duac, Benzaclin, Acanya), clindamycin-topical (Cleocin T, Clinda-Derm), clioquinol-topical clobetasol foam-topical (Olux), clotrimazole (Lotrimin, Mycelex), clotrimazole and betamethasone dipropionate (Lotrisone), collagenase clostridium histolyticum (Xiaflex), corticosteroids-topical, desoximetasone-topical (Topicort, Topicort LP), doxycycline (Vibramycin), efalizumab (Raptiva), erythromycin and benzoyl peroxide (Benzamycin, benzoyl peroxide & erythromycin), etanercept (Enbrel), etretinate-oral (Tegison), famciclovir (Famvir), finasteride-oral (hair growth) (Propecia), fluocinolone-topical oil (Derma-Smoothe/FS), fluorouracil-topical-carac-efudex-fluoroplex (Carac, Efudex, Fluoroplex), fusidic acid/hydrocortisone-topical, griseofulvin-oral tablet (Fulvicin, Grifulvin V, Gris-Peg and more), halobetasol-topical (Ultravate), hyaluronic acid (Restylane-L, Restylane), hydrocortisone valerate (Westcort), hydrocortisone-benzoyl peroxide-topical (Vanoxide-HC), imiquimod-topical (Aldara), isoniazid, INH (INH, Laniazid, Nydrazid), isotretinoin (Accutane, Amnesteem, Claravis and more), itraconazole (Sporanox), ketoconazole (Extina, Kuric, Nizoral and more), lidocaine patch-topical (Lidoderm), lindane-topical lotion, meclocycline-topical (Meclan), methotrexate (Rheumatrex, Trexall), methoxsalen-oral, methoxsalen-topical (Oxsoralen), metronidazole cream (Noritate, Metrocream), minocycline-oral (Dynacin, Minocin), minoxidil (Rogaine), mometasone (Elocon), mupirocin (Bactroban, Bactroban Nasal, Centany), pimecrolimus (Elidel), pramoxine and benzyl alcohol (Anti-Itch, benzyl alcohol and pramoxine, Itch-X and more), pramoxine-hydrocortisone-cream, ointment (Enzone, Pramosone), pramoxine-hydrocortisone-lotion (Pramosone, Zone-A), sodium sulfacetamide lotion-topical (Klaron), sulfacetamide with sulfur topical lotion (Nicosyn, Novacet, Sulfacet-R), sulfacetamide with sulfur-topical (Plexion TS, Rosula, Zetacet), sulfacetamide with sulfur-topical cleanser (Avar, Plexion, Rosanil Cleanser and more), sulfacetamide with sulfur-topical cream (Plexion SCT), sulfacetamide with sulfur-topical gel (Avar), sulfur-alcohol-topical (Liquimat), tacrolimus ointment (Protopic), tazarotene-topical (Tazorac), tea tree oil-topical, terbinafine (Lamisil, Lamisil AT), thalidomide (Thalomide), tretinoin (Altinac, Atralin, Avita and more), triacetin-topical cream/solution, triacetin-topical spray, triacetin-topical tincture, ustekinumab (Stelara), valacyclovir (Valtrex), zinc oxide-topical (Desitin), and Zoster Vaccine Live (Shingles Vaccine) (Herpes Zoster Vaccine, Vaccine, Shingles, Zostavax and more).

The composition according to the present invention can also be used in combination with (either subsequently, or simultaneously) any of the psoriasis treatments/medicaments disclosed in the US patent application in the table herein below. All US patent application in the table herein below are incorporated in this application in their entirety.

| US application No | Title |
| --- | --- |
| 20130023501 | PHARMACEUTICAL COMPOSITION COMPRISING SOLVENT MIXTURE AND A VITAMIN D DERIVATIVE OR ANALOGUE |
| 20130005680 | PHARMACEUTICAL COMPOSITION COMPRISING VITAMIN D ANALOGUE AND COSOLVENT-SURFACTANT MIXTURE |
| 20120322776 | CUTANEOUS COMPOSITION COMPRISING VITAMIN D ANALOGUE AND A MIXTURE OF SOLVENT AND SURFACTANTS |
| 20120252815 | INHIBITORS OF SPHINGOSINE KINASE |
| 20120252789 | INHIBITORS OF SPHINGOSINE KINASE |
| 20120251545 | Therapeutic Combinations Of Hydroxybenzamide Derivatives As Inhibitors Of HSP90 |
| 20120178740 | HETEROCYCLIC COMPOUNDS AS JAK RECEPTOR AND PROTEIN TYROSINE KINASE INHIBITORS |
| 20120109042 | Methods of Treating Diseased Tissue |
| 20120028974 | TRIAZOLOPYRIDINES AS PHOSPHODIESTERASE INHIBITORS FOR TREATMENT OF DERMAL DISEASES |
| 20110257492 | METHOD FOR DETERMINING THE STATE OF A SKIN DISORDER USING NEAR INFRARED (NIR) SPECTROSCOPY |
| 20110190282 | NOVEL VEGF-2 RECEPTOR AND PROTEIN TYROSINE KINASE INHIBITORS AND PHARMACEUTICAL USE THEREOF |
| 20110166175 | 7-AZAINDOLE DERIVATIVES |
| 20110135600 | BICYCLIC TRAIZOLE DERIVATIVES FOR TREATING OF TUMORS |
| 20110104186 | Small molecule immunopotentiators and assays for their detection |
| 20110014135 | VITAMIN FORMULATION |
| 20100286167 | DIHYDROXYPHENYL ISOINDOLYLMETHANONES |
| 20100278784 | METHODS AND COMPOSITIONS FOR TREATING SKIN CONDITIONS |
| 20100240621 | TOPICAL PHARMACEUTICAL COMPOSITION FOR THE COMBINATION OF FUSIDIC ACID AND A CORTICOSTEROID |
| 20100216782 | HYDROXYBENZAMIDE DERIVATIVES AND THEIR USE AS INHIBITORS OF HSP90 |
| 20100203089 | SELECTIVE CHEMOKINE MODULATION |
| 20100122356 | PIG MODEL FOR PSORIASIS |
| 20100099688 | NOVEL PHOSPHODIESTERASE INHIBITORS |
| 20100035908 | SUBSTITUTED ACETOPHENONES USEFUL AS PDE4 INHIBITORS |
| 20090215772 | Hydroxybenzamide derivatives and their use as inhibitors of HSP90 |
| 20090131380 | Novel pharmaceutical composition for topical treatment of skin psoriasis and the treatment method thereof |
| 20080306054 | Pharmaceutical Compounds |
| 20080234239 | Topical composition |
| 20080044439 | Compositions and Methods for Preventing and Treating Skin and Hair Conditions |
| 20080038374 | New Use |
| 20080038353 | Polymer Based Nano-Carriers For The Solubilization And Delivery Of Hydrophobic Drugs |
| 20070276026 | Hydroxybenzamide Derivatives And Their Use As Inhibitors Of HSP90 |
| 20070259886 | DIHYDROXYPHENYL ISOINDOLYLMETHANONES |
| 20070259871 | Hydroxybenzamide Derivatives And Their Use As Inhibitors Of HSP90 |
| 20070255066 | Epimerisation of Allylic Alcohols |

| US application No | Title |
|---|---|
| 20070244117 | Novel Hydroxamic Acid Esters and Pharmaceutical Use Thereof |
| 20070215455 | Isomerisation of pharmaceutical intermediates |
| 20070167488 | Novel therapeutic use |
| 20070135395 | Novel method for the preparation of intermediates useful for the synthesis fo vitamin d analogues |
| 20070027333 | Stereoselective synthesis of vitamin d analogues |
| 20060292080 | VITAMIN FORMULATION |
| 20060166990 | Novel aminobenzophenone compounds |
| 20060166949 | Vitamin d analogues, compositions comprising said analogues and their use |
| 20060128766 | Triazole substituted aminobenzophenone compounds |
| 20060034779 | Foamable compositions containing vitamin D3 analogues, processes for preparing same and methods of treatment utilizng same |
| 20050203111 | Compositions and methods for preventing and treating skin and hair conditions |
| 20030036524 | Method of sensitising endothelial cells to prodrugs |

In another embodiment the composition according to the present invention can be used with SMIP and/or SMIS as defined in US20110104186 or other compounds mentioned in US20110104186 (which is hereby incorporated herein in its entirety).

The term "SMIP" refers to small molecule immunopotentiating compounds, including small molecule compounds below about MW 800 g/mol, capable of stimulating or modulating a pro-inflammatory response in a patient. In an embodiment, the SMIP compounds are able to stimulate human peripheral blood mononuclear cells to produce cytokines, chemokines, and/or growth factors.

The term "SMIS" refers to small molecule immunosuppressant compounds, including small molecule compounds below about MW 800 g/mol, capable of suppressing or modulating an immune response in a patient. In an embodiment, the SMIS compounds are able to inhibit human peripheral blood mononuclear cell's ability to produce cytokines, chemokines, and/or growth factors. In another embodiment, the SMIS compounds are able to stimulate TGF-beta, thereby suppressing an immune response. In some embodiments, compounds of interest in the instant invention are analogs thereof, or "SMIS analogs," which are meant to describe a derivative of a compound known generally in the art to suppress the immune system.

Pharmaceutical Compositions Comprising a Bioactive Agent Such as Beta Glucans

While it is possible for the bioactive agents useful in the present invention to be administered as obtained from liquid cultivation of a Basidiomycete cell, optionally in isolated and/or purified form, it is preferred in one embodiment according to the present invention to administer the bioactive agents as part of a pharmaceutical composition.

Pharmaceutical compositions according to the invention may comprise any Basidiomycete cell bioactive agent and one or more pharmaceutically acceptable carriers, vehicles and/or excipients. Said composition may further optionally comprise transport molecules. The transport molecules are primarily added in order to increase the half-life of the bioactive agent(s). Transport molecules act by having incorporated into or anchored to it the bioactive agent according to the invention.

Any suitable transport molecules known to the skilled person may be used, such as liposomes, micelles, and/or microspheres.

Liposomes

Conventional liposomes are typically composed of phospholipids (neutral or negatively charged) and/or cholesterol. The liposomes are vesicular structures based on lipid bilayers surrounding aqueous compartments. They can vary in their physiochemical properties such as size, lipid composition, surface charge and number and fluidity of the phospholipids bilayers. The most frequently used lipid for liposome formation are: 1,2-Dilauroyl-sn-Glycero-3-Phosphocholine (DLPC), 1,2-Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), 1,2-Dioleoyl-sn-Glycero-3-Phosphocholine (DOPC), 1,2-Dimyristoyl-sn-Glycero-3-Phosphoethanolamine (DMPE), 1,2-Dipalmitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol)] (Sodium Salt) (DMPG), 1,2-Dipalmitoyl-sn-Glycero-3-[Phospho-rac-(1-glycerol)] (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine] (Sodium Salt) (DMPS), 1,2-Dipalmitoyl-sn-Glycero-3-[Phospho-L-Serine] (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipid or modifiers of liposomes are preferred e.g. in combination with cholesterol and/or phosphatidylcholine.

Long-circulating liposomes are characterized by their ability to extravasate at body sites where the permeability of the vascular wall is increased. The most popular way to produce long circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy(Polyethylene glycol)-2000] (Ammonium Salt), 1,2-Dipalmitoyl-sn-Glycero-3-Phosphoethanolamine-N-[Methoxy(Polyethylene glycol)-5000] (Ammonium Salt), 1,2-Dioleoyl-3-Trimethylammonium-Propane (Chloride Salt) (DOTAP).

A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028, all of which are incorporated herein by reference. One method is described in example 9. Another method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder like form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

Micelles

Micelles are formed by surfactants (molecules that contain a hydrophobic portion and one or more ionic or otherwise strongly hydrophilic groups) in aqueous solution. As the concentration of a solid surfactant increases, its monolayers adsorbed at the air/water or glass/water interfaces become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated non-ionic detergents, the polyoxyethlene moieties are oriented outward and permeated by water. This arrangement is energetically favourable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces. The size of a micelle or its aggregation number is governed largely by geometric factors. The radius of the hydrocarbon core cannot exceed the length of the extended hydrocarbon chain of the surfactant molecule. Therefore, increasing the chain length or ascending homologous series increases the aggregation number of spherical micelles. If the surfactant concentration is increased beyond a few percent and if electrolytes are added (in the case of ionic surfactants) or the temperature is raised (in the case of non-ionic surfactants), the micelles increase in size. Under these conditions, the micelles are too large to remain spherical and become ellipsoidal, cylindrical or finally lamellar in shape.

Surfactants

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with IV injection such as, TWEEN-80, PLURONIC F-68, n-octyl-.beta.-D-glucopyranoside, and the like. In addition, phospholipids, such as those described for use in the production of liposomes, may also be used for micelle formation.

Physiologically Tolerable Carriers, Excipients Etc.

Pharmaceutical compositions of the present invention may contain a physiologically tolerable carrier together with at least one bioactive agent according to the present invention, dissolved or dispersed therein as an bioactive agent.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The bioactive agent can be mixed with excipients which are pharmaceutically acceptable and compatible with the bioactive agent and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the bioactive agent. It is preferred that the formulation has a pH within the range of 3.5-8, such as in the range 4.5-7.5, such as in the range 5.5-7, such as in the range 6-7.5, most preferably around 7.3. However, as is understood by one skilled in the art, the pH range may be adjusted according to the individual treated and the administration procedure. For example, in another preferred embodiment of the invention the formulation has a pH within the range 3.5-7, such as 4-6, such as 5-6, such as 5.3-5.7, such as 5.5.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

Administration Routes

In one embodiment of the present invention the bioactive agents of the present invention can be formulated as described in the literature for an administration route selected from subcutaneously, nasally, via the pulmonary route, such as via aerosol administration, by parenteral administration, orally, topically. Other suitable administration forms include suppositories, sprays, ointments, cremes, gels, inhalants, dermal patches, implants, pills, tablets, lozenges and capsules.

Topical administration of the bioactive agent according to the present invention is preferred.

Topical Administration of Pharmaceutical Compositions

The bioactive agents of the invention can also be delivered topically. Regions for topical administration include the skin surface and also mucous membrane tissues of the rectum, nose, mouth, and throat.

The topical composition may include a pharmaceutically acceptable carrier adapted for topical administration. Thus, the composition may take the form of a suspension, solution, ointment, lotion, cream, foam, aerosol, spray, suppository, implant, inhalant, tablet, capsule, dry powder, syrup, balm or lozenge, for example. Methods for preparing such compositions are well known in the pharmaceutical industry.

The bioactive agents of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Compositions suitable for topical administration in the mouth include lozenges comprising active agents in a flavoured base, usually sucrose and acacia or tragacanth; pastilles comprising the bioactive agent in an inert base such as gelatin and glycerin or sucrose and acacia; and mouthwashes comprising the bioactive agent in a suitable liquid carrier.

Creams, ointments or pastes according to the present invention are semi-solid compositions of the bioactive agent for external application. They may be made by mixing the bioactive agent in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

The bioactive agents described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the bioactive agent across the skin. The rate of such flux can be controlled by either providing a rate-controlling membrane or dispersing the bioactive agent in a polymer matrix or gel.

A variety of types of transdermal patches will find use in the methods described herein. For example, a simple adhesive patch can be prepared from a backing material and an acrylate adhesive. The bioactive agent(s) are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the bioactive agent(s). The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled bioactive agent solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the bioactive agent(s) is delivered from the device to the membrane is most advantageously controlled by the use of rate-limiting membranes which are placed between the reservoir and the skin. Assuming that the skin is sufficiently permeable to the bioactive agent (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Compositions comprising the bioactive agent according to the present invention can be delivered across the skin to have an effect on the tissues adjacent to the site of application (topical delivery) and/or to have an effect after distribution through the circulatory system (systemic delivery).

Transdermal medicine is one of the best ways of administering medicines quickly and effectively. Transdermal methods of delivery are widely used because they allow the absorption of medicine directly through the skin. Bypassing the stomach and liver means a much greater percentage of the active ingredient goes straight into the bloodstream where it's needed. In many cases, transdermal methods are used to help avoid potential side effects such as stomach upset or drowsiness.

There are two important layers to the human skin: (1) the Epidermis and (2) the Dermis. For transdermal delivery, the bioactive agent such as one or more drugs must pass through the two sub-layers of the epidermis to reach the microcirculation of the dermis.

The Stratum corneum is the top layer of the skin and varies in thickness from approximately ten to several hundred micrometres, depending on the region of the body. It is composed of layers of dead, flattened keratinocytes surrounded by a lipid matrix, which together act as a brick-and-mortar system that is difficult to penetrate.

The stratum corneum provides the most significant barrier to diffusion. In fact, the stratum corneum is the barrier to approximately 90% of transdermal drug applications. However, nearly all molecules penetrate it to some minimal degree. Below the stratum corneum lies the viable epidermis. This layer is about ten times as thick as the stratum corneum; however, diffusion is much faster here due to the greater degree of hydration in the living cells of the viable epidermis. Below the epidermis lies the dermis, which is approximately one millimeter thick, 100 times the thickness of the stratum corneum. The dermis contains small vessels that distribute drugs into the systemic circulation and to regulate temperature, a system known as the skin's microcirculation.

Advantages with Transdermal Administration

Transdermal drug delivery systems offer several important advantages over more traditional approaches, including:
  longer duration of action resulting in a reduction in dosing frequency
  Increased convenience to administer drugs which would otherwise require frequent dosing
  improved bioavailability
  more uniform plasma levels
  reduced side effects and improved therapy due to maintenance of plasma levels up to the end of the dosing interval
  flexibility of terminating the drug administration by simply removing the patch from the skin
  Improved patient compliance and comfort via non-invasive, painless and simple application Transdermal Pathways There are two main pathways by which the bioactive agent such as one or more drugs can cross the skin and reach the systemic circulation. The more direct route is known as the transcellular pathway. By this route, drugs cross the skin by directly passing through both the phospholipids membranes and the cytoplasm of the dead keratinocytes that constitute the stratum corneum.

Although this is the path of shortest distance, the bioactive agent such as one or more drugs encounter significant resistance to permeation. This is because the drugs must cross the lipophilic membrane of each cell, then the hydrophilic cellular contents containing keratin, and then the phospholipid bilayer of the cell one more time. This series of steps is repeated numerous times to traverse the full thickness of the stratum corneum.

The other more common pathway through the skin is via the intercellular route. Bioactive agent s crossing the skin by this route must pass through the small spaces between the cells of the skin, making the route more tortuous. Although the thickness of the stratum corneum is only about 20 µm, the actual diffusional path of most molecules crossing the skin is on the order of 400 µm. The 20-fold increase in the actual path of permeating molecules greatly reduces the rate of drug penetration.

A third pathway to breach the Stratum Corneum layer is via tiny microchannels created by a medical micro-needling device of which there are many brands and variants.

Devices and Formulations

Devices and formulations for transdermally administered bioactive agent s include:
  Transdermal patch
  Transdermal compositions including transdermal gels, lotions, ointments, creams, emulsion creams, pastes, sprays and lip balm etc.
  Micro-needling device
  Vesicles as a tool for transdermal and dermal delivery (cf. e.g. Loan Honeywell-Nguyen and Joke A. Bouwstra; Vesicles as a tool for transdermal and dermal delivery; Drug Discovery Today: Technologies Vol. 2, No. 1 2005)

Transdermal drug delivery is theoretically ideal for many injected and orally delivered drugs, but many drugs cannot pass through the skin because of skin's low permeability. Pharmaceutical companies develop new adhesives, molecular absorption enhancers, and penetration enhancers that will enhance skin permeability and thus greatly expand the range of drugs that can be delivered transdermally. Two of the better-known technologies that can help achieve significant skin permeation enhancement are iontophoresis and phonophoresis (sonophoresis).

Molecular Absorption Enhancement

Considerable research has been done on absorption enhancers, compounds that promote the passage of drugs through the stratum corneum. The present invention further comprises a composition comprising the bioactive agent according to this invention as well as one or more absorption enhancers.

The one or more absorption enhancers can be selected from the group consisting of Terpene derivatives, certain phenols, linalool, alpha terpineol, carvacrol, Limonene, menthone, eugenol, Phloretin, a polyphenol, padimate O [a para-aminobenzoicacid (PABA) and any derivative thereof.

Absorption Enhancement by Energy Input

Absorption enhancement of a composition comprising the bioactive agents according to the present invention can also be done by energy input as described herein below.

Also under study is the possibility of active transfer of drugs through the skin by the action of electrical or other forms of energy. The most research has been devoted to iontophoresis; sonophoresis and electroporation have been less well studied.

Iontophoresis involves passing a direct electrical current between two electrodes on the skin surface.

Phonophoresis uses ultrasonic frequencies to help transfer high molecular weight drugs through the skin.

Iontophoresis is a method of transferring substances across the skin by applying an electrical potential difference. It promotes the transfer of charged ionic drugs and possibly high molecular weight substances such as peptides. Electric current is applied through two electrodes, placed on the patient's skin. The first, or donor, electrode (cathode) delivers the negatively charged therapeutic agent (e.g., an organic acid), whereas the second, or receptor, electrode (anode) serves to close the circuit. This setup is named cathodal iontophoresis. For positively charged drugs (e.g., amines or peptides), the cell arrangement is reversed (anodal iontophoresis). The silver (anode) and silver chloride (cathode) electrode system—utilized in both types of iontophoresis—is favored largely because it does not affect the drug solution to the extent that other electrode systems can include intra-dermal administration of lidocaine as a local anesthetic and dexamethasone for local inflammation. The devices used are typically bench-top systems with patches connected to a power supply through cables; however, innovations in electronic circuit and battery technology may make small, integrated patch-like systems practicable Micro Needle-Enhanced Delivery A newer and potentially more promising technology is micro needle-enhanced delivery. These systems use an array of tiny needle-like structures to open pores in the stratum corneum and facilitate drug transport. The structures are small enough that they do not reach the nerve endings, so there is no sensation of pain. These systems have been reported to greatly enhance (up to 100,000 fold) the permeation of macromolecules through skin.

Transdermal Patches

There are five main types of transdermal patches.

1) Single-layer Drug-in-Adhesive: The adhesive layer of this system also contains the drug. In this type of patch the adhesive layer not only serves to adhere the various layers together, along with the entire system to the skin, but is also responsible for the releasing of the drug. The adhesive layer is surrounded by a temporary liner and a backing.

2) Multi-layer Drug-in-Adhesive: The multi-layer drug-in adhesive patch is similar to the single-layer system in that both adhesive layers are also responsible for the releasing of the drug. One of the layers is for immediate release of the drug and other layer is for control release of drug from the reservoir. The multi-layer system is different however that it adds another layer of drug-in-adhesive, usually separated by a membrane (but not in all cases). This patch also has a temporary liner-layer and a permanent backing.

3) Reservoir: Unlike the Single-layer and Multi-layer Drug-in-adhesive systems the reservoir transdermal system has a separate drug layer. The drug layer is a liquid compartment containing a drug solution or suspension separated by the adhesive layer. This patch is also backed by the backing layer. In this type of system the rate of release is zero order.

4) Matrix: The Matrix system has a drug layer of a semisolid matrix containing a drug solution or suspension. The adhesive layer in this patch surrounds the drug layer partially overlaying it. Also known as a monolithic device.

5) Vapour Patch: In this type of patch the adhesive layer not only serves to adhere the various layers together but also to release vapour. The vapour patches are new on the market and they release essential oils for up to 6 hours. The vapour patches release essential oils and are used in cases of decongestion mainly. Other vapour patches on the market are controller vapour patches that improve the quality of sleep. Vapour patches that reduce the quantity of cigarettes that one smokes in a month are also available on the market.

The table herein below describes some recent patents made in the field of transdermal patch. The content of U.S. Pat. Nos. 7,415,306, 7,413,748, 7,387,789, 7,398,121 and 7,395,111 is hereby incorporated into this patent application in their entirety.

| Patent No. | Date | Title | Information |
|---|---|---|---|
| U.S. Pat. No. 7,415,306 | Aug. 19, 2008 | Transdermal Delivery System for Anti-Emetic Medication | The present invention provides a transdermal delivery system for hydrophilic anti-emetic agents and methods of using thereof. The system includes an anti-emetic hydrophilic adhesive composition of a hydrophilic polymer and hydrophilic anti-emetic agent, a patch containing at least one hydrophilic layer of the composition, and an apparatus that generates hydrophilic micro-channels in skin of a subject using the patch or composition |
| U.S. Pat. No. 7,413,748 | Aug. 19, 2008 | Transdermal Buprenorphine to treat Pain in Sickle Cell Crisis | A specific dosage regimen of buprenorphine achieves pain relief from painful episodes due to sickle cell disease. The dosage regimen comprises administering to a patient in need of pain relief from sickle cell disease at least one BTDS transdermal patch. |
| U.S. Pat. No. 7,387,789 | Jul. 17, 2008 | Transdermal Delivery of Non-Steroidal Anti Inflammatory Drugs | The present invention provides a transdermal drug delivery system which comprises: a therapeutically effective amount of a non-steroidal anti-inflammatory drug; at least one dermal penetration enhancer, which is a safe skin-tolerant ester sunscreen ester; and at least one volatile liquid. The invention also provides a method for administering at least one systemic or locally acting non-steroidal anti-inflammatory drug to an animal |
| U.S. Pat. No. 7,398,121 | Jul. 8, 2008 | Iontophoresis Device | An iontophoresis device useful for administering an ionic drug by iontophoresis has an iontophoresis electrode section and a ground electrode section Both of which are to be connected to a power source. The iontophoresis device includes elements (members) of both of the electrode sections are all formed of membrane bodies, and includes ion exchange membranes different in ion selectivity, one being selective to ions of the same species as |

| Patent No. | Date | Title | Information |
|---|---|---|---|
| | | | charged ions of the ionic drug and the other to ions different in species from the charged ions of the ionic drug that are arranged in the iontophoresis electrode section, and at least an ion exchange membrane selective to ions opposite to the charged ions of the ionic drug is arranged in the ground electrode section. The iontophoresis device can administer the ionic drug stably over a long period of time at high transport efficiency. |
| U.S. Pat. No. 7,395,111 | Jul. 1, 2008 | Transdermal Delivery System for Water Insoluble Drug | The present invention provides a system for transdermal delivery of water insoluble drugs and methods using the same. The system includes a pharmaceutical composition of a water insoluble drug and a carrier molecule that enhances the solubility of the drug in aqueous solution, a medical patch containing the same and an apparatus that generates hydrophilic micro-channels in an area of skin of a subject using the composition or patch. |

Vesicle Formulations

The present invention can also be associated with vesicle formulations comprising the bioactive agents according to the present invention. Vesicles are water-filled colloidal particles. The walls of these capsules consist of amphiphilic molecules in a bilayer conformation. In an excess of water these amphiphilic molecules can form one (unilamellar vesicles) or more (multilamellar vesicles) concentric bilayers. Hydrophilic drugs can be entrapped into the internal aqueous compartment, whereas amphiphilic, lipophilic and charged hydrophilic drugs can be associated with the vesicle bilayer by hydrophobic and/or electrostatic interactions.

A wide variety of lipids and surfactants can be used to prepare vesicles for transdermal and dermal delivery. Most commonly, the vesicles are composed of phospholipids or non-ionic surfactants. These are referred to as liposomes and niosomes or nonionic surfactant vesicles, respectively. The composition of the vesicles influences their physico-chemical characteristics such as, size, charge, thermodynamic phase, lamellarity and bilayer elasticity. These physicochemical characteristics have a significant effect on the behavior of the vesicles and hence on their effectiveness as a drug delivery system.

Pharmacokinetics

After administration of the bioactive agents maximum plasma concentrations and exposures were—in one embodiment—observed to be higher than those after oral administration.

Bioavailability of transdermal bioactive agent was shown to be high, and the bioactive agent was shown to be rapidly and well absorbed, with peak plasma concentration occurring within 10 hours, such as within 9 hours, for example within 8 hours, such as within 7 hours, for example within 6 hours, such as within 5 hours, for example within 4 hours, such as within 3 hours, for example within 2 hours, such as within 1 hour, for example within 45 minutes, such as within 30 minutes, or for example within 15 minutes.

The half-life of elimination of transdermal bioactive agent can—in one embodiment—be more than 15 minutes, such as more than 30 minutes, for example more than 45 minutes, such as more than 1 hour, for example more than 2 hours, such as more than 3 hours, for example more than 4 hours, such as more than 5 hours, for example more than 6 hours, such as more than 7 hours, for example more than 8 hours, such as more than 9 hour, or for example more than 10 hours.

The half-life of elimination of transdermal bioactive agent can—in one embodiment—be less than 10 hours, such as less than 9 hours, for example less than 8 hours, such as less than 7 hours, for example less than 6 hours, such as less than 5 hours, for example less than 4 hours, such as less than 3 hours, for example less than 2 hours, such as less than 1 hour, for example less than 45 minutes, such as less than 30 minutes, or for example less than 15 minutes.

In one embodiment the plasma level of the bioactive agent can be sustained at a significant level for up to 24 hours post-treatment, such as for up to 22 hours, for example up to 20 hours, such as for up to 18 hours, for example up to 16 hours, such as for up to 14 hours, for example up to 12 hours, such as for up to 10 hours, for example up to 8 hours, such as for up to 6 hours, for example up to 4 hours, such as for up to 2 hours, for example up to 1 hour, such as for up to 30 minutes hours, or for example up to 15 minutes.

Items

The present invention is in preferred embodiments directed to the below-mentioned items:

1. One or more bioactive agent(s) derived from a liquid growth medium of a culture of a Basidiomycete cell for use of treatment one or more skin diseases.
2. The bioactive agent(s) of item 1, and wherein the Basidiomycete cell is selected from the group consisting of, but not limited to, *Ganoderma* sp. (such as *Ganoderma lucidum*), *Agaricus* sp., *Schizophyllum* sp., *Lentinula* sp. (such as *Lentinus edodes*), *Trametes* sp. and *Grifola* sp.
3. The bioactive agent(s) of any of items 1 to 2, wherein the bioactive agent comprises an anti-fungal activity.
4. The bioactive agent(s) of any of items 1 to 3, wherein the bioactive agent comprises an anti-bacterial activity.
5. The bioactive agent(s) of any of items 1 to 4, wherein the bioactive agent comprises an anti-viral activity.
6. The bioactive agent(s) of any of items 1 to 5, wherein the bioactive agent comprises an anti-inflammatory activity.
7. The bioactive agent(s) of any of items 1 to 6, wherein the bioactive agent comprises an anti-allergenic activity.
8. The bioactive agent(s) of any of items 1 to 7, wherein the bioactive agent is selected from the group consisting of agents comprising or consisting of an oligosaccharide, agents comprising or consisting of a polysaccharide, agents comprising or consisting of a beta glucans, agents comprising or consisting of an optionally glycosylated peptide, agents comprising or consisting of an optionally glycosylated polypeptide, agents comprising or consisting of an oligonucleotide,
agents comprising or consisting of a polynucleotide,
agents comprising or consisting of a lipid,
agents comprising or consisting of a fatty acid,
agents comprising or consisting of a fatty acid ester and
agents comprising or consisting of secondary metabolites.
9. The bioactive agent(s) of any of items 1 to 8, wherein the bioactive agent comprises or consists of an agent selected from an oligosaccharide, a polysaccharide and an optionally glycosylated polypeptide.
10. The bioactive agent(s) of any of items 1 to 9, wherein the bioactive agent comprises or consists of a polysaccharide.
11. The bioactive agent(s) of any of items 1 to 10, wherein the bioactive agent comprises or consists of an oligosaccharide.
12. The bioactive agent(s) of any of items 1 to 11, wherein the bioactive agent comprises or consists of an optionally glycolysated polypeptide.
13. The bioactive agent(s) of item 10, wherein the polysaccharide is a homopolymer.
14. The bioactive agent(s) of item 10, wherein the polysaccharide is a heteropolymer.
15. The bioactive agent(s) of item 10, wherein the polysaccharide comprises glucose monosaccharide units, optionally in combination with further monosaccharide units selected from the group of units consisting of glucuronic acid, galactose, mannose, arabinose and xylose, including any combination thereof.
16. The bioactive agent(s) of item 15, wherein the further monosaccharide units are all glucuronic acid.
17. The bioactive agent(s) of item 15, wherein the further monosaccharide units are all galactose.
18. The bioactive agent(s) of item 15, wherein the further monosaccharide units are all mannose.
19. The bioactive agent(s) of item 15, wherein the further monosaccharide units are all arabinose.
20. The bioactive agent(s) of item 15, wherein the further monosaccharide units are all xylose.
21. The bioactive agent(s) of item 15, wherein the further monosaccharide units are glucuronic acid and galactose.
22. The bioactive agent(s) of item 15, wherein the further monosaccharide units are glucuronic acid and mannose.
23. The bioactive agent(s) of item 15, wherein the further monosaccharide units are glucuronic acid and arabinose.
24. The bioactive agent(s) of item 15, wherein the further monosaccharide units are glucuronic acid and xylose.
25. The bioactive agent(s) of item 15, wherein the further monosaccharide units are galactose and mannose.
26. The bioactive agent(s) of item 15, wherein the further monosaccharide units are galactose and arabinose.
27. The bioactive agent(s) of item 15, wherein the further monosaccharide units are galactose and xylose.
28. The bioactive agent(s) of item 15, wherein the further monosaccharide units are mannose and arabinose.
29. The bioactive agent(s) of item 15, wherein the further monosaccharide units are mannose and xylose.
30. The bioactive agent(s) of item 15, wherein the further monosaccharide units are arabinose and xylose.
31. The bioactive agent(s) of item 15, wherein the further monosaccharide units are glucuronic acid, galactose and mannose.
32. The bioactive agent(s) of item 15, wherein the further monosaccharide units are glucuronic acid, galactose and arabinose.
33. The bioactive agent(s) of item 15, wherein the further monosaccharide units are glucuronic acid, galactose and xylose.
34. The bioactive agent(s) of item 15, wherein the further monosaccharide units are glucuronic acid, mannose and arabinose.
35. The bioactive agent(s) of item 15, wherein the further monosaccharide units are glucuronic acid mannose and xylose.
36. The bioactive agent(s) of item 15, wherein the further monosaccharide units are glucuronic acid, arabinose and xylose.
37. The bioactive agent(s) of item 15, wherein the further monosaccharide units are galactose, mannose and arabinose.
38. The bioactive agent(s) of item 15, wherein the further monosaccharide units are galactose, mannose and xylose.
39. The bioactive agent(s) of item 15, wherein the further monosaccharide units are galactose, arabinose and xylose.
40. The bioactive agent(s) of item 15, wherein the further monosaccharide units are mannose, arabinose and xylose.
41. The bioactive agent(s) of item 15, wherein the further monosaccharide units are glucuronic acid, galactose, mannose and arabinose.
42. The bioactive agent(s) of item 15, wherein the further monosaccharide units are glucuronic acid, galactose, mannose and xylose.
43. The bioactive agent(s) of item 15, wherein the further monosaccharide units are glucuronic acid, galactose, arabinose and xylose.
44. The bioactive agent(s) of item 15, wherein the further monosaccharide units are glucuronic acid, mannose, arabinose and xylose.
45. The bioactive agent(s) of item 15, wherein the further monosaccharide units are galactose, mannose, arabinose and xylose.
46. The bioactive agent(s) of item 10, wherein the backbone of the polysaccharide comprises glucose monosaccharide units in combination with further monosaccharide units selected from the group of units consisting of glucuronic acid, galactose, mannose, arabinose and xylose, including any combination thereof.
47. The bioactive agent(s) of item 46, wherein the further monosaccharide units are all glucuronic acid.
48. The bioactive agent(s) of item 46, wherein the further monosaccharide units are all galactose.
49. The bioactive agent(s) of item 46, wherein the further monosaccharide units are all mannose.
50. The bioactive agent(s) of item 46, wherein the further monosaccharide units are all arabinose.
51. The bioactive agent(s) of item 46, wherein the further monosaccharide units are all xylose.
52. The bioactive agent(s) of item 46, wherein the further monosaccharide units are glucuronic acid and galactose.
53. The bioactive agent(s) of item 46, wherein the further monosaccharide units are glucuronic acid and mannose.
54. The bioactive agent(s) of item 46, wherein the further monosaccharide units are glucuronic acid and arabinose.
55. The bioactive agent(s) of item 46, wherein the further monosaccharide units are glucuronic acid and xylose.
56. The bioactive agent(s) of item 46, wherein the further monosaccharide units are galactose and mannose.
57. The bioactive agent(s) of item 46, wherein the further monosaccharide units are galactose and arabinose.
58. The bioactive agent(s) of item 46, wherein the further monosaccharide units are galactose and xylose.

59. The bioactive agent(s) of item 46, wherein the further monosaccharide units are mannose and arabinose.
60. The bioactive agent(s) of item 46, wherein the further monosaccharide units are mannose and xylose.
61. The bioactive agent(s) of item 46, wherein the further monosaccharide units are arabinose and xylose.
62. The bioactive agent(s) of item 46, wherein the further monosaccharide units are glucuronic acid, galactose and mannose.
63. The bioactive agent(s) of item 46, wherein the further monosaccharide units are glucuronic acid, galactose and arabinose.
64. The bioactive agent(s) of item 46, wherein the further monosaccharide units are glucuronic acid, galactose and xylose.
65. The bioactive agent(s) of item 46, wherein the further monosaccharide units are glucuronic acid, mannose and arabinose.
66. The bioactive agent(s) of item 46, wherein the further monosaccharide units are glucuronic acid mannose and xylose.
67. The bioactive agent(s) of item 46, wherein the further monosaccharide units are glucuronic acid, arabinose and xylose.
68. The bioactive agent(s) of item 46, wherein the further monosaccharide units are galactose, mannose and arabinose.
69. The bioactive agent(s) of item 46, wherein the further monosaccharide units are galactose, mannose and xylose.
70. The bioactive agent(s) of item 46, wherein the further monosaccharide units are galactose, arabinose and xylose.
71. The bioactive agent(s) of item 46, wherein the further monosaccharide units are mannose, arabinose and xylose.
72. The bioactive agent(s) of item 46, wherein the further monosaccharide units are glucuronic acid, galactose, mannose and arabinose.
73. The bioactive agent(s) of item 46, wherein the further monosaccharide units are glucuronic acid, galactose, mannose and xylose.
74. The bioactive agent(s) of item 46, wherein the further monosaccharide units are glucuronic acid, galactose, arabinose and xylose.
75. The bioactive agent(s) of item 46, wherein the further monosaccharide units are glucuronic acid, mannose, arabinose and xylose.
76. The bioactive agent(s) of item 46, wherein the further monosaccharide units are galactose, mannose, arabinose and xylose.
77. The bioactive agent(s) of item 10, wherein the backbone of the polysaccharide comprises a plurality of monosaccharide units, and wherein the side chains of the polysaccharide comprises further monosaccharide units selected from the group of units consisting of glucuronic acid, galactose, mannose, arabinose xylose and glucose, including any combination thereof.
78. The bioactive agent(s) of item 77, wherein the further monosaccharide units are all glucuronic acid.
79. The bioactive agent(s) of item 77, wherein the further monosaccharide units are all galactose.
80. The bioactive agent(s) of item 77, wherein the further monosaccharide units are all mannose.
81. The bioactive agent(s) of item 77, wherein the further monosaccharide units are all arabinose.
82. The bioactive agent(s) of item 77, wherein the further monosaccharide units are all xylose.
83. The bioactive agent(s) of item 77, wherein the further monosaccharide units are all glucose.
84. The bioactive agent(s) of item 77, wherein the further monosaccharide units are glucuronic acid and galactose.
85. The bioactive agent(s) of item 77, wherein the further monosaccharide units are glucuronic acid and mannose.
86. The bioactive agent(s) of item 77, wherein the further monosaccharide units are glucuronic acid and arabinose.
87. The bioactive agent(s) of item 77, wherein the further monosaccharide units are glucuronic acid and xylose.
88. The bioactive agent(s) of item 77, wherein the further monosaccharide units are glucuronic acid and glucose.
89. The bioactive agent(s) of item 77, wherein the further monosaccharide units are galactose and mannose.
90. The bioactive agent(s) of item 77, wherein the further monosaccharide units are galactose and arabinose.
91. The bioactive agent(s) of item 77, wherein the further monosaccharide units are galactose and xylose.
92. The bioactive agent(s) of item 77, wherein the further monosaccharide units are galactose and glucose.
93. The bioactive agent(s) of item 77, wherein the further monosaccharide units are mannose and arabinose.
94. The bioactive agent(s) of item 77, wherein the further monosaccharide units are mannose and xylose.
95. The bioactive agent(s) of item 77, wherein the further monosaccharide units are mannose and glucose.
96. The bioactive agent(s) of item 77, wherein the further monosaccharide units are arabinose and xylose.
97. The bioactive agent(s) of item 77, wherein the further monosaccharide units are arabinose and glucose.
98. The bioactive agent(s) of item 77, wherein the further monosaccharide units are xylose and glucose.
99. The bioactive agent(s) of item 77, wherein the further monosaccharide units are glucuronic acid, galactose and mannose.
100. The bioactive agent(s) of item 77, wherein the further monosaccharide units are glucuronic acid, galactose and arabinose.
101. The bioactive agent(s) of item 77, wherein the further monosaccharide units are glucuronic acid, galactose and xylose.
102. The bioactive agent(s) of item 77, wherein the further monosaccharide units are glucuronic acid, galactose and glucose.
103. The bioactive agent(s) of item 77, wherein the further monosaccharide units are glucuronic acid, mannose and arabinose.
104. The bioactive agent(s) of item 77, wherein the further monosaccharide units are glucuronic acid mannose and xylose.
105. The bioactive agent(s) of item 77, wherein the further monosaccharide units are glucuronic acid mannose and glucose.
106. The bioactive agent(s) of item 77, wherein the further monosaccharide units are glucuronic acid, arabinose and xylose.
107. The bioactive agent(s) of item 77, wherein the further monosaccharide units are glucuronic acid, arabinose and glucose.
108. The bioactive agent(s) of item 77, wherein the further monosaccharide units are glucuronic acid, xylose and glucose.
109. The bioactive agent(s) of item 77, wherein the further monosaccharide units are galactose, mannose and arabinose.
110. The bioactive agent(s) of item 77, wherein the further monosaccharide units are galactose, mannose and xylose.

111. The bioactive agent(s) of item 77, wherein the further monosaccharide units are galactose, mannose and glucose.
112. The bioactive agent(s) of item 77, wherein the further monosaccharide units are galactose, arabinose and xylose.
113. The bioactive agent(s) of item 77, wherein the further monosaccharide units are galactose, arabinose and glucose.
114. The bioactive agent(s) of item 77, wherein the further monosaccharide units are galactose, xylose and glucose.
115. The bioactive agent(s) of item 77, wherein the further monosaccharide units are mannose, arabinose and xylose.
116. The bioactive agent(s) of item 77, wherein the further monosaccharide units are mannose, arabinose and glucose.
117. The bioactive agent(s) of item 77, wherein the further monosaccharide units are mannose, xylose and glucose.
118. The bioactive agent(s) of item 77, wherein the further monosaccharide units are arabinose, xylose and glucose.
119. The bioactive agent(s) of item 77, wherein the further monosaccharide units are glucuronic acid, galactose, mannose and arabinose.
120. The bioactive agent(s) of item 77, wherein the further monosaccharide units are glucuronic acid, galactose, mannose and xylose.
121. The bioactive agent(s) of item 77, wherein the further monosaccharide units are glucuronic acid, galactose, mannose and glucose.
122. The bioactive agent(s) of item 77, wherein the further monosaccharide units are glucuronic acid, galactose, arabinose and xylose.
123. The bioactive agent(s) of item 77, wherein the further monosaccharide units are glucuronic acid, galactose, arabinose and glucose.
124. The bioactive agent(s) of item 77, wherein the further monosaccharide units are glucuronic acid, galactose, xylose and glucose.
125. The bioactive agent(s) of item 77, wherein the further monosaccharide units are glucuronic acid, mannose, arabinose and xylose.
126. The bioactive agent(s) of item 77, wherein the further monosaccharide units are glucuronic acid, mannose, arabinose and glucose.
127. The bioactive agent(s) of item 77, wherein the further monosaccharide units are glucuronic acid, mannose, xylose and glucose.
128. The bioactive agent(s) of item 77, wherein the further monosaccharide units are glucuronic acid, arabinose, xylose and glucose.
129. The bioactive agent(s) of item 77, wherein the further monosaccharide units are galactose, mannose, arabinose and xylose.
130. The bioactive agent(s) of item 77, wherein the further monosaccharide units are galactose, mannose, arabinose and glucose.
131. The bioactive agent(s) of item 77, wherein the further monosaccharide units are galactose, mannose, xylose and glucose.
132. The bioactive agent(s) of item 77, wherein the further monosaccharide units are galactose, arabinose, xylose and glucose.
133. The bioactive agent(s) of item 77, wherein the further monosaccharide units are mannose, arabinose, xylose and glucose.
134. The bioactive agent(s) of item 77, wherein the further monosaccharide units are glucuronic acid, galactose, mannose, arabinose and xylose.
135. The bioactive agent(s) of item 77, wherein the further monosaccharide units are glucuronic acid, galactose, mannose, arabinose and glucose.
136. The bioactive agent(s) of item 77, wherein the further monosaccharide units are glucuronic acid, galactose, mannose, xylose and glucose.
137. The bioactive agent(s) of item 77, wherein the further monosaccharide units are glucuronic acid, galactose, arabinose xylose and glucose.
138. The bioactive agent(s) of item 77, wherein the further monosaccharide units are glucuronic acid, mannose, arabinose xylose and glucose.
139. The bioactive agent(s) of item 77, wherein the further monosaccharide units are galactose, mannose, arabinose xylose and glucose.
140. The bioactive agent(s) of item 10, wherein the polysaccharide comprises a repetitive backbone macromomer comprising from 2 to 6, such as 2, 3, 4, 5 or 6 different monosaccharide units and having from 1 to 3 monosaccharide units selected from glucose, mannose and galactose.
141. The bioactive agent(s) of item 10, wherein the polysaccharide comprises an average of from 1 to 1000 monosaccharide units in the backbone between each branching point, such as from 2 to 1000 monosaccharide units, for example from 3 to 1000 monosaccharide units, such as from 4 to 1000 monosaccharide units, for example from 5 to 1000 monosaccharide units, such as from 6 to 1000 monosaccharide units, for example from 7 to 1000 monosaccharide units, such as from 8 to 1000 monosaccharide units, for example from 9 to 1000 monosaccharide units, such as from 10 to 1000 monosaccharide units, for example from 11 to 1000 monosaccharide units, such as from 12 to 1000 monosaccharide units, for example from 13 to 1000 monosaccharide units, such as from 14 to 1000 monosaccharide units, for example from 15 to 1000 monosaccharide units, such as from 20 to 1000 monosaccharide units, for example from 25 to 1000 monosaccharide units, such as from 30 to 1000 monosaccharide units, for example from 40 to 1000 monosaccharide units, such as from 50 to 1000 monosaccharide units, for example from 60 to 1000 monosaccharide units, such as from 70 to 1000 monosaccharide units, for example from 80 to 1000 monosaccharide units, such as from 90 to 1000 monosaccharide units, for example from 100 to 1000 monosaccharide units, such as from 2 to 500 monosaccharide units, for example from 3 to 500 monosaccharide units, such as from 4 to 500 monosaccharide units, for example from 5 to 500 monosaccharide units, such as from 6 to 500 monosaccharide units, for example from 7 to 500 monosaccharide units, such as from 8 to 500 monosaccharide units, for example from 9 to 500 monosaccharide units, such as from 10 to 500 monosaccharide units, for example from 11 to 500 monosaccharide units, such as from 12 to 500 monosaccharide units, for example from 13 to 500 monosaccharide units, such as from 14 to 500 monosaccharide units, for example from 15 to 500 monosaccharide units, such as from 20 to 500 monosaccharide units, for example from 25 to 500 monosaccharide units, such as from 30 to 500 monosaccharide units, for example from 40 to 500 monosaccharide units, such as from 50 to 500 monosaccharide units, for example from 60 to 500 monosaccharide units, such as from 70 to 500 monosaccharide units, for example from 80 to 500 monosaccharide units, such as from 90 to 500 monosaccharide units, for example from 100 to 500 monosaccharide units, such as from 2 to 250 monosaccharide units, for example from 3 to 250 monosaccharide units, such as from 4 to 250 monosaccharide units, for example from 5 to 250 monosaccharide units, such as from 6 to 250 monosaccharide units, for example from 7 to 250 monosaccharide units, such as from 8 to 250 monosaccharide units, for example from 9 to 250 monosaccharide units, such as from 10 to 250 monosaccharide units, for example from 11 to 250 monosaccharide units, such as from 12 to 250 monosaccharide units, for example from 13 to 250 monosaccharide units, such as from 14 to 250 monosaccharide units, for example from 15 to 250 monosaccharide units, such as from 20 to 250 monosaccharide units, for example from 25 to 250 monosaccharide units, such as from 30 to 250 monosaccharide units, for example from 40 to 250 monosaccharide units, such as from 50 to 250 monosaccharide units, for example from 60 to 250 monosaccharide units, such as from 70 to 250 monosaccharide units, for example from 80 to 250 monosaccharide units, such as from 90 to 250 monosaccharide units, for example from 100 to 250 monosaccharide units, such as from 2 to 100 monosaccharide units, for example from 3 to 100 monosaccharide units, such as from 4 to 100 monosaccharide units, for example from 5 to 100 monosaccharide units, such as from 6 to 100 monosaccharide units, for example from 7 to 100 monosaccharide units, such as from 8 to 100 monosaccharide units, for example from 9 to 100 monosaccharide units, such as from 10 to 100 monosaccharide units, for example from 11 to 100 monosaccharide units, such as from 12 to 100 monosaccharide units, for example from 13 to 100 monosaccharide units, such as from 14 to 100 monosaccharide units, for example from 15 to 100 monosaccharide units, such as from 20 to 100 monosaccharide units, for example from 25 to 100 monosaccharide units, such as from 30 to 100 monosaccharide units, for example from 40 to 100 monosaccharide units, such as from 50 to 100 monosaccharide units, for example from 60 to 100 monosaccharide units, such as from 70 to 100 monosaccharide units, for example from 80 to 100 monosaccharide units, such as from 90 to 100 monosaccharide units, such as from 2 to 50 monosaccharide units, for example from 3 to 50 monosaccharide units, such as from 4 to 50 monosaccharide units, for example from 5 to 50 monosaccharide units, such as from 6 to 50 monosaccharide units, for example from 7 to 50 monosaccharide units, such as from 8 to 50 monosaccharide units, for example from 9 to 50 monosaccharide units, such as from 10 to 50 monosaccharide units, for example from 11 to 50 monosaccharide units, such as from 12 to 50 monosaccharide units, for example from 13 to 50 monosaccharide units, such as from 14 to 50 monosaccharide units, for example from 15 to 50 monosaccharide units, such as from 20 to 50 monosaccharide units, for example from 25 to 50 monosaccharide units, such as from 30 to 50 monosaccharide units, for example from 40 to 50 monosaccharide units, such as from 2 to 25 monosaccharide units, for example from 3 to 25 monosaccharide units, such as from 4 to 25 monosaccharide units, for example from 5 to 25 monosaccharide units, such as from 6 to 25 monosaccharide units, for example from 7 to 25 monosaccharide units, such as from 8 to 25 monosaccharide units, for example from 9 to 25 monosaccharide units, such as from 10 to 25 monosaccharide units, for example from 11 to 25 monosaccharide units, such as from 12 to 25 monosaccharide units, for example from 13 to 25 monosaccharide units, such as from 14 to 25 monosaccharide units, for example from 15 to 25 monosaccharide units, such as from 20 to 25 monosaccharide units, such as from 2 to 20 monosaccharide units, for example from 3 to 20 monosaccharide units, such as from 4 to 20 monosaccharide units, for example from 5 to 20 monosaccharide units, such as from 6 to 20 monosaccharide units, for example from 7 to 20 monosaccharide units, such as from 8 to 20 monosaccharide units, for example from 9 to 20 monosaccharide units, such as from 10 to 20 monosaccharide units, for example from 11 to 20 monosaccharide units, such as from 12 to 20 monosaccharide units, for example from 13 to 20 monosaccharide units, such as from 14 to 20 monosaccharide units, for example from 15 to 20 monosaccharide units, such as from 2 to 18 monosaccharide units, for example from 3 to 18 monosaccharide units, such as from 4 to 18 monosaccharide units, for example from 5 to 18 monosaccharide units, such as from 6 to 18 monosaccharide units, for example from 7 to 18 monosaccharide units, such as from 8 to 18 monosaccharide units, for example from 9 to 18 monosaccharide units, such as from 10 to 18 monosaccharide units, for example from 11 to 18 monosaccharide units, such as from 12 to 18 monosaccharide units, for example from 13 to 18 monosaccharide units, such as from 14 to 18 monosaccharide units, for example from 15 to 18 monosaccharide units, such as from 2 to 16 monosaccharide units, for example from 3 to 16 monosaccharide units, such as from 4 to 16 monosaccharide units, for example from 5 to 16 monosaccharide units, such as from 6 to 16 monosaccharide units, for example from 7 to 16 monosaccharide units, such as from 8 to 16 monosaccharide units, for example from 9 to 16 monosaccharide units, such as from 10 to 16 monosaccharide units, for example from 11 to 16 monosaccharide units, such as from 12 to 16 monosaccharide units, for example from 13 to 16 monosaccharide units, such as from 14 to 16 monosaccharide units, for example from 15 to 16 monosaccharide units, such as from 2 to 14 monosaccharide units, for example from 3 to 14 monosaccharide units, such as from 4 to 14 monosaccharide units, for example from 5 to 14 monosaccharide units, such as from 6 to 14 monosaccharide units, for example from 7 to 14 monosaccharide units, such as from 8 to 14 monosaccharide units, for example from 9 to 14 monosaccharide units, such as from 10 to 14 monosaccharide units, for example from 11 to 14 monosaccharide units, such as from 12 to 14 monosaccharide units, for example from 13 to 14 monosaccharide units, such as from 2 to 12 monosaccharide units, for example from 3 to 12 monosaccharide units, such as from 4 to 12 monosaccharide units, for example from 5 to 12 monosaccharide units, such as from 6 to 12 monosaccharide units, for example from 7 to 12 monosaccharide units, such as from 8 to 12 monosaccharide units, for example from 9 to 12 monosaccharide units, such as from 10 to 12 monosaccharide units, for example from 11 to 12 monosaccharide units, such as from 2 to 10 monosaccharide units, for example from 3 to 10 monosaccharide units, such as from 4 to 10 monosaccharide units, for example from 5 to 10 monosaccharide units, such as from 6 to 10 monosaccharide units, for example from 7 to 10 monosaccharide units, such as from 8 to 10 monosaccharide units, for example from 9 to 10 monosaccharide units, such as from 2 to 8 monosaccharide units, for example from 3 to 8 monosaccharide units, such as from 4 to 8 monosaccharide units, for example from 5 to 8 monosaccharide units, such as from 6 to 8 monosaccharide units, for example from 7 to 8 monosaccharide units in the backbone between each branching point.

142. The bioactive agent(s) of item 10, wherein some or all of the polysaccharide has a molecular weight in the range of from 5,000 g/mol to about 1,000,000 g/mol, such as a molecular weight in the range of from 5,000 g/mol to about 900,000 g/mol, for example a molecular weight in the range of from 5,000 g/mol to about 800,000 g/mol, such as a molecular weight in the range of from 5,000 g/mol to about 900,000 g/mol, for example a molecular weight in the range of from 5,000 g/mol to about 800,000 g/mol, such as a molecular weight in the range of from 5,000 g/mol to about 750,000 g/mol, for example a molecular weight in the range of from 5,000 g/mol to about 700,000 g/mol, such as a molecular weight in the range of from 5,000 g/mol to about 1270,000 g/mol, for example a molecular weight in the range of from 5,000 g/mol to about 600,000 g/mol, such as a molecular weight in the range of from 5,000 g/mol to about 550,000 g/mol, for example a molecular weight in the range of from 5,000 g/mol to about 500,000 g/mol, such as a molecular weight in the range of from 5,000 g/mol to about 450,000 g/mol, for example a molecular weight in the range of from 5,000 g/mol to about 400,000 g/mol, such as a molecular weight in the range of from 5,000 g/mol to about 350,000 g/mol, for example a molecular weight in the range of from 5,000 g/mol to about 300,000 g/mol, such as a molecular weight in the range of from 5,000 g/mol to about 250,000 g/mol, for example a molecular weight in the range of from 5,000 g/mol to about 200,000 g/mol, such as a molecular weight in the range of from 5,000 g/mol to about 100,000 g/mol, for example a molecular weight in the range of from 5,000 g/mol to about 80,000 g/mol, such as a molecular weight in the range of from 5,000 g/mol to about 60,000 g/mol, for example a molecular weight in the range of from 5,000 g/mol to about 50,000 g/mol, such as a molecular weight in the range of from 5,000 g/mol to about 40,000 g/mol, for example a molecular weight in the range of from 5,000 g/mol to about 35,000 g/mol, such as a molecular weight in the range of from 5,000 g/mol to about 30,000 g/mol, for example a molecular weight in the range of from 5,000 g/mol to about 25,000 g/mol, such as a molecular weight in the range of from 5,000 g/mol to about 20,000 g/mol, for example a molecular weight in the range of from 5,000 g/mol to about 15,000 g/mol, such as a molecular weight in the range of from 5,000 g/mol to about 10,000 g/mol, for example a molecular weight in the range of from 10,000 g/mol to about 1,000,000 g/mol, such as a molecular weight in the range of from 10,000 g/mol to about 900,000 g/mol, for example a molecular weight in the range of from 10,000 g/mol to about 800,000 g/mol, such as a molecular weight in the range of from 10,000 g/mol to about 900,000 g/mol, for example a molecular weight in the range of from 10,000 g/mol to about 800,000 g/mol, such as a molecular weight in the range of from 10,000 g/mol to about 750,000 g/mol, for example a molecular weight in the range of from 10,000 g/mol to about 700,000 g/mol, such as a molecular weight in the range of from 10,000 g/mol to about 1270,000 g/mol, for example a molecular weight in the range of from 10,000 g/mol to about 600,000 g/mol, such as a molecular weight in the range of from 10,000 g/mol to about 550,000 g/mol, for example a molecular weight in the range of from 10,000 g/mol to about 500,000 g/mol, such as a molecular weight in the range of from 10,000 g/mol to about 450,000 g/mol, for example a molecular weight in the range of from 10,000 g/mol to about 400,000 g/mol, such as a molecular weight in the range of from 10,000 g/mol to about 350,000 g/mol, for example a molecular weight in the range of from 10,000 g/mol to about 300,000 g/mol, such as a molecular weight in the range of from 10,000 g/mol to about 250,000 g/mol, for example a molecular weight in the range of from 10,000 g/mol to about 200,000 g/mol, such as a molecular weight in the range of from 10,000 g/mol to about 100,000 g/mol, for example a molecular weight in the range of from 10,000 g/mol to about 80,000 g/mol, such as a molecular weight in the range of from 10,000 g/mol to about 60,000 g/mol, for example a molecular weight in the range of from 10,000 g/mol to about 50,000 g/mol, such as a molecular weight in the range of from 10,000 g/mol to about 40,000 g/mol, for example a molecular weight in the range of from 10,000 g/mol to about 35,000 g/mol, such as a molecular weight in the range of from 10,000 g/mol to about 30,000 g/mol, for example a molecular weight in the range of from 10,000 g/mol to about 25,000 g/mol, such as a molecular weight in the range of from 10,000 g/mol to about 20,000 g/mol, for example a molecular weight in the range of from 10,000 g/mol to about 15,000 g/mol, such as a molecular weight in the range of from 15,000 g/mol to about 1,000,000 g/mol, such as a molecular weight in the range of from 15,000 g/mol to about 900,000 g/mol, for example a molecular weight in the range of from 15,000 g/mol to about 800,000 g/mol, such as a molecular weight in the range of from 15,000 g/mol to about 900,000 g/mol, for example a molecular weight in the range of from 15,000 g/mol to about 800,000 g/mol, such as a molecular weight in the range of from 15,000 g/mol to about 750,000 g/mol, for example a molecular weight in the range of from 15,000 g/mol to about 700,000 g/mol, such as a molecular weight in the range of from 15,000 g/mol to about 1270,000 g/mol, for example a molecular weight in the range of from 15,000 g/mol to about 600,000 g/mol, such as a molecular weight in the range of from 15,000 g/mol to about 550,000 g/mol, for example a molecular weight in the range of from 15,000 g/mol to about 500,000 g/mol, such as a molecular weight in the range of from 15,000 g/mol to about 450,000 g/mol, for example a molecular weight in the range of from 15,000 g/mol to about 400,000 g/mol, such as a molecular weight in the range of from 15,000 g/mol to about 350,000 g/mol, for example a molecular weight in the range of from 15,000 g/mol to about 300,000 g/mol, such as a molecular weight in the range of from 15,000 g/mol to about 250,000 g/mol, for example a molecular weight in the range of from 15,000 g/mol to about 200,000 g/mol, such as a molecular weight in the range of from 15,000 g/mol to about 100,000 g/mol, for example a molecular weight in the range of from 15,000 g/mol to about 80,000 g/mol, such as a molecular weight in the range of from 15,000 g/mol to about 60,000 g/mol, for example a molecular weight in the range of from 15,000 g/mol to about 50,000 g/mol, such as a molecular weight in the range of from 15,000 g/mol to about 40,000 g/mol, for example a molecular weight in the range of from 15,000 g/mol to about 35,000 g/mol, such as a molecular weight in the range of from 15,000 g/mol to about 30,000 g/mol, for example a molecular weight in the range of from 15,000 g/mol to about 25,000 g/mol, such as a molecular weight in the range of from 15,000 g/mol to about 20,000 g/mol, for example a molecular weight in the range of from 20,000 g/mol to about 1,000,000 g/mol, such as a molecular weight in the range of from 20,000 g/mol to about 900,000 g/mol, for example a molecular weight in the range of from 20,000 g/mol to about 800,000 g/mol, such as a molecular weight in the range of from 20,000 g/mol to about 900,000 g/mol, for example a molecular weight in the range of from 20,000 g/mol to about 800,000 g/mol, such as a molecular weight in the range of from 20,000 g/mol to about 750,000 g/mol, for example a molecular weight in the range of from 20,000 g/mol to about 700,000 g/mol, such as a molecular weight in the range of from 20,000 g/mol to about 1270,000 g/mol, for example a molecular weight in the range of from 20,000 g/mol to about 600,000 g/mol, such as a molecular weight in the range of from 20,000 g/mol to about 550,000 g/mol, for example a molecular weight in the range of from 20,000 g/mol to about 500,000 g/mol, such as a molecular weight in the range of from 20,000 g/mol to about 450,000 g/mol, for example a molecular weight in the range of from 20,000 g/mol to about 400,000 g/mol, such as a molecular weight in the range of from 20,000 g/mol to about 350,000 g/mol, for example a molecular weight in the range of from 20,000 g/mol to about 300,000 g/mol, such as a molecular weight in the range of from 20,000 g/mol to about 250,000 g/mol, for example a molecular weight in the range of from 20,000 g/mol to about 200,000 g/mol, such as a molecular weight in the range of from 20,000 g/mol to about 100,000 g/mol, for example a molecular weight in the range of from 20,000 g/mol to about 80,000 g/mol, such as a molecular weight in the range of from 20,000 g/mol to about 60,000 g/mol, for example a molecular weight in the range of from 20,000 g/mol to about 50,000 g/mol, such as a molecular weight in the range of from 20,000 g/mol to about 40,000 g/mol, for example a molecular weight in the range of from 20,000 g/mol to about 35,000 g/mol, such as a molecular weight in the range of from 20,000 g/mol to about 30,000 g/mol, for example a molecular weight in the range of from 20,000 g/mol to about 25,000 g/mol, such as a molecular weight in the range of from 25,000 g/mol to about 1,000,000 g/mol, such as a molecular weight in the range of from 25,000 g/mol to about 900,000 g/mol, for example a molecular weight in the range of from 25,000 g/mol to about 800,000 g/mol, such as a molecular weight in the range of from 25,000 g/mol to about 900,000 g/mol, for example a molecular weight in the range of from 25,000 g/mol to about 800,000 g/mol, such as a molecular weight in the range of from 25,000 g/mol to about 750,000 g/mol, for example a molecular weight in the range of from 25,000 g/mol to about 700,000 g/mol, such as a molecular weight in the range of from 25,000 g/mol to about 1270,000 g/mol, for example a molecular weight in the range of from 25,000 g/mol to about 600,000 g/mol, such as a molecular weight in the range of from 25,000 g/mol to about 550,000 g/mol, for example a molecular weight in the range of from 25,000 g/mol to about 500,000 g/mol, such as a molecular weight in the range of from 25,000 g/mol to about 450,000 g/mol, for example a molecular weight in the range of from 25,000 g/mol to about 400,000 g/mol, such as a molecular weight in the range of from 25,000 g/mol to about 350,000 g/mol, for example a molecular weight in the range of from 25,000 g/mol to about 300,000 g/mol, such as a molecular weight in the range of from 25,000 g/mol to about 250,000 g/mol, for example a molecular weight in the range of from 25,000 g/mol to about 200,000 g/mol, such as a molecular weight in the range of from 25,000 g/mol to about 100,000 g/mol, for example a molecular weight in the range of from 25,000 g/mol to about 80,000 g/mol, such as a molecular weight in the range of from 25,000 g/mol to about 60,000 g/mol, for example a molecular weight in the range of from 25,000 g/mol to about 50,000 g/mol, such as a molecular weight in the range of from 25,000 g/mol to about 40,000 g/mol, for example a molecular weight in the range of from 25,000 g/mol to about 35,000 g/mol, such as a molecular weight in the range of from 25,000 g/mol to about 30,000 g/mol, for example a molecular weight in the range of from 30,000 g/mol to about 1,000,000 g/mol, such as a molecular weight in the range of from 30,000 g/mol to about 900,000 g/mol, for example a molecular weight in the range of from 30,000 g/mol to about 800,000 g/mol, such as a molecular weight in the range of from 30,000 g/mol to about 900,000 g/mol, for example a molecular weight in the range of from 30,000 g/mol to about 800,000 g/mol, such as a molecular weight in the range of from 30,000 g/mol to about 750,000 g/mol, for example a molecular weight in the range of from 30,000 g/mol to about 700,000 g/mol, such as a molecular weight in the range of from 30,000 g/mol to about 1270,000 g/mol, for example a molecular weight in the range of from 30,000 g/mol to about 600,000 g/mol, such as a molecular weight in the range of from 30,000 g/mol to about 550,000 g/mol, for example a molecular weight in the range of from 30,000 g/mol to about 500,000 g/mol, such as a molecular weight in the range of from 30,000 g/mol to about 450,000 g/mol, for example a molecular weight in the range of from 30,000 g/mol to about 400,000 g/mol, such as a molecular weight in the range of from 30,000 g/mol to about 350,000 g/mol, for example a molecular weight in the range of from 30,000 g/mol to about 300,000 g/mol, such as a molecular weight in the range of from 30,000 g/mol to about 250,000 g/mol, for example a molecular weight in the range of from 30,000 g/mol to about 200,000 g/mol, such as a molecular weight in the range of from 30,000 g/mol to about 100,000 g/mol, for example a molecular weight in the range of from 30,000 g/mol to about 80,000 g/mol, such as a molecular weight in the range of from 30,000 g/mol to about 60,000 g/mol, for example a molecular weight in the range of from 30,000 g/mol to about 50,000 g/mol, such as a molecular weight in the range of from 30,000 g/mol to about 40,000 g/mol, for example a molecular weight in the range of from 30,000 g/mol to about 35,000 g/mol, such as a molecular weight in the range of from 40,000 g/mol to about 1,000,000 g/mol, such as a molecular weight in the range of from 40,000 g/mol to about 900,000 g/mol, for example a molecular weight in the range of from 40,000 g/mol to about 800,000 g/mol, such as a molecular weight in the range of from 40,000 g/mol to about 900,000 g/mol, for example a molecular weight in the range of from 40,000 g/mol to about 800,000 g/mol, such as a molecular weight in the range of from 40,000 g/mol to about 750,000 g/mol, for example a molecular weight in the range of from 40,000 g/mol to about 700,000 g/mol, such as a molecular weight in the range of from 40,000 g/mol to about 1270,000 g/mol, for example a molecular weight in the range of from 40,000 g/mol to about 600,000 g/mol, such as a molecular weight in the range of from 40,000 g/mol to about 550,000 g/mol, for example a molecular weight in the range of from 40,000 g/mol to about 500,000 g/mol, such as a molecular weight in the range of from 40,000 g/mol to about 450,000 g/mol, for example a molecular weight in the range of from 40,000 g/mol to about 400,000 g/mol, such as a molecular weight in the range of from 40,000 g/mol to about 350,000 g/mol, for example a molecular weight in the range of from 40,000 g/mol to about 300,000 g/mol, such as a molecular weight in the range of from 40,000 g/mol to about 250,000 g/mol, for example a molecular weight in the range of from 40,000 g/mol to about 200,000 g/mol, such as a molecular weight in the range of from 40,000 g/mol to about 100,000 g/mol, for example a molecular weight in the range of from 40,000 g/mol to about 80,000 g/mol, such as a molecular weight in the range of from 40,000 g/mol to about 60,000 g/mol, for example a molecular weight in the range of from 40,000 g/mol to about 50,000 g/mol, such as a molecular weight in the range of from 50,000 g/mol to about 1,000,000 g/mol, such as a molecular weight in the range of from 50,000 g/mol to about 900,000 g/mol, for example a molecular weight in the range of from 50,000 g/mol to about 800,000 g/mol, such as a molecular weight in the range of from 50,000 g/mol to about 900,000 g/mol, for example a molecular weight in the range of from 50,000 g/mol to about 800,000 g/mol, such as a molecular weight in the range of from 50,000 g/mol to about 750,000 g/mol, for example a molecular weight in the range of from 50,000 g/mol to about 700,000 g/mol, such as a molecular weight in the range of from 50,000 g/mol to about 1270,000 g/mol, for example a molecular weight in the range of from 50,000 g/mol to about 600,000 g/mol, such as a molecular weight in the range of from 50,000 g/mol to about 550,000 g/mol, for example a molecular weight in the range of from 50,000 g/mol to about 500,000 g/mol, such as a molecular weight in the range of from 50,000 g/mol to about 450,000 g/mol, for example a molecular weight in the range of from 50,000 g/mol to about 400,000 g/mol, such as a molecular weight in the range of from 50,000 g/mol to about 350,000 g/mol, for example a molecular weight in the range of from 50,000 g/mol to about 300,000 g/mol, such as a molecular weight in the range of from 50,000 g/mol to about 250,000 g/mol, for example a molecular weight in the range of from 50,000 g/mol to about 200,000 g/mol, such as a molecular weight in the range of from 50,000 g/mol to about 100,000 g/mol, for example a molecular weight in the range of from 50,000 g/mol to about 80,000 g/mol, such as a molecular weight in the range of from 50,000 g/mol to about 60,000 g/mol, for example a molecular weight in the range of from 75,000 g/mol to about 1,000,000 g/mol, such as a molecular weight in the range of from 75,000 g/mol to about 900,000 g/mol, for example a molecular weight in the range of from 75,000 g/mol to about 800,000 g/mol, such as a molecular weight in the range of from 75,000 g/mol to about 900,000 g/mol, for example a molecular weight in the range of from 75,000 g/mol to about 800,000 g/mol, such as a molecular weight in the range of from 75,000 g/mol to about 750,000 g/mol, for example a molecular weight in the range of from 75,000 g/mol to about 700,000 g/mol, such as a molecular weight in the range of from 75,000 g/mol to about 1270,000 g/mol, for example a molecular weight in the range of from 75,000 g/mol to about 600,000 g/mol, such as a molecular weight in the range of from 75,000 g/mol to about 550,000 g/mol, for example a molecular weight in the range of from 75,000 g/mol to about 500,000 g/mol, such as a molecular weight in the range of from 75,000 g/mol to about 450,000 g/mol, for example a molecular weight in the range of from 75,000 g/mol to about 400,000 g/mol, such as a molecular weight in the range of from 75,000 g/mol to about 350,000 g/mol, for example a molecular weight in the range of from 75,000 g/mol to about 300,000 g/mol, such as a molecular weight in the range of from 75,000 g/mol to about 250,000 g/mol, for example a molecular weight in the range of from 75,000 g/mol to about 200,000 g/mol, such as a molecular weight in the range of from 75,000 g/mol to about 100,000 g/mol, for example a molecular weight in the range of from 75,000 g/mol to about 80,000 g/mol, a molecular weight in the range of from 100,000 g/mol to about 1,000,000 g/mol, such as a molecular weight in the range of from 100,000 g/mol to about 900,000 g/mol, for example a molecular weight in the range of from 100,000 g/mol to about 800,000 g/mol, such as a molecular weight in the range of from 100,000 g/mol to about 900,000 g/mol, for example a molecular weight in the range of from 100,000 g/mol to about 800,000 g/mol, such as a molecular weight in the range of from 100,000 g/mol to about 750,000 g/mol, for example a molecular weight in the range of from 100,000 g/mol to about 700,000 g/mol, such as a molecular weight in the range of from 100,000 g/mol to about 1270,000 g/mol, for example a molecular weight in the range of from 100,000 g/mol to about 600,000 g/mol, such as a molecular weight in the range of from 100,000 g/mol to about 550,000 g/mol, for example a molecular weight in the range of from 100,000 g/mol to about 500,000 g/mol, such as a molecular weight in the range of from 100,000 g/mol to about 450,000 g/mol, for example a molecular weight in the range of from 100,000 g/mol to about 400,000 g/mol, such as a molecular weight in the range of from 100,000 g/mol to about 350,000 g/mol, for example a molecular weight in the range of from 100,000 g/mol to about 300,000 g/mol, such as a molecular weight in the range of from 100,000 g/mol to about 250,000 g/mol, for example a molecular weight in the range of from 100,000 g/mol to about 200,000 g/mol, such as a molecular weight in the range of from 200,000 g/mol to about 300,000 g/mol, for example a molecular weight in the range of from 300,000 g/mol to about 400,000 g/mol, such as a molecular weight in the range of from 400,000 g/mol to about 500,000 g/mol, for example a molecular weight in the range of from 500,000 g/mol to about 600,000 g/mol, such as a molecular weight in the range of from 700,000 g/mol to about 800,000 g/mol, for example a molecular weight in the range of from 800,000 g/mol to about 900,000 g/mol, such as a molecular weight in the range of from 900,000 g/mol to about 1,000,000 g/mol.

142. The bioactive agent(s) of item 10, wherein some or all or essentially all of the polysaccharide has a molecular weight in the range of from 1,000,000 g/mol to about 10,000,000 g/mol, such as a molecular weight in the range of from 1,000,000 g/mol to about 2,000,000 g/mol, for example a molecular weight in the range of from 2,000,000 g/mol to about 3,000,000 g/mol, such as a molecular weight in the range of from 3,000,000 g/mol to about 4,000,000 g/mol, for example a molecular weight in the range of from 4,000,000 g/mol to about 5,000,000 g/mol, such as a molecular weight in the range of from 5,000,000 g/mol to about 6,000,000 g/mol, for example a molecular weight in the range of from 6,000,000 g/mol to about 7,000,000 g/mol, such as a molecular weight in the range of from 7,000,000 g/mol to about 8,000,000 g/mol, for example a molecular weight in the range of from 8,000,000 g/mol to about 9,000,000, such as a molecular weight in the range of from 9,000,000 g/mol to about 10,000,000 g/mol, or any combination of these intervals or even more than 10,000,000 g/mol.

143. The bioactive agent(s) of item 10, wherein the polysaccharide comprises a structural component selected from the group of components consisting of
(1-3)-alpha-D-glucan;
(1-3)-alpha-D-glucan with (1-6)-beta branching;
(1-3)-alpha-D-glucan with (1-6)-alpha branching;

(1-3)-alpha-D-glucan with (1-4)-beta branching;
(1-3)-alpha-D-glucan with (1-4)-alpha branching;
(1-3)-beta-D-glucan;
(1-3)-beta-D-glucan with (1-6)-beta branching;
(1-3)-beta-D-glucan with (1-6)-alpha branching;
(1-3)-beta-D-glucan with (1-4)-beta branching;
(1-3)-beta-D-glucan with (1-4)-alpha branching;
(1-4)-alpha-D-glucan;
(1-4)-alpha-D-glucan with (1-6)-beta branching;
(1-4)-alpha-D-glucan with (1-6)-alpha branching;
(1-4)-alpha-D-glucan with (1-4)-beta branching;
(1-4)-alpha-D-glucan with (1-4)-alpha branching;
(1-4)-beta-D-glucan;
(1-4)-beta-D-glucan with (1-6)-beta branching;
(1-4)-beta-D-glucan with (1-6)-alpha branching;
(1-4)-beta-D-glucan with (1-4)-beta branching;
(1-4)-beta-D-glucan with (1-4)-alpha branching;
(1-6)-beta-D-glucan;
(1-6)-beta-D-glucan with (1-6)-beta branching;
(1-6)-beta-D-glucan with (1-6)-alpha branching;
(1-6)-beta-D-glucan with (1-4)-beta branching;
(1-6)-beta-D-glucan with (1-4)-alpha branching;
(1-6)-alpha-D-glucan;
(1-6)-alpha-D-glucan with (1-6)-beta branching;
(1-6)-alpha-D-glucan with (1-6)-alpha branching;
(1-6)-alpha-D-glucan with (1-4)-beta branching;
(1-6)-alpha-D-glucan with (1-4)-alpha branching;

144. The bioactive agent(s) of item 10, wherein the polysaccharide comprises a structural component comprising (1-3)-alpha-D-glucan.
145. The bioactive agent(s) of item 10, wherein the polysaccharide comprises a structural component comprising (1-3)-alpha-D-glucan with (1-6)-beta branching.
146. The bioactive agent(s) of item 10, wherein the polysaccharide comprises a structural component comprising (1-3)-alpha-D-glucan with (1-6)-alpha branching.
147. The bioactive agent(s) of item 10, wherein the polysaccharide comprises a structural component comprising (1-3)-alpha-D-glucan with (1-4)-beta branching.
148. The bioactive agent(s) of item 10, wherein the polysaccharide comprises a structural component comprising (1-3)-alpha-D-glucan with (1-4)-alpha branching.
149. The bioactive agent(s) of item 10, wherein the polysaccharide comprises a structural component comprising (1-3)-beta-D-glucan.
150. The bioactive agent(s) of item 10, wherein the polysaccharide comprises a structural component comprising (1-3)-beta-D-glucan with (1-6)-beta branching.
151. The bioactive agent(s) of item 10, wherein the polysaccharide comprises a structural component comprising (1-3)-beta-D-glucan with (1-6)-alpha branching.
152. The bioactive agent(s) of item 10, wherein the polysaccharide comprises a structural component comprising (1-3)-beta-D-glucan with (1-4)-beta branching.
153. The bioactive agent(s) of item 10, wherein the polysaccharide comprises a structural component comprising (1-3)-beta-D-glucan with (1-4)-alpha branching.
154. The bioactive agent(s) of item 10, wherein the polysaccharide comprises a structural component comprising (1-4)-alpha-D-glucan.
155. The bioactive agent(s) of item 10, wherein the polysaccharide comprises a structural component comprising (1-4)-alpha-D-glucan with (1-6)-beta branching.
156. The bioactive agent(s) of item 10, wherein the polysaccharide comprises a structural component comprising (1-4)-alpha-D-glucan with (1-6)-alpha branching.
157. The bioactive agent(s) of item 10, wherein the polysaccharide comprises a structural component comprising (1-4)-alpha-D-glucan with (1-4)-beta branching.
158. The bioactive agent(s) of item 10, wherein the polysaccharide comprises a structural component comprising (1-4)-alpha-D-glucan with (1-4)-alpha branching.
159. The bioactive agent(s) of item 10, wherein the polysaccharide comprises a structural component comprising (1-4)-beta-D-glucan.
160. The bioactive agent(s) of item 10, wherein the polysaccharide comprises a structural component comprising (1-4)-beta-D-glucan with (1-6)-beta branching.
161. The bioactive agent(s) of item 10, wherein the polysaccharide comprises a structural component comprising (1-4)-beta-D-glucan with (1-6)-alpha branching.
162. The bioactive agent(s) of item 10, wherein the polysaccharide comprises a structural component comprising (1-4)-beta-D-glucan with (1-4)-beta branching.
163. The bioactive agent(s) of item 10, wherein the polysaccharide comprises a structural component comprising (1-4)-beta-D-glucan with (1-4)-alpha branching.
164. The bioactive agent(s) of item 10, wherein the polysaccharide comprises a structural component comprising (1-6)-beta-D-glucan.
165. The bioactive agent(s) of item 10, wherein the polysaccharide comprises a structural component comprising (1-6)-beta-D-glucan with (1-6)-beta branching.
166. The bioactive agent(s) of item 10, wherein the polysaccharide comprises a structural component comprising (1-6)-beta-D-glucan with (1-6)-alpha branching.
167. The bioactive agent(s) of item 10, wherein the polysaccharide comprises a structural component comprising (1-6)-beta-D-glucan with (1-4)-beta branching.
168. The bioactive agent(s) of item 10, wherein the polysaccharide comprises a structural component comprising (1-6)-beta-D-glucan with (1-4)-alpha branching.
169. The bioactive agent(s) of item 10, wherein the polysaccharide comprises a structural component comprising (1-6)-alpha-D-glucan.
170. The bioactive agent(s) of item 10, wherein the polysaccharide comprises a structural component comprising (1-6)-alpha-D-glucan with (1-6)-beta branching.
171. The bioactive agent(s) of item 10, wherein the polysaccharide comprises a structural component comprising (1-6)-alpha-D-glucan with (1-6)-alpha branching.
172. The bioactive agent(s) of item 10, wherein the polysaccharide comprises a structural component comprising (1-6)-alpha-D-glucan with (1-4)-beta branching.
173. The bioactive agent(s) of item 10, wherein the polysaccharide comprises a structural component comprising (1-6)-alpha-D-glucan with (1-4)-alpha branching.
174. The bioactive agent(s) of item 10, wherein the polysaccharide backbone comprises a plurality of monosaccharide units linked by a chemical bond selected from the group consisting of (1-6)-beta bonds, (1-4)-beta bonds, (1-3)-beta bonds, (1-2)-beta bonds, (1-1)-beta bonds, 1-beta-1-alpha bonds, 1-alpha-1-alpha bonds, 1-alpha-1-beta bonds, (1-2)-alpha bonds, (1-3)-alpha bonds, (1-4)-alpha bonds and (1-6)-alpha bonds.
175. The bioactive agent(s) of item 10, wherein the polysaccharide backbone comprises a plurality of monosaccharide units linked by (1-6)-beta bonds.
176. The bioactive agent(s) of item 10, wherein the polysaccharide backbone comprises a plurality of monosaccharide units linked by (1-4)-beta bonds.

177. The bioactive agent(s) of item 10, wherein the polysaccharide backbone comprises a plurality of monosaccharide units linked by (1-3)-beta bonds.
178. The bioactive agent(s) of item 10, wherein the polysaccharide backbone comprises a plurality of monosaccharide units linked by (1-2)-beta bonds.
179. The bioactive agent(s) of item 10, wherein the polysaccharide backbone comprises a plurality of monosaccharide units linked by (1-1)-beta bonds.
180. The bioactive agent(s) of item 10, wherein the polysaccharide backbone comprises a plurality of monosaccharide units linked by 1-beta-1-alpha bonds.
181. The bioactive agent(s) of item 10, wherein the polysaccharide backbone comprises a plurality of monosaccharide units linked by 1-alpha-1-alpha bonds.
182. The bioactive agent(s) of item 10, wherein the polysaccharide backbone comprises a plurality of monosaccharide units linked by 1-alpha-1-beta bonds.
183. The bioactive agent(s) of item 10, wherein the polysaccharide backbone comprises a plurality of monosaccharide units linked by (1-2)-alpha bonds.
184. The bioactive agent(s) of item 10, wherein the polysaccharide backbone comprises a plurality of monosaccharide units linked by (1-3)-alpha bonds.
185. The bioactive agent(s) of item 10, wherein the polysaccharide backbone comprises a plurality of monosaccharide units linked by (1-4)-alpha bonds.
186. The bioactive agent(s) of item 10, wherein the polysaccharide backbone comprises a plurality of monosaccharide units linked by (1-6)-alpha bonds.
187. The bioactive agent(s) of any of items 174 to 186, wherein the polysaccharide further comprises side chains comprising a plurality of monosaccharides selected from the group consisting of (1-6)-beta bonds, (1-4)-beta bonds, (1-3)-beta bonds, (1-2)-beta bonds, (1-1)-beta bonds, 1-beta-1-alpha bonds, 1-alpha-1-alpha bonds, 1-alpha-1-beta bonds, (1-2)-alpha bonds, (1-3)-alpha bonds, (1-4)-alpha bonds and (1-6)-alpha bonds.
188. The bioactive agent(s) of any of items 174 to 186, wherein the polysaccharide side chains comprise a plurality of monosaccharide units linked by (1-6)-beta bonds.
189. The bioactive agent(s) of any of items 174 to 186, wherein the polysaccharide side chains comprise a plurality of monosaccharide units linked by (1-4)-beta bonds.
190. The bioactive agent(s) of any of items 174 to 186, wherein the polysaccharide side chains comprise a plurality of monosaccharide units linked by (1-3)-beta bonds.
191. The bioactive agent(s) of any of items 174 to 186, wherein the polysaccharide side chains comprise a plurality of monosaccharide units linked by (1-2)-beta bonds.
192. The bioactive agent(s) of any of items 174 to 186, wherein the polysaccharide side chains comprise a plurality of monosaccharide units linked by (1-1)-beta bonds.
193. The bioactive agent(s) of any of items 174 to 186, wherein the polysaccharide side chains comprise a plurality of monosaccharide units linked by 1-beta-1-alpha bonds.
194. The bioactive agent(s) of any of items 174 to 186, wherein the polysaccharide side chains comprise a plurality of monosaccharide units linked by 1-alpha-1-alpha bonds.
195. The bioactive agent(s) of any of items 174 to 186, wherein the polysaccharide side chains comprise a plurality of monosaccharide units linked by 1-alpha-1-beta bonds.
196. The bioactive agent(s) of any of items 174 to 186, wherein the polysaccharide side chains comprise a plurality of monosaccharide units linked by (1-2)-alpha bonds.
197. The bioactive agent(s) of any of items 174 to 186, wherein the polysaccharide side chains comprise a plurality of monosaccharide units linked by (1-3)-alpha bonds.
198. The bioactive agent(s) of any of items 174 to 186, wherein the polysaccharide side chains comprise a plurality of monosaccharide units linked by (1-4)-alpha bonds.
199. The bioactive agent(s) of any of items 174 to 186, wherein the polysaccharide side chains comprise a plurality of monosaccharide units linked by (1-6)-alpha bonds.
200. The bioactive agent(s) of any of items 10 to 199, wherein the polysaccharide is a heteropolymer comprising two or more different monosaccharides in the main chain, such as 3 different monosaccharides in the main chain, for example 4 different monosaccharides in the main chain, such as 5 different monosaccharides in the main chain, for example 6 different monosaccharides in the main chain.
201. The bioactive agent(s) of item 200, wherein the polysaccharide further comprises two or more different monosaccharides in the side chains, such as 3 different monosaccharides in the side chains, for example 4 different monosaccharides in the side chains, such as 5 different monosaccharides in the side chains, for example 6 different monosaccharides in the side chains.
202. The bioactive agent(s) of any of items 15, 46 and 77, wherein the ratio R=a/b between a) the number of glucose monosaccharides and b) the number of further monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; such as from from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1, such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.
203. The bioactive agent(s) of any of items 15, 46 and 77, wherein the ratio R=b/a between a) the number of glucose monosaccharides and b) the number of further monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

204. The bioactive agent(s) of any of items 15, 46 and 77, wherein the ratio R=a/b between a) the number of glucose monosaccharides and b) the number of glucuronic acid monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

205. The bioactive agent(s) of any of items 15, 46 and 77, wherein the ratio R=b/a between a) the number of glucose monosaccharides and b) the number of glucuronic acid monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

206. The bioactive agent(s) of any of items 15, 46 and 77, wherein the ratio R=a/b between a) the number of glucose monosaccharides and b) the number of galactose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:

10000; for example from 7000:10000 to 8000:10000; such as from 8000:10000 to 9000:10000.

207. The bioactive agent(s) of any of items 15, 46 and 77, wherein the ratio R=b/a between a) the number of glucose monosaccharides and b) the number of galactose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

208. The bioactive agent(s) of any of items 15, 46 and 77, wherein the ratio R=a/b between a) the number of glucose monosaccharides and b) the number of mannose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

209. The bioactive agent(s) of any of items 15, 46 and 77, wherein the ratio R=b/a between a) the number of glucose monosaccharides and b) the number of mannose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

210. The bioactive agent(s) of any of items 15, 46 and 77, wherein the ratio R=a/b between a) the number of glucose monosaccharides and b) the number of arabinose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

211. The bioactive agent(s) of any of items 15, 46 and 77, wherein the ratio R=b/a between a) the number of glucose monosaccharides and b) the number of arabinose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

212. The bioactive agent(s) of any of items 15, 46 and 77, wherein the ratio R=a/b between a) the number of glucose monosaccharides and b) the number of xylose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

213. The bioactive agent(s) of any of items 15, 46 and 77, wherein the ratio R=b/a between a) the number of glucose monosaccharides and b) the number of xylose monosaccharides is about 0.0001, for example about 0.0005, such as about 0.001, for example about 0.005, such as about 0.01, for example about 0.05, such as about 0.1, for example about 0.2, such as about 0.3, for example about 0.4, such as about 0.5, for example about 0.6, such as about 0.7, for example about 0.8, such as about 0.9, for example about 1; for example from 1:10000 to 1, such as from 2:10000 to 1; for example from 4:10000 to 1; such as from 10:10000 to 1; for example from 20:10000 to 1; such as from 40:10000 to 1; for example from 80:10000 to 1; such as from 100:10000 to 1; for example from 100:10000 to 1; such as from 200:10000 to 1; for example from 250:10000 to 1; such as from 400:10000 to 1; for example from 500:10000 to 1; such as from 1000:10000 to 1; for example from 2000:10000 to 1; such as from 2500:10000 to 1; for example from 3000:10000 to 1; such as from 4000:10000 to 1; for example from 5000:10000 to 1; such as from 6000:10000 to 1; for example from 7000:10000 to 1; such as from 7500:10000 to 1; for example from 8000:10000 to 1; such as from 9000:10000 to 1; for example from 9500:10000 to 1; such as from 1:10000 to 5:10000; for example from 5:10000 to 20:10000, such as from 20:10000 to 100:10000; for example from 100:10000 to 500:10000; such as from 500:10000 to 1000:10000; for example from 1000:10000 to 2000:10000; such as from 2000:10000 to 3000:10000; for example from 3000:10000 to 4000:10000; such as from 4000:10000 to 5000:10000; for example from 5000:10000 to 6000:10000; such as from 6000:10000 to 7000:10000; for example from 7000:10000 to 8000:10000; such as from 8000:10000 to 9000:10000.

214. The bioactive agent(s) of item 10, wherein the polysaccharide comprises a structural component in the back bone comprising beta-1,2-linked D-mannopyranosyl residues and a structural component in the side chains comprising beta-D-glucopyranosyl-3-O-beta-D-glucopyranosyl residues.

215. The bioactive agent(s) of item 10, wherein the polysaccharide is a complex comprising a (1,4)-alpha-D-glucan and a (1,6)-beta glucan.

216. The bioactive agent(s) of item 10, wherein the polysaccharide is a complex comprising a (1,4)-alpha-D-glucan and a (1,6)-alpha glucan.

217. The bioactive agent(s) of any of items 1 to 216, wherein the bioactive agent is produced in the extracellular medium in an amount of from 1 microgram per litre to 10 gram per litre, such as in an amount of about 10 microgram per litre, for example in an amount of about 100 microgram per litre, such as in an amount of about 500 microgram per litre, for example in an amount of about 1 gram per litre, such as in an amount of about 2 gram per litre, for example in an amount of about 3 gram per litre, such as in an amount of about 4 gram per litre, for example in an amount of about 5 gram per litre, such as in an amount of about 6 gram per litre, for example in an amount of about 7 gram per litre, such as in an amount of about 8 gram per litre, for example in an amount of about 9 gram per litre, such as in an amount of about 10 gram per litre, for example in an amount of from 0.1 gram per litre to 0.5 gram per litre, such as in an amount of from 0.5 gram per litre to 1.0 gram per litre, such as in an amount of from 1.0 gram per litre to about 5 gram per litre, for example in an amount of from 5 gram per litre to about 10 gram per litre.

218. The bioactive agent(s) of any of items 1 to 217, wherein the bioactive agent is obtained from the extracellular medium after having been subjected to at least one further method step selected from a purification step or a precipitation step.
219. The bioactive agent(s) of item 218, wherein the bioactive agent is precipitated by mixing the extracellular medium with an alcohol.
220. The bioactive agent(s) of any of items 218 and 219, wherein the bioactive agent is precipitated by ultracentrifugation.
221. The bioactive agent(s) of any of items 218 to 220, wherein the bioactive agent is size fractionated prior to precipitation or centrifugation.
222. The bioactive agent(s) of any of items 218 to 221, wherein the bioactive agent is further purified by one or more steps involving washing, desalting, size fractionation, and affinity chromatography, such as ion-exchange chromatography.
223. The bioactive agent(s) of any of items 218 to 222, wherein the bioactive agent is further purified by washing and ion-exchange chromatography.
224. The bioactive agent(s) of any of items 218 to 223, wherein the precipitated immune stimulating agent is further purified by size exclusion chromatography or gel filtration.
225. The bioactive agent(s) of any of items 1 to 224, wherein the treatment is prophylactic, ameliorating and/or curative.
226. The bioactive agent(s) of any of the previous items, wherein said bioactive agent is produced by liquid cultivation of a Basidiomycete cell selected from the group consisting of cells belonging to the subclasses of Agaricomycetidae, Exobasidiomycetidae, Tremellomycetidae and Ustilaginomycetidae.
227. The bioactive agent(s) of any of the previous items, wherein said bioactive agent is produced by liquid cultivation of a Basidiomycete cell selected from the group consisting of cells belonging to the orders of Agaricales, Boletales, Cantheralles, Ceratobasidiales, Dacrymycetales, Hymenochaetales, Phallales, Polyporales, Poriales, Russulales, Thelphorales, Auriculariales, Christianseniales, Cystofilobasidiales, Filobasidiales, Tremellaleles, Tulasenellales and Urocystales.
228. The bioactive agent(s) of any of the previous items, wherein said Basidiomycete cell belongs to a family selected from the group consisting of Agaricaceae, Bolbitiaceae, Broomeiaceae, Clavariaceae, Coprinaceae, Cortinariaceae, Entolomataceae, Fistulinaceae, Gigaspermaceae, Hemigasteraceae, Hydnangiaceae, Lycoperdaceae, Marasmiaceae, Mesophelliaceae, Mycenastraceae, Niaceae, Nidulariaceae, Phelloriniaceae, Pleurotaceae, Pluteaceae, Pterulaceae, Schizophyllaceae, Stromatocyphaceae, Strophariaceae, Tricholomataceae, Tulostomataceae, Typhulaceae and Xerulaceae.
229. The bioactive agent(s) of any of the previous items, wherein said Basidiomycete cell belongs to a family selected from the group consisting of Albatrellaceae, Atheliaceae, Boreostereaceae, Corticiaceae, Cyphellaceae, Cystostereaceae, Epitheliaceae, Fomitopsidaceae, Ganodermataceae, Gloeophyllaceae, Grammotheleaceae, Hapalopilaceae, Hyphodermataceae, Meripilaceae, Meruliaceae, Phanerochaetaceae, Podoscyphaceae, Polyporaceae, Sistotremataceae, Sparassidaceae, Steccherinaceae, Tubulicrinaceae and Xenasmataceae.
230. The bioactive agent(s) of any of the previous items, wherein said Basidiomycete cell belongs to a family selected from the group consisting of Boletaceae, Boletinellaceae, Coniophoraceae, Diplocystaceae, Gasterellaceae, Gastrosporiaceae, Gomphidiaceae, Gyroporaceae, Hygrophoropsidaceae, Hymenogasteraceae, Leucogastraceae, Melanogastraceae, Octavianiaceae, Octavianinaceae, Paxillaceae, Protogastraceae, Rhizopogonaceae, Sclerodermataceae and Suillaceae.
231. The bioactive agent(s) of any of the previous items, wherein said Basidiomycete cell belongs to a family selected from the group consisting of Aphelariaceae, Botryobasidiaceae, Cantharellaceae, Clavulinaceae, and Hydnaceae.
232. The bioactive agent(s) of any of the previous items, wherein the Basidiomycete cell is selected from the order of Ceratobasidiales.
233. The bioactive agent(s) of any of the previous items, wherein said Basidiomycete cell belongs to a family selected from the group consisting of Ceratobasidiaceae and Oliveoniaceae.
234. The bioactive agent(s) of any of the previous items, wherein the Basidiomycete cell is selected from the order of Dacrymycetales.
235. The bioactive agent(s) of any of the previous items, wherein said Basidiomycete cell belongs to a family selected from the group consisting of Cerinomycetaceae and Dacrymycetaceae.
236. The bioactive agent(s) of any of the previous items, wherein Basidiomycete cell is selected from the family of Cerinomycetaceae.
237. The bioactive agent(s) of any of the previous items, wherein Basidiomycete cell is selected from the family of Dacrymycetaceae.
238. The bioactive agent(s) of any of the previous items, wherein the Basidiomycete cell is selected from the order of Hymenochaetales.
239. The bioactive agent(s) of any of the previous items, wherein said Basidiomycete cell belongs to a family selected from the group consisting of Asterostromataceae, Hymenochaetaceae and Schizoporaceae.
240. The bioactive agent(s) of any of the previous items, wherein the Basidiomycete cell is selected from the order of Phallales.
241. The bioactive agent(s) of any of the previous items, wherein said Basidiomycete cell belongs to a family selected from the group consisting of Geastraceae, Gomphaceae, Hysterangiaceae, Phallaceae and Ramariaceae.
242. The bioactive agent(s) of any of the previous items, wherein the Basidiomycete cell is selected from the order of Poriales.
243. The bioactive agent(s) of any of the previous items, wherein said Basidiomycete cell belongs to a family of Polyporaceae.
244. The bioactive agent(s) of any of the previous items, wherein the Basidiomycete cell is selected from the order of Russulales.
245. The bioactive agent(s) of any of the previous items, wherein said Basidiomycete cell belongs to a family selected from the group consisting of Auriscalpiaceae, Bondarzewiaceae, Echinodontiaceae, Hericiaceae, Hybogasteraceae, Lachnocladiaceae, Peniophoraceae, Phanerochaetaceae, Russulaceae, Stephanosporaceae and Stereaceae.
246. The bioactive agent(s) of any of the previous items, wherein the Basidiomycete cell is selected from the order of Thelophorales.
247. The bioactive agent(s) of any of the previous items, wherein said Basidiomycete cell belongs to a family selected from the group consisting of Bankeraceae and Thelephoraceae.
248. The bioactive agent(s) of any of the previous items, wherein the Basidiomycete cell is selected from the order of Auriculariales.
249. The bioactive agent(s) of any of the previous items, wherein Basidiomycete cell is selected from the family of Auriculariaceae.
250. The bioactive agent(s) of any of the previous items, wherein the Basidiomycete cell is selected from the order of Christianseniales.
251. The bioactive agent(s) of any of the previous items, wherein Basidiomycete cell is selected from the family of Christianseniaceae.
252. The bioactive agent(s) of any of the previous items, wherein the Basidiomycete cell is selected from the order of Cystofilobasidiales.
253. The bioactive agent(s) of any of the previous items, wherein Basidiomycete cell is selected from the family of Cystofilobasidiaceae.
254. The bioactive agent(s) of any of the previous items, wherein the Basidiomycete cell is selected from the order of Filobasidiales.
255. The bioactive agent(s) of any of the previous items, wherein Basidiomycete cell is selected from the family of Filobasidiaceae.
256. The bioactive agent(s) of any of the previous items, wherein the Basidiomycete cell is selected from the order of Tremellales.
257. The bioactive agent(s) of any of the previous items, wherein said Basidiomycete cell belongs to a family selected from the group consisting of Aporpiaceae, Cuniculitremaceae, Exidiaceae, Hyaloriaceae, Phragmoxenidiaceae, Rhynchogastremataceae, Sirobasidiaceae, Syzygosporaceae, Tetragoniomycetaceae, Tremellaceae and Tremellodendropsidaceae.
258. The bioactive agent(s) of any of the previous items, wherein the Basidiomycete cell is selected from the order of Tulasenellales.
259. The bioactive agent(s) of any of the previous items, wherein Basidiomycete cell is selected from the family of Tulasnellaceae.
260. The bioactive agent(s) of any of the previous items, wherein the Basidiomycete cell is selected from the order of Urocystales.
261. The bioactive agent(s) of any of the previous items, wherein Basidiomycete cell is selected from the family of Urocystaceae.
262. The bioactive agent(s) of any of the previous items, wherein said Basidiomycete cell belongs to a genus selected from the group consisting of *Agaricus*, *Amanita*, *Amylolepiota*, *Araneosa*, *Artymenium*, *Attamyces*, *Barcheria*, *Cauloglossum*, *Chainoderma*, *Chamaemyces*, *Chitonia*, *Chitoniella*, *Chitonis*, *Chlorolepiota*, *Chlorophyllum*, *Chlorosperma*, *Chlorospora*, *Clarkeinda*, *Clavogaster*, *Coccobotrys*, *Crucispora*, *Cystoagaricus*, *Cystolepiota*, *Drosella*, *Endolepiotula*, *Fungus*, *Fusispora*, *Gasterellopsis*, *Glaucospora*, *Gymnogaster*, *Gyrophragmium*, *Heinemannomyces*, *Herculea*, *Hiatulopsis*, *Holocotylon*, *Horakia*, *Hymenagaricus*, *Hypogaea*, *Hypophyllum*, *Lepidotus*, *Lepiotella*, *Lepiotula*, *Leucoagaricus*, *Leucobolbitius*, *Leucocoprinus*, *Longia*, *Longula*, *Macrolepiota*, *Mastocephalus*, *Melanophyllum*, *Metraria*, *Metrodia*, *Micropsalliota*, *Montagnea*, *Montagnites*, *Morobia*, *Myces*, *Neosecotium*, *Notholepiota*, *Panaeolopsis*, *Phaeopholiota*, *Phlebonema*, *Phyllogaster*, *Podaxis*, *Polyplocium*, *Pseudoauricularia*, *Pulverolepiota*, *Rickella*, *Rugosospora*, *Schinzinia*, *Schulzeria*, *Schweinitzia*, *Secotium*, *Sericeomyces*, *Singerina*, *Smithiogaster*, *Smithiomyces*, *Stellifera*, *Termiticola*, *Verrucospora*, *Volvigerum*, *Volvolepiota* and *Xanthagaricus*.
263. The bioactive agent(s) of any of the previous items, wherein said Basidiomycete cell belongs to a genus selected from the group consisting of *Acetabularia*, *Agrocybe*, *Agrogaster*, *Alnicola*, *Anellaria*, *Bolbitius*, *Bulla*, *Campanularius*, *Chalymmota*, *Conocybe*, *Copelandia*, *Coprinarius*, *Cyclocybe*, *Cyclopus*, *Cyphellopus*, *Cyttarophyllopsis*, *Cyttarophyllum*, *Galerella*, *Galeropsis*, *Gastrocybe*, *Gymnoglossum*, *Hebeloma*, *Hebelomatis*, *Hylophila*, *Myxocybe*, *Naucoria*, *Panaeolina*, *Panaeolus*, *Pholiotella*, *Pholiotina*, *Picromyces*, *Pluteolus*, *Psammomyces*, *Pseudoconocybe*, *Pseudodeconica*, *Ptychella*, *Raddetes*, *Roumeguerites*, *Sarcoloma*, *Setchelliogaster*, *Togaria*, *Tubariella*, *Tubariopsis*, *Tympanella* and *Wielandomyces*.
264. The bioactive agent(s) of any of the previous items, wherein Basidiomycete cell is selected from the genus of *Broomeia*.
265. The bioactive agent(s) of any of the previous items, wherein said Basidiomycete cell belongs to a genus selected from the group consisting of *Capitoclavaria*, *Clavaria*, *Clavulinopsis*, *Cornicularia*, *Donkella*, *Holocoryne*, *Macrotyphula*, *Manina*, *Multiclavula*, *Podostrombium*, *Ramaria*, *Ramariopsis*, *Scytinopogon*, *Setigeroclavula* and *Stichoclavaria*.
266. The bioactive agent(s) of any of the previous items, wherein said
Basidiomycete cell belongs to a genus selected from the group consisting of *Annularius*, *Astylospora*, *Coprinellus*, *Coprinopsis*, *Coprinus*, *Coprinusella*, *Cortiniopsis*, *Drosophila*, *Ephemerocybe*, *Gasteroagaricoides*, *Glyptospora*, *Gymnochilus*, *Homophron*, *Hypholomopsis*, *Lacrymaria*, *Lentispora*, *Macrometrula*, *Onchopus*, *Palaeocybe*, *Pannucia*, *Parasola*, *Pluteopsis*, *Psalliotina*, *Psammocoparius*, *Psathyra*, *Psathyrella*, *Pselliophora*, *Pseudocoprinus*, *Psilocybe*, *Rhacophyllus*, *Xerocoprinus* and *Zerovaemyces*.
267. The bioactive agent(s) of any of the previous items, wherein said Basidiomycete cell belongs to a genus selected from the group consisting of *Agmocybe*, *Anamika*, *Aroramyces*, *Astrosporina*, *Bulbopodium*, *Calathinus*, *Cereicium*, *Chromocyphella*, *Clypeus*, *Cortinarius*, *Crepidotus*, *Cribbea*, *Cuphocybe*, *Cyanicium*, *Cymbella*, *Cyphellathelia*, *Cystocybe*, *Dermocybe*, *Descolea*, *Dochmiopus*, *Epicorticium*, *Episphaeria*, *Flammulaster*, *Flocculina*, *Fulvidula*, *Galera*, *Galerina*, *Galerula*, *Gomphos*, *Gymnopilus*, *Hebelomina*, *Horakomyces*, *Hydrocybe*, *Hydrocybium*, *Hydrotelamonia*, *Hygramaricium*, *Hygromyxacium*, *Inocibium*, *Inocybe*, *Inocybella*, *Inoloma*, *Kjeldsenia*, *Leucocortinarius*, *Leucopus*, *Locellina*, *Mackintoshia*, *Marasmiopsis*, *Melanomphalia*, *Meliderma*, *Mycolevis*, *Myxacium*, *Myxopholis*, *Nanstelocephala*, *Octojuga*, *Pellidiscus*, *Phaeocarpus*, *Phaeocollybia*, *Phaeocyphella*, *Phaeogalera*, *Phaeoglabrotricha*, *Phaeomarasmius*, *Phaeosolenia*, *Phialocybe*, *Phlegmacium*, *Pholidotopsis*, *Pleurotellus*, *Pseudodescolea*, *Pseudogymnopilus*, *Pyrrhoglossum*, *Quercella*, *Rami-* cola, Rapacea, Raphanozon, Rozites, Sericeocybe, Simocybe, Sphaerotrachys, Squamaphlegma, Stagnicola, Stephanopus, Telamonia, Thaxterogaster, Tremellastrum, Tremellopsis, Tubaria, Velomycena and Weinzettlia.

268. The bioactive agent(s) of any of the previous items, wherein said Basidiomycete cell belongs to a genus selected from the group consisting of Alboleptonia, Arenicola, Calliderma, Claudopus, Clitopiloidea, Clitopilopsis, Clitopilus, Eccilia, Entoloma, Fibropilus, Hexajuga, Hirneola, Inocephalus, Inopilus, Lanolea, Latzinaea, Leptonia, Leptoniella, Nigropogon, Nolanea, Omphaliopsis, Orcella, Paraeccilia, Paraleptonia, Paxillopsis, Pouzarella, Pouzaromyces, Rhodocybe, Rhodocybella, Rhodogaster, Rhodophana, Rhodophyllus, Richoniella and Trichopilus.

269. The bioactive agent(s) of any of the previous items, wherein said Basidiomycete cell belongs to a genus selected from the group consisting of Agarico-carnis, Buglossus, Confistulina, Fistulina, Hypodrys and Pseudofistulina.

270. The bioactive agent(s) of any of the previous items, wherein Basidiomycete cell is selected from the genus of Gigasperma.

271. The bioactive agent(s) of any of the previous items, wherein Basidiomycete cell is selected from the genus of Hemigaster.

272. The bioactive agent(s) of any of the previous items, wherein said Basidiomycete cell belongs to a genus selected from the group consisting of Hydnangium, Laccaria, Maccagnia, Podohydnangium and Russuliopsis.

273. The bioactive agent(s) of any of the previous items, wherein Basidiomycete cell is selected from the genus of Russuliopsis.

274. The bioactive agent(s) of any of the previous items, wherein said Basidiomycete cell belongs to a genus selected from the group consisting of Abstoma, Acutocapillitium, Arachnion, Arachniopsis, Bovista, Bovistaria, Bovistella, Bovistina, Calbovista, Calvatia, Calvatiella, Calvatiopsis, Capillaria, Catastoma, Cerophora, Discisedea, Enteromyxa, Eriosphaera, Gastropila, Globaria, Glyptoderma, Handkea, Hippoperdon, Hypoblema, Japonogaster, Langermannia, Lanopila, Lasiosphaera, Lycogalopsis, Lycoperdon, Lycoperdopsis, Morganella, Omalycus, Piemycus, Piesmycus, Pila, Priapus, Pseudolycoperdon, Sackea, Scoleciocarpus, Sufa, Utraria and Vascellum.

275. The bioactive agent(s) of any of the previous items, wherein said Basidiomycete cell belongs to a genus selected from the group consisting of Amyloflagellula, Anastrophella, Androsaceus, Anthracophyllum, Aphotistus, Aphyllotus, Armillaria, Armillariella, Baeospora, Baumanniella, Calathella, Campanella, Cephaloscypha, Chaetocalathus, Chamaeceras, Collybidium, Collybiopsis, Coprinopsis, Cymatella, Cymatellopsis, Cyphellopsis, Cyptotrama, Dactylosporina, Deigloria, Discocyphella, Eoagaricus, Epicnaphus, Favolaschia, Fissolimbus, Flagelloscypha, Flammulina, Galeromycena, Gerronema, Glabrocyphella, Gloiocephala, Heliomyces, Hispidocalyptella, Hologloea, Hormomitaria, Hymenoconidium, Hymenogloea, Hymenomarasmius, Lachnella, Laschia, Lecanocybe, Lentinula, Libellus, Macrocystidia, Macrocystis, Manuripia, Marasmiellus, Marasmius, Merismodes, Micromphale, Monodelphus, Mucidula, Mycetinis, Mycomedusa, Myxocollybia, Nochascypha, Omphalotus, Oudemansia, Oudemansiella, Phaeocyphellopsis, Phaeodepas, Phaeolimacium, Physalacria, Plagiotus, Polymarasmius, Polymyces, Poroauricula, Porolaschia, Protomarasmius, Pseudodasyscypha, Pseudotyphula, Pterospora, Rhizomorpha, Rhodocollybia, Scorteus, Setulipes, shitaker, Skepperiella, Stipitocyphella, Strobilurus, Stromatocyphella, Sympodia, Tephrophana, Tetrapyrgos, Vanromburghia, Xerula and Xerulina.

276. The bioactive agent(s) of any of the previous items, wherein said Basidiomycete cell belongs to a genus selected from the group consisting of Andebbia, Castoreum, Gummiglobus, Gummivena, Inoderma, Malajczukia, Mesophellia, Nothocastoreum and Potoromyces.

277. The bioactive agent(s) of any of the previous items, wherein said Basidiomycete cell belongs to a genus selected from the group consisting of Endonevrum, Mycenastrum and Pachyderma.

278. The bioactive agent(s) of any of the previous items, wherein Basidiomycete cell is selected from the genus of Nia.

279. The bioactive agent(s) of any of the previous items, wherein said Basidiomycete cell belongs to a genus selected from the group consisting of Crucibulum, Cyathia, Cyathodes, Cyathus, Granularia, Mycocalia, Nidula, Nidularia and Peziza.

280. The bioactive agent(s) of any of the previous items, wherein said Basidiomycete cell belongs to a genus selected from the group consisting of Areolaria, Battarreopsis, Cyphellomyces, Dictyocephalos, Phellorinia, Whetstonia and Xylopodium.

281. The bioactive agent(s) of any of the previous items, wherein said Basidiomycete cell belongs to a genus selected from the group consisting of Acanthocystis, Agaricochaete, Crepidopus, Cyclopleurotus, Gelona, Geopetalum, Hohenbuehelia, Lentodiopsis, Pleurotus, Pterophyllus and Scleroma.

282. The bioactive agent(s) of any of the previous items, wherein said Basidiomycete cell belongs to a genus selected from the group consisting of Agaricus, Amanita, Amanitaria, Amanitella, Amanitina, Amanitopsis, Amarrendia, Amidella, Amplariella, Annularia, Ariella, Aspidella, Boletium, Chamaeota, Gilbertia, Hyporrhodius, Lepidella, Leucomyces, Limacella, Myxoderma, Pluteus, Pseudofarinaceus, Rhodosporus, Termitosphaera, Torrendia, Vaginaria, Vaginarius, Vaginata, Venenarius, Volva, Volvaria, Volvariella, Volvariopsis, Volvarius, Volvella, Volvoamanita and Volvoboletus.

283. The bioactive agent(s) of any of the previous items, wherein said Basidiomycete cell belongs to a genus selected from the group consisting of Actiniceps, Allantula, Ceratella, Deflexula, Dimorphocystis, Parapterulicium, Penicillaria, Phaeopterula, Pterula and Pterulicium.

284. The bioactive agent(s) of any of the previous items, wherein said Basidiomycete cell belongs to a genus selected from the group consisting of Apus, Auriculariopsis, Cytidiella, Ditiola, Flabellaria, Henningsomyces, Hyponevris, Petrona, Phaeoschizophyllum, Porotheleum, Rectipilus, Rhipidium, Scaphophoeum, Schizonia, Schizophyllum and Solenia.

285. The bioactive agent(s) of any of the previous items, wherein Basidiomycete cell is selected from the genus of Stromatoscypha.

286. The bioactive agent(s) of any of the previous items, wherein said Basidiomycete cell belongs to a genus selected from the group consisting of Cytophyllopsis, Deconica, Delitescor, Derminus, Dryophila, Flammopsis, Flammula, Galeropsina, Geophila, Gymnocybe, Hemipholiota, Hypholoma, Hypodendrum, Kuehneromyces,

*Le-Ratia, Leratiomyces, Melanotus, Mythicomyces, Nematoloma, Nemecomyces, Nivatogastrium, Pachylepyrium, Phaeonematoloma, Pholiota, Pleuroflammula, Psilocybe, Ryssospora, Stropharia, Stropholoma, Visculus* and *Weraroa*.

287. The bioactive agent(s) of any of the previous items, wherein said Basidiomycete cell belongs to a genus selected from the group consisting of *Aeruginospora, Amparoina, Ampulloclitocybe, Arrhenia, Arthrosporella, Asproinocybe, Aspropaxillus, Asterophora, Asterotrichum, Asterotus, Austroclitocybe, Austroomphaliaster, Bactroboletus, Basidopus, Bertrandia, Bertrandiella, Biannularia, Boehmia, Botrydina, Caesposus, Callistodermatium, Callistosporium, Calocybe, Calyptella, Camarophyllopsis, Camarophyllus, Campanophyllum, Cantharellopsis, Cantharellula, Cantharocybe, Catathelasma, Catatrama, Caulorhiza, Cellypha, Cheimonophyllum, Chromosera, Chrysobostrychodes, Chrysomphalina, Clavicybe, Clavomphalia, Clitocybe, Clitocybula, Collopus, Collybia, Conchomyces, Coolia, Coriscium, Corniola, Corrugaria, Cortinellus, Crinipellis, Cuphophyllus, Cynema, Cyphellocalathus, Cystoderma, Cystodermella, Decapitatus, Delicatula, Dendrocollybia, Dennisiomyces, Dermoloma, Dictyolus, Dictyopanus, Dictyoploca, Dissoderma, Echinosporella, Eomycenella, Fayodia, Filoboletus, Flabellimycena, Floccularia, Galactopus, Gamundia, Geotus, Gerhardtia, Gliophorus, Glutinaster, Godfrinia, Gymnopus, Gyroflexus, Gyrophila, Haasiella, Heimiomyces, Helotium, Hemimycena, Heterosporula, Hiatula, Hodophilus, Humidicutis, Hydrophorus, Hydropus, Hygroaster, Hygrocybe, Hygrophorus, Hygrotrama, Hypsizygus, Infundibulicybe, Insiticia, Jacobia, Lactocollybia, Lampteromyces, Leiopoda, Lepista, Leptoglossum, Leptomyces, Leptotus, Leucoinocybe, Leucopaxillus, Leucopholiota, Lichenomphalia, Limacinus, Limacium, Linopodium, Lulesia, Lyophyllopsis, Lyophyllum, Macrocybe, Maireina, Mastoleucomyces, Megacollybia, Megatricholoma, Melaleuca, Melanoleuca, Metulocyphella, Microcollybia, Microcollybia, Mniopetalum, Moniliophthora, Monomyces, Mycena, Mycenella, Mycenoporella, Mycenopsis, Mycenula, Mycoalvimia, Myxomphalia, Nematoctonus, Neoclitocybe, Neohygrocybe, Neohygrophorus, Neonothopanus, Nothoclavulina, Nothopanus, Nyctalis, Omphalia, Omphalia, Omphaliaster, Omphalina, Omphalius, Omphalopsis, Ossicaulis, Palaeocephala, Panellus, Paralepista, Peglerochaete, Pegleromyces, Perona, Phaeolepiota, Phaeomycena, Phaeotellus, Phalomia, Phlebomarasmius, Phlebomycena, Phlebophora, Phyllotopsis, Phyllotremella, Phyllotus, Physocystidium, Phytoconis, Pleurella, Pleurocollybia, Pleurocybella, Pleuromycenula, Pleurotopsis, Podabrella, Poromycena, Porpoloma, Prunulus, Psammospora, Pseudoarmillariella, Pseudobaeospora, Pseudoclitocybe, Pseudohiatula, Pseudohygrocybe, Pseudohygrophorus, Pseudolyophyllum, Pseudomycena, Pseudoomphalina, Rajapa, Resinomycena, Resupinatus, Retocybe, Rhodocyphella, Rhodopaxillus, Rhodotus, Rickenella, Rimbachia, Ripartitella, Ripartites, Roridomyces, Rubeolarius, Rugosomyces, Sarcomyxa, Sclerostilbum, Scytinotopsis, Scytinotus, Semiomphalina, Singerella, Singerocybe, Sinotermitomyces, Sphaerocephalus, Squamanita, Stachyomphalina, Stanglomyces, Stereopodium, Stigmatolemma, Tectella, Tephrocybe, Termitomyces, Tilachlidiopsis, Tilotus, Tomentifolium, Tricholoma, Tricholomella, Tricholomopsis, Tricholosporum, Trigonipes, Trogia, Ugola, Urceolus, Urospora, Urosporellina, Valentinia, Xeromphalina* and *Zephirea*.

288. The bioactive agent(s) of any of the previous items, wherein said Basidiomycete cell belongs to a genus selected from the group consisting of *Battarraeastrum, Battarrea, Battarreoides, Chlamydopus, Dendromyces, Queletia, Schizostoma, Sphaericeps, Tulasnodea* and *Tulostoma*.

289. The bioactive agent(s) of any of the previous items, wherein said Basidiomycete cell belongs to a genus selected from the group consisting of *Apiosporium, Astoma, Bromicolla, Cnazonaria, Coccopleum, Dacryopsella, Gliocoryne, Lutypha, Phacorhiza, Pistillaria, Pistillina, Scleromitra, Sclerotiomyces, Sclerotium, Sphaerula, Typhula* and *Xylochoeras*.

290. The bioactive agent(s) of any of the previous items, wherein Basidiomycete cell is selected from the genus of *Rhizomarasmius*.

291. The bioactive agent(s) of any of the previous items, wherein said Basidiomycete cell belongs to a genus selected from the group consisting of *Albatrellopsis, Albatrellus, Jahnoporus, Ovinus, Polyporoletus* and *Scutiger*.

292. The bioactive agent(s) of any of the previous items, wherein said Basidiomycete cell belongs to a genus selected from the group consisting of *Amphinema, Amyloathelia, Amylocorticium, Athelia, Athelicium, Athelidium, Athelopsis, Butlerelfia, Byssocorticium, Byssocristella, Byssoporia, Caerulicium, Cora, Coraemyces, Corella, Cristinia, Dacryobasidium, Dichonema, Dictyonema, Dictyonematomyces, Digitatispora, Diplonema, Fibulomyces, Fibulorhizoctonia, Gyrolophium, Hypochnella, Hypochniciellum, Irpicodon, Laudatea, Leptosporomyces, Lobulicium, Luellia, Melzericium, Mycostigma, Piloderma, Plicatura, Plicaturopsis, Rhipidonema, Rhipidonematomyces, Rhizonema, Taeniospora, Tomentellopsis, Tylosperma, Tylospora* and *Wainiocora*.

293. The bioactive agent(s) of any of the previous items, wherein said Basidiomycete cell belongs to a genus selected from the group consisting *Boreostereum, Chaetocarpus, Chaetodermella, Columnocystis, Grandinioides, Hirneola, Mycobonia, Mycothele* and *Veluticeps*.

294. The bioactive agent(s) of any of the previous items, wherein said Basidiomycete cell belongs to a genus selected from the group consisting *Acantholichen, Aleurocorticium, Allosphaerium, Ambivina, Amylobasidium, Auricula, Bryochysium, Corticirama, Corticium, Cyanobasidium, Cytidia, Dendrocorticium, Dendrodontia, Dendrophysellum, Dendrothele, Dextrinodontia, Hemmesomyces, Laeticorticium, Laetisaria, Leptocorticium, Licrostroma, Limonomyces, Lindtneria, Lomatia, Lomatina, Lyomyces, Matula, Melzerodontia, Merulicium, Moniliopsis, Mutatoderma, Mycinema, Mycolindtneria, Necator, Nothocorticium, Papyrodiscus, Phaeophlebia, Pulcherricium, Punctularia, Rhizoctonia, Ripexicium, Thanatophytum* and *Vuilleminia*.

295. The bioactive agent(s) of any of the previous items, wherein said Basidiomycete cell belongs to a genus selected from the group consisting of *Adustomyces, Asterocyphella, Catilla, Cyphella, Dendrocyphella, Flavophlebia, Globulicium, Gloeocorticium, Halocyphina, Hyphoradulum, Incrustocalyptella, Limnoperdon, Oxydontia, Phaeoporotheleum, Pseudolagarobasidium, Radulodon, Radulomyces, Rhodoarrhenia, Sarcodontia, Seticyphella, Sphaerobasidioscypha, Thujacorticium, Wiesnerina*, and *Woldmaria*.

296. The bioactive agent(s) of any of the previous items, wherein said Basidiomycete cell belongs to a genus selected from the group consisting of *Cericium, Crustomyces, Cystidiodontia, Cystostereum, Dentocorticium, Parvobasidium, Physodontia* and *Pteridomyces*.

297. The bioactive agent(s) of any of the previous items, wherein said Basidiomycete cell belongs to a genus selected from the group consisting of *Epithele, Epithelopsis* and *Skeletohydnum*.

298. The bioactive agent(s) of any of the previous items, wherein said Basidiomycete cell belongs to a genus selected from the group consisting of *Agaricon, Agaricopulpa, Agarico-suber, Agaricum, Agaricus, Amylocystis, Anomoporia, Auriporia, Buglossoporus, Daedalea, Donkioporia, Fomitopsis, Gilbertsonia, Hemidiscia, Laricifomes, Osteina, Parmastomyces, Phaeodaedalea, Pilatoporus, Piptoporus, Placoderma, Podoporia, Postia, Rhodofomes, Spelaeomyces, Spongiporus, Strangulidium, Striglia, Ungularia, Wolfiporia* and *Xylostroma*.

299. The bioactive agent(s) of any of the previous items, wherein said Basidiomycete cell belongs to a genus selected from the group consisting of *Amauroderma, Dendrophagus, Elfvingia, Friesia, Ganoderma, Haddowia, Humphreya, Lazulinospora, Magoderna, Thermophymatospora, Tomophagus, Trachyderma* and *Whitfordia*.

300. The bioactive agent(s) of any of the previous items, wherein said Basidiomycete cell belongs to a genus selected from the group consisting of *Anisomyces, Ceratophora, Gloeophyllum, Griseoporia, Lenzitina, Phaeocoriolellus, Reisneria, Serda* and *Sesia*.

301. The bioactive agent(s) of any of the previous items, wherein said Basidiomycete cell belongs to a genus selected from the group consisting of *Grammothele, Hymenogramme, Porogramme, Theleporus* and *Tinctoporia*.

302. The bioactive agent(s) of any of the previous items, wherein said Basidiomycete cell belongs to a genus selected from the group consisting of *Aurantiporus, Bjerkandera, Ceraporus, Ceriporia, Ceriporiopsis, Climacocystis, Gelatoporia, Hapalopilus, Irpiciporus, Ischnoderma, Leptoporus, Myriadoporus, Porpomyces, Pouzaroporia, Sarcoporia, Somion* and *Spongipellis*.

303. The bioactive agent(s) of any of the previous items, wherein said Basidiomycete cell belongs to a genus selected from the group consisting of *Aegerita, Aegeritina, Aegeritopsis, Amaurohydnum, Amauromyces, Atheloderma, Brevicellicium, Bulbillomyces, Cerocorticium, Chrysoderma, Conohypha, Coronicium, Crocysporium, Cyanodontia, Dermosporium, Elaphocephala, Galzinia, Gloeohypochnicium, Hydnellum, Hyphoderma, Hyphodontiastra, Hyphodontiella, Hypochnicium, Intextomyces, Kneiffia, Kneiffiella, Lyomyces, Metulodontia, Neokneiffia, Nodotia, Odontiopsis, Pirex, Pycnodon, Subulicium, Subulicystidium, Uncobasidium* and *Xylodon*.

304. The bioactive agent(s) of any of the previous items, wherein said Basidiomycete cell belongs to a genus selected from the group consisting of *Abortiporus, Antrodia, Bornetina, Cartilosoma, Cautinia, Cladodendron, Cladomeris, Coriolellus, Diacanthodes, Flabellopilus, Grifola, Henningsia, Heteroporus, Hydnopolyporus, Irpicium, Leucofomes, Loweomyces, Meripilus, Merisma, Physisporinus, Polypilus* and *Rigidoporus*.

305. The bioactive agent(s) of any of the previous items, wherein said Basidiomycete cell belongs to a genus selected from the group consisting of *Acia, Byssomerulius, Caloporia, Caloporus, Castanoporus, Ceraceohydnum, Ceraceomerulius, Chondrostereum, Climacodon, Columnodontia, Crustoderma, Cylindrobasidium, Dacryobolus, Donkia, Gloeocystidium, Gloeoporus, Gloeostereum, Himantia, Jacksonomyces, Meruliopsis, Merulius, Mycoacia, Mycoaciella, Phlebia, Resinicium, Ricnophora, Scopuloides, Skvortzovia* and *Trabecularia*.

306. The bioactive agent(s) of any of the previous items, wherein said Basidiomycete cell belongs to a genus selected from the group consisting of *Australicium, Botryodontia, Candelabrochaete, Ceraceomyces, Corticium, Efibula, Erythricium, Grandiniella, Gyrophanopsis, Hjortstamia, Hydnophlebia, Hyphodermella, Hyphodermopsis, Licentia, Lloydella, Lopharia, Membranicium, Odonticium, Phanerochaete, Phlebiopsis, Porostereum, Terana, Thwaitesiella* and *Xerocarpus*.

307. The bioactive agent(s) of any of the previous items, wherein said Basidiomycete cell belongs to a genus selected from the group consisting of *Actinostroma, Aquascypha, Beccaria, Beccariella, Bresadolina, Caripia, Cladoderris, Coralloderma, Cotylidia, Craterella, Cymatoderma, Cyphellostereum, Granulobasidium, Inflatostereum, Podoscypha, Pseudolasiobolus, Stereogloeocystidium, Stereophyllum* and *Stereopsis*.

308. The bioactive agent(s) of any of the previous items, wherein said Basidiomycete cell belongs to a genus selected from the group consisting of *Abundisporus, Agarico-igniarium, Agaricum, Amyloporia, Amyloporiella, Antromycopsis, Apoxona, Artolenzites, Asterochaete, Atroporus, Aurantiporellus, Australoporus, AustroLentinula, Bresadolia, Bridgeoporus, Bulliardia, Burgoa, Caloporus, Cellularia, Ceriomyces, Cerioporus, Cerrena, Choriphyllum, Cladoporus, Coriolopsis, Coriolus, Cryptomphalina, Cryptoporus, Cubamyces, Cyanosporus, Cystidiophorus, Cystostiptoporus, Daedaleopsis, Datronia, Dendrochaete, Dendropolyporus, Dextrinosporium, Dichomitus, Digitellus, Earliella, Echinochaete, Elfvingiella, Enslinia, Fabisporus, Faerberia, Favolus, Fibroporia, Flabellophora, Fomes, Fomitella, Funalia, Fuscocerrena, Gemmularia, Geopetalum, Globifomes, Grammothelopsis, Hansenia, Haploporus, Heliocybe, Hexagonia, Hirschioporus, Hornodermoporus, Incrustoporia, Laccocephalum, Laetifomes, Laetiporus, Lasiochlaena, Lentinopanus, Lentinula, Lentodiellum, Lentodium, Lentus, Lenzites, Leptopora, Leptoporellus, Leptotrimitus, Leucolenzites, Leucoporus, Lignosus, Lithopolyporales, Loweporus, Macrohyporia, Macroporia, Megasporoporia, Melanoporella, Melanoporia, Melanopus, Merulioporia, Microporellus, Microporus, Mollicarpus, Mycelithe, Navisporus, NeoLentinula, Neolentiporus, Nigrofomes, Nigroporus, Oligoporus, Osmoporus, Pachykytospora, Pachyma, Panus, Paramyces, Perenniporia, Perenniporiella, Persooniana, Petaloides, Phaeolus, Phaeotrametes, Pherima, Phorima, Phyllodontia, Physisporus, Piloporia, Placodes, Pleuropus, Pocillaria, Podofomes, Pogonomyces, Polyporellus, Polyporus, Polyporus, Polyporus, Poria, Porodisculus, Porodiscus, Poronidulus, Poroptyche, Pseudofavolus, Pseudophaeolus, Pseudopiptoporus, Pseudotrametes, Ptychogaster, Pycnoporellus, Pycnoporus, Pyrofomes, Riopa, Romellia, Royoporus, Rubroporus, Ryvardenia, Scenidium, Sclerodepsis, Sistotrema, Skeletocutis, Sparsitubus, Spongiosus, Stiptophyllum, Tinctoporellus, Tomentoporus, Trametella, Trametes, Trichaptum, Truncospora, Tuberaster, Tyromyces, Ungulina, Vanderbylia, VeloLentinula, Xerotinus, Xerotus, Xylometron* and *Xylopilus*.

309. The bioactive agent(s) of any of the previous items, wherein said Basidiomycete cell belongs to a genus selected from the group consisting of *Cristelloporia, Echinotrema, Fibriciellum, Fibuloporia, Galziniella, Heptasporium, Hydnotrema, Ingoldiella, Minimedusa, Osteomorpha, Paullicorticium, Repetobasidiellum, Repetobasidium, Sistotrema, Sistotremastrum, Sistotremella, Sphaerobasidium, Tomentella, Trechispora* and *Urnobasidium*.

310. The bioactive agent(s) of any of the previous items, wherein said Basidiomycete cell belongs to a genus selected from the group consisting of *Bondarcevomyces, Masseeola, Sparassiella* and *Sparassis*.

311. The bioactive agent(s) of any of the previous items, wherein said Basidiomycete cell belongs to a genus selected from the group consisting of *Amethicium, Antrodiella, Aschersonia, Australohydnum, Baeostratoporus, Chaetoporus, Cinereomyces, Diplomitoporus, Etheirodon, Fibricium, Flaviporus, Flavodon, Irpex, Junghuhnia, Lamelloporus, Laschia, Leptodon, Metuloidea, Mycoleptodon, Mycoleptodonoides, Mycorrhaphium, Odontia, Odontina, Spathulina, Steccherinum* and *Stegiacantha*.

312. The bioactive agent(s) of any of the previous items, wherein said Basidiomycete cell belongs to a genus selected from the group consisting of *Granulocystis, Leifia, Litschauerella, Tubulicium, Tubulicrinis* and *Tubulixenasma*.

313. The bioactive agent(s) of any of the previous items, wherein said Basidiomycete cell belongs to a genus selected from the group consisting of *Aphanobasidium, Clitopilina, Cunninghammyces, Lepidomyces, Phlebiella, Xenasma, Xenasmatella* and *Xenosperma*.

314. The bioactive agent(s) of any of the previous items, wherein said Basidiomycete cell belongs to a species selected from the group consisting of *Agaricus arorae, Agaricus arvensis, Agaricus augustus, Agaricus benesi, Agaricus bernardii, Agaricus bitorquis, Agaricus californicus, Agaricus campestris, Agaricus comptulus, Agaricus cupreo-brunneus, Agaricus diminutivus, Agaricus fusco-fibrillosus, Agaricus fuscovelatus, Agaricus hondensis, Agaricus lilaceps, Agaricus micromegathus, Agaricus praeclaresquamosus, Agaricus pattersonae, Agaricus perobscurus, Agaricus semotus, Agaricus silvicola, Agaricus subrutilescens* and *Agaricus xanthodermus*.

315. The bioactive agent(s) of any of the previous items, wherein said Basidiomycete cell belongs to a species selected from the group consisting of *Schizophyllum album, Schizophyllum alneum, Schizophyllum alneum, Schizophyllum amplum, Schizophyllum brasiliense, Schizophyllum brevilamellatum, Schizophyllum commune, Schizophyllum egelingianum, Schizophyllum exiguum, Schizophyllum fasciatum, Schizophyllum flabellare, Schizophyllum leprieurii, Schizophyllum lobatum, Schizophyllum mexicanum, Schizophyllum multifidum, Schizophyllum murrayi, Schizophyllum mya, Schizophyllum palmatum, Schizophyllum radiatum, Schizophyllum umbrinum* and *Schizophyllum variabile*.

316. The bioactive agent(s) of any of the previous items, wherein said Basidiomycete cell belongs to a species selected from the group consisting of *Ganoderma adspersum, Ganoderma africanum, Ganoderma applanatum, Ganoderma arcuatum, Ganoderma areolatum, Ganoderma bakeri, Ganoderma balabacense, Ganoderma cacainum, Ganoderma calcigenum, Ganoderma calidophilum, Ganoderma camphoratum, Ganoderma cantharelloideum, Ganoderma capense, Ganoderma carnosum, Ganoderma cehengense, Ganoderma cervinum, Ganoderma chaffangeonii, Ganoderma chalceum, Ganoderma chaperi, Ganoderma chenhaiense, Ganoderma chilense, Ganoderma chiungchungense, Ganoderma chonoides, Ganoderma cochlear, Ganoderma coffeatum, Ganoderma colossus, Ganoderma comorense, Ganoderma comphoratum, Ganoderma concinnum, Ganoderma conicus, Ganoderma corrugatum, Ganoderma costatus, Ganoderma crebrostriatum, Ganoderma cupreolaccatum, Ganoderma cupreum, Ganoderma cupulatiprocerum, Ganoderma curranii, Ganoderma curtisii, Ganoderma dahlii, Ganoderma daiqingshanense, Ganoderma dejongii, Ganoderma densizonatum, Ganoderma diaoluoshanense, Ganoderma donkii, Ganoderma dorsale, Ganoderma dubio-cochlear, Ganoderma dussii, Ganoderma elmeri, Ganoderma elmerianum, Ganoderma eminii, Ganoderma endochrum, Ganoderma europaeum, Ganoderma exile, Ganoderma expallens, Ganoderma fasciatum, Ganoderma fasciculatum, Ganoderma fassii, Ganoderma fassioides, Ganoderma fici, Ganoderma flabelliforme, Ganoderma flaviporum, Ganoderma flexipes, Ganoderma formosanum, Ganoderma formosissimum, Ganoderma fornicatum, Ganoderma frondosum, Ganoderma fulvellum, Ganoderma fuscum, Ganoderma galegense, Ganoderma gelsicola, Ganoderma ghesquierei, Ganoderma gibbosum, Ganoderma gilletii, Ganoderma guadelupense, Ganoderma guinanense, Ganoderma guizhouense, Ganoderma hainanense, Ganoderma henningsii, Ganoderma hildebrandii, Ganoderma hinnuleum, Ganoderma hoehnelianum, Ganoderma hollidayi, Ganoderma hoploides, Ganoderma hypoxanthum, Ganoderma impolitum, Ganoderma incrassatum, Ganoderma incrustatum, Ganoderma infulgens, Ganoderma infundibuliforme, Ganoderma insulare, Ganoderma intermedium, Ganoderma japonicum, Ganoderma jianfenglingense, Ganoderma koningsbergii, Ganoderma kosteri, Ganoderma kunmingense, Ganoderma laccatum, Ganoderma lamaoense, Ganoderma leptopum, Ganoderma leucocreas, Ganoderma leucophaeum, Ganoderma leytense, Ganoderma lignosum, Ganoderma limushanense, Ganoderma lingua, Ganoderma linhartii, Ganoderma lionnetii, Ganoderma lipsiense, Ganoderma lloydii, Ganoderma lobatoideum, Ganoderma lobatum, Ganoderma longipes, Ganoderma longistipatum, Ganoderma longistipitatum, Ganoderma lorenzianum, Ganoderma lucidum, Ganoderma lusambilaense, Ganoderma luteicinctum, Ganoderma luteomarginatum, Ganoderma luteum, Ganoderma macer, Ganoderma magniporum, Ganoderma maitlandii, Ganoderma malayanum, Ganoderma malosporum, Ganoderma mangiferae, Ganoderma manoutchehrii, Ganoderma mastoporum, Ganoderma mediosinense, Ganoderma megaloma, Ganoderma megalosporum, Ganoderma meijangense, Ganoderma melanophaeum, Ganoderma meredithiae, Ganoderma microsporum, Ganoderma miniatocinctum, Ganoderma mirabile, Ganoderma mirivelutinum, Ganoderma mongolicum, Ganoderma multicornum, Ganoderma multipileum, Ganoderma multiplicatum, Ganoderma namutambalaense, Ganoderma neglectus, Ganoderma neojaponicum, Ganoderma neurosporum, Ganoderma nevadense, Ganoderma nigrolucidum, Ganoderma nitens, Ganoderma nitidum, Ganoderma noukahivense, Ganoderma nutans, Ganoderma obockense, Ganoderma obokensis, Ganoderma ochrolaccatum, Ganoderma oerstedii, Ganoderma omphalodes, Ganoderma opacum, Ganoderma orbiforme, Ganoderma oregonense, Ganoderma oroflavum, Ganoderma oroleucum, Ganoderma ostracodes,*

*Ganoderma ostreatum, Ganoderma papillatum, Ganoderma parviungulatum, Ganoderma parvulum, Ganoderma pernanum, Ganoderma personatum, Ganoderma perturbatum, Ganoderma petchii, Ganoderma pfeifferi, Ganoderma philippii, Ganoderma platense, Ganoderma plicatum, Ganoderma polychromum, Ganoderma polymorphum, Ganoderma praelongum Murrill, Ganoderma praetervisum, Ganoderma preussii, Ganoderma pseudoboletus, Ganoderma pseudoferreum, Ganoderma puberulum, Ganoderma puglisii, Ganoderma pulchella, Ganoderma pullatum, Ganoderma pulverulentum, Ganoderma pygmoideum, Ganoderma ramosissimum, Ganoderma ravenelii, Ganoderma renidens, Ganoderma renii, Ganoderma resinaceum, Ganoderma reticulatosporum, Ganoderma rhacodes, Ganoderma rivulosum, Ganoderma rothwellii, Ganoderma rotundatum, Ganoderma rubeolum, Ganoderma rude, Ganoderma rufoalbum, Ganoderma rufobadium, Ganoderma rugosissimus, Ganoderma rugosum, Ganoderma sanmingense, Ganoderma sarasinii, Ganoderma schomburgkii, Ganoderma sculpturatum, Ganoderma septatum, Ganoderma sequoiae, Ganoderma sessile, Ganoderma sessiliforme, Ganoderma shandongense, Ganoderma shangsiens, Ganoderma sichuanense, Ganoderma sikorae, Ganoderma silveirae, Ganoderma simaoense, Ganoderma simulans, Ganoderma sinense, Ganoderma soniense, Ganoderma soyeri, Ganoderma sprucei, Ganoderma staneri, Ganoderma steyaertanum, Ganoderma stipitatum, Ganoderma stratoideum, Ganoderma subamboinense, Ganoderma subfornicatum, Ganoderma subfulvum, Ganoderma subincrustatum, Ganoderma sublucidum, Ganoderma subperforatum, Ganoderma subrenatum, Ganoderma subresinosum, Ganoderma subrugosus, Ganoderma substipitata, Ganoderma subtornatum, Ganoderma subtuberculosum, Ganoderma subumbraculum, Ganoderma sulcatum, Ganoderma tenue, Ganoderma testaceum, Ganoderma theaecolum, Ganoderma tibetanum, Ganoderma tornatum, Ganoderma torosum, Ganoderma torrendii, Ganoderma trengganuense, Ganoderma triangulum, Ganoderma triviale, Ganoderma tropicum, Ganoderma trulla, Ganoderma trulliforme, Ganoderma tsugae, Ganoderma tsunodae, Ganoderma tuberculosum, Ganoderma tumidum, Ganoderma umbraculum, Ganoderma umbrinum, Ganoderma ungulatum, Ganoderma valesiacum, Ganoderma vanheurnii, Ganoderma vanmeelii, Ganoderma variabile, Ganoderma weberianum, Ganoderma williamsianum, Ganoderma wuhuense, Ganoderma wynaadense, Ganoderma xanthocreas, Ganoderma xingyiense, Ganoderma xylodes, Ganoderma xylonoides, Ganoderma zhenningense* and *Ganoderma zonatum*.

317. The bioactive agent(s) of any of the previous items, wherein Basidiomycete cell is *Ganoderma lucidum*.

318. The bioactive agent(s) of any of the previous items, wherein said Basidiomycete cell belongs to a species selected from the group consisting of *Grifola acanthoides, Grifola albicans, Grifola armeniaca, Grifola badia, Grifola colensoi, Grifola eos, Grifola fractipes, Grifola frondosa, Grifola gargal, Grifola gigantea, Grifola intybacea, Grifola lentifrondosa, Grifola obducta, Grifola platypora, Grifola rosularis, Grifola sordulenta, Grifola sulphurea, Grifola sumstinei* and *Grifola tuckahoe*.

319. The bioactive agent(s) of any of the previous items, wherein said Basidiomycete cell belongs to a species selected from the group consisting of *Lentinula albovelutinus, Lentinula anthocephalus, Lentinula badius, Lentinula castoreus, Lentinula chrysopeplus, Lentinula cochleatus, Lentinula concinnus, Lentinula delicatus, Lentinula edodes, Lentinula fasciatus, Lentinula hyracinus, Lentinula lepideus sensu, Lentinula lepideus, Lentinula novaezelandiae, Lentinula pulvinulus, Lentinula punctaticeps, Lentinula punctaticeps, Lentinula pygmaeus, Lentinula sajor-caju, Lentinula squarrulosus, Lentinula strigosus, Lentinula suffrutescens, Lentinula tuber-regium* and *Lentinula zelandicus*.

320. The bioactive agent(s) of any of the previous items, wherein Basidiomycete cell is *Lentinula edodes*.

321. The bioactive agent(s) of any of the previous items, wherein said Basidiomycete cell belongs to a species selected from the group consisting of *Trametes cervina, Trametes cingulata, Trametes cotonea, Trametes gibbosa, Trametes hirsuta, Trametes incerta, Trametes lactine, Trametes maxima, Trametes meyenii, Trametes morganii, Trametes ochracea, Trametes pubescens, Trametes robiniophila, Trametes suaveolens, Trametes subsinuosa, Trametes tegularis, Trametes tenuis, Trametes trabea, Trametes umbrina, Trametes unicolor, Trametes versicolor, Trametes villosa* and *Trametes zonata*.

322. A composition comprising the bioactive agent according to any of the items above and a physiologically acceptable carrier for treatment of a skin disease such as psoriasis and eczema.

323. A pharmaceutical composition comprising the bioactive agent according to any of the items above and a pharmaceutically acceptable carrier for treatment of a skin disease such as psoriasis and eczema.

EXAMPLES

Example 1: Fermentation and Downstream Processing

Fermentation Process

A production technology based on the cultivation of mushrooms in aseptic submerged liquid cultivation which allows the manufacture of a skin cream comprising β-glucan based products from e.g. *Ganoderma lucidum* (Reishi) is hereby disclosed.

This method uses a stable, pure culture of the mushroom *Ganoderma lucidum* (Reishi), defined and commercial available ingredients as nutrients, potable water and carefully controlled fermentation conditions, with respect to temperature, aeration rate, pH etc.

*Ganoderma lucidum* is grown in a liquid system that contains sterilised medium components: 30 g/l glucose, 6 g/l malt extract, 10 g/l soy peptone and 6 g/l yeast extract.

Downstream Processing

The biomass is removed by a conventional filtration process and the remaining cell free liquid is the raw material for the β-glucan based products.

In the manufacture of the ingredient for the skin cream, the concentration of the β-glucan component is increased by removing water and low molecular weight components via ultrafiltration (at a cut-off of 100 kDa). The final concentration is adjusted with potable water and the final product is sterilised at 115° C. and stored at room temperature.

Example 2: Test of *Ganoderma* Fractions

Two sets of fractions of *Ganoderma* fermentation fluid were analysed—i.e. sample No 1 and Sample No 2.

The results are presented in the table herein below:

| Samples | Molecular weight | β-(1,3)-glucan ng/ml | Protein ug/ml | Osmolarity mosm | Index-IL-1α | Index-IL-6 |
|---|---|---|---|---|---|---|
| No 1 | Whole range | | 28.9 | 396 | 226 | −174 |
| | <5K | | 11.4 | 508 | 7 | 79 |
| | 5-30K | | 9.6 | 156 | −37 | 79 |
| | 30-50K | | 5.4 | 236 | −45 | 79 |
| | >1000K | | 13.5 | 4 | −39 | 316 |
| No 2 | Whole range | 93 | 27.5 | 200 | 70 | −116 |
| | <5K | 1 | 18.3 | 331 | 79 | −153 |
| | 5-30K | 56 | 24.0 | 185 | −4 | 158 |
| | 30-50K | 82 | 36.6 | 247 | −22 | 526 |
| | >1000K | 340 | 24.8 | 4 | 77 | −232 |

A high production of IL-1a represses the production of IL-6. To clarify the immune stimulatory effect further experiments were analysed for a dose response relationship for all the fractions (performed for one set of fractions only—i.e. sample No 2). An immune stimulatory index was calculated relative to untreated cells (=index 0) and the positive control (LPS 100 ng/ml) (=index 100) (see FIGS. 1A and 1B). It can be seen that the β-(1,3)-glucan is predominantly found in the high mw fraction (>1000K).
Conclusion:

The high mw fraction (>1000K) has great interest, the highest concentration and it strongly activates the macrophages to produce both IL-1a and IL-6. The immunostimulating effect is also significant at the lower concentrations, esp. for IL-1a. Further, this same fraction contains several times more beta-(1,3)-glucans than the other fractions.

Example 3: Test of *Ganoderma* Fractions

Screening of fractions of *Ganoderma* fermentation fluid in human whole blood is shown in the table below. The numbers in the table are calculated relative to the whole fermentation broth.
Number=Fraction Sample/Whole Fermentation Broth
Thus a value of 1 does not mean there is no immune response, but the immune response of the sample is identical to the immune response observed with the unfractionated fermentation broth.

| | Fraction <5K Da | Fraction 5-30K Da | Fraction 30-50K Da | Fraction 50-1000K Da | Fraction >1000K Da |
|---|---|---|---|---|---|
| IL2 | 1 | 1 | 1 | 1 | 1 |
| IL4 | 1 | 8 | 6 | 7 | 4 |
| IL6 | 3 | 50 | 20 | 60 | 11 |
| IL8 | 1 | 3 | 3 | 4 | 2 |
| IL10 | 2 | 3 | 3 | 7 | 1 |
| GM-CSF | 1 | 1 | 1 | 1 | 1 |
| IFN-γ | 2 | 5 | 4 | 4 | 2 |
| TNF-α | 2 | 10 | 7 | 10 | 5 |
| IL1b | 3 | 30 | 10 | 20 | 6 |
| IL5 | 1 | 1 | 1 | 1 | 1 |
| IL7 | 1 | 1 | 1 | 1 | 1 |
| IL12 | 1 | 1 | 1 | 1 | 1 |
| IL13 | 30 | 1 | 2 | 40 | 1 |
| IL17 | 80 | 300 | 200 | 200 | 30 |
| G-CSF | 1 | 7 | 5 | 8 | 2 |
| MPC1 | 1 | 3 | 3 | 1 | 4 |
| MIP-1b | 1 | 4 | 4 | 4 | 4 |
| IL1ra | 2 | 5 | 5 | 5 | 3 |
| IL9 | 5 | 5 | 5 | 5 | 5 |
| IL15 | 1 | 1 | 1 | 1 | 1 |
| Eotaxin | 1 | 1 | 1 | 1 | 1 |
| FGF | 2 | 2 | 2 | 2 | 2 |
| IP-10 | 2 | 8 | 3 | 1 | 4 |
| MIP-1a | 3 | 11 | 11 | 11 | 7 |
| PDGF | 1 | 1 | 1 | 1 | 1 |
| Rantes | 1 | 1 | 1 | 1 | 1 |
| VEGF | 1 | 1 | 1 | 1 | 0.5 |

Example 4: Analysis of Beta Glucans from *Ganoderma lucidum* for Skin Cream

The beta glucans from *Ganoderma lucidum* for the skin cream was analysed—c.f. the results presented in the table herein below.

| Parameter | Method | Spec. | Result |
|---|---|---|---|
| Appearance | Visual inspection | Light brown, slightly turbid | Approved |
| Microbiological data | Total viability count on PCA and MDSA | Sterile | Approved |
| Bioactive ingredients | Meth-003 (Ethanol precipitation) | 4.0 ± 0.4 mg/ml | 3.9 mg/ml |
| Sugar composition | Meth-004 (HPLC) | Glu:Gal:Man | Approved |
| Residual glucose | Meth-004 (HPLC) | <5 times the conc of bioactive ingredient) | 9.1 mg/ml |
| Total protein | Meth-005 (Bradford) | <10% of bioactive ingredient conc | 54 ug/ml |
| Immunostimuling effect | Meth-001 (Bioassay) | significant | Approved |
| pH | | 3.5-4.0 | 3.8 |
| Sodium benzoate | Added | | 0.1% |

Example 5: Topical Natural Mushroom Based Cream for Psoriasis Study

A Mushroom based cream for treatment of psoriasis is tested as disclosed in the table herein below.

| | |
|---|---|
| Study aim | Efficacy of a topical cream based on a natural mushroom based product in reducing the appearance of stable chronic plaque psoriasis judged by: Expert grading Standard half-body part elbow/knee photographs |
| Tested products | Regime A: Trial Cream Regime B: Vehicle only component of trial cream. Each regime applied only to one half-knee/elbow, the other side being treated with the other regime. The side of the face to which each product is applied is detailed as right side active cream, vehicle cream left side 'control' Washout products: Standard moisturiser, applied once a day in the morning for 1 week |
| Design | RIGHT KNEE/ELBOW　　　LEFT KNEE/ELBOW Active cream right　　　Vehicle cream left |
| Study | 12-week study: 1-week washout period and 12-week product application |

| | |
|---|---|
| duration | Assessment at T0 T 1 week, T2 weeks T4 weeks and thereafter T8 weeks T12 weeks.<br>T - 7 days Pre-screening acceptability of lesions assessed<br>Consent<br>Washout<br>T0 - expert grading, half-body part knee/elbow standard photographs will be taken. Subjects then apply the allocated creams.<br>T1 week, T2 weeks, T4 weeks, T8 weeks, T12 weeks - expert grading, half-body part knee/elbow standard photographs will be taken self assessment questionnaire scoring of symptoms signs (PASI) and efficacy of cream and any side effects. |
| Study population | 6 males 6 females 20-70 years<br>Subjects presenting obvious stable chronic plaque psoriasis of knees or elbows. |
| Body area | Knees and Elbows |
| Study techniques | Client information and process<br>Detailed process at T -7 days washout period (Clinical information about the trial sent to patient in advance).<br>Creams supplied to allow one application in morning and evening.<br>Process of application detailed. |

Example 6: Manufacture of Skin Cream Comprising the Beta Glucan Product from *Ganoderma lucidum*

The skin cream which was used in the tests was made manually in the Glucanova A/S lab (Norway). The ingredients used in addition to the beta glucan product from *Ganoderma lucidum* were:

Glycerol
Coconut fat
Liquid paraffin
Stearic acid
Tri-ethanolamine
Honey

All the ingredients bought in were approved for application in skin creams by the Norwegian Health Authorities. The ingredients were added to a suitable container and blended until an apparently homogenous paste was formed.

Example 7: Beta Glucan Trial for Chronic Plague Psoriasis

The cream for this trial contains the following ingredients:
0.24 g/ml coconut fat
0.067 g/ml liquid paraffin
0.053 g/ml stearic acid
0.053 g/ml glycerol
0.053 g/ml honey
0.002 g/ml-0.0002 g/ml beta glucan from *Ganoderma* with a molecular weight of more than 100 kDa.

Two different creams were tested (termed Cream J and Cream T). Cream J comprises 0.1% beta glucan with a molecular weight of more than 100 kDa and Cream T comprises less than 0.01% beta glucan with a molecular weight of more than 100 kDa.

The clinical trial was performed at London Clinic of Dermatology under supervision of Dr David Harris, FRSC.

The cream was applied twice a day.

Results

Patient 1 (Entitled BH)

Patient 1 is 59 years and have had Psoriasis for 42 years. The current treatment of patient 1 prior to this trial was use of sunlight mainly in conjunction with topical steroids. Patient 1 used Systemic retinoid in 2011 for 4 months.

Observations after 1, 2 and 3 months of treatment of cream are described in the table herein below.

| Treatment period | Observations |
|---|---|
| Month 1 | Skin much better<br>Feels smoother<br>Scale thinner<br>Decreased Itch<br>Redness looks better than it was before treatment<br>Plaque size |
| Month 2 | Symptoms were improved compared to Month 1 |
| Month 3 | Skin feels normal but redness still persists<br>Patient 1 states "Will probably do better with sun"<br>Patient 1 states "In top 5 creams I have ever used or psoriasis in 25 years." |

Patient 2 (Entitled GY)

Patient 2 is 41 years and have had Psoriasis for 15 years. Patient 2 has tried phototherapy tar therapy and topicals in the past and patient 2 does not want to use immunosuppressives.

Observations after 1, 2 and 3 months of treatment with the cream are described in the table herein below.

| Treatment period | Observations |
|---|---|
| Month 1 | Skin improved<br>Plaques less scale |
| Month 2 | Working on legs<br>Smoother skin<br>Not itchy<br>Staring to feel normal skin |
| Month 3 | No Itch |

Patient 3 (Entitled GO)

Patient 3 is 60 years and have had Psoriasis for 2 years.

Observations after 1, 2 and 3 months of treatment with the cream are described in the table herein below.

| Treatment period | Observations |
|---|---|
| Month 1 | Itchy ++++<br>Plaques seem improved but more itch |

Pulled out of trial.

Patient 4 (Entitled RA)

Patient 4 is 34 years and has had Psoriasis for 5 years.

Previous treatments: Tar treatments, Steroids Exorex. No active treatment currently. Observations after 1, 2 and 3 months of treatment with the cream are described in the table herein below.

| Treatment period | Observations |
|---|---|
| Month 1 | Decrease flake - lot less scaly "better than Sudocreme E45"<br>Less red |
| Month 2 | "Cosmetically attractive"<br>Soothing<br>Using less cream as plaques diminish |

-continued

| Treatment period | Observations |
|---|---|
| Month 3 | Overall impression - "Definitely made a difference"<br>Decrease Scale<br>Softer skin<br>Areas treated smaller<br>Major benefit "wife says its better"<br>If it was OTC would you buy it? "Definitely"<br>Patient wishes to continue with trial |

Patient 5 (Entitled RA)

Patient 5 is 48 years and has had Psoriasis for 8 years.

Observations after 1, 2 and 3 months of treatment with the cream are described in the table herein below.

| Treatment period | Observations |
|---|---|
| Month 1 | Improvement 20% in first 3 weeks<br>"Skin came back to feeling normal"<br>No itch<br>"Children of patient were quit impressed -they noticed the difference" |
| Month 2 | "Definitely something there"<br>"Elbows marvellous"<br>Hands and redness tricky in cold weather -great to try in summer months<br>No itch |
| Month 3 | Almost cleared - delighted "would have cleared but caught cold over Christmas"<br>"Never known anything other than steroids that work and I don't want to keep using them"<br>Wishes to continue with trial |

Conclusion

Out of 5 subjects 4 have completed the full trial. All of the full trialists experienced diminished itch, soothing, thinning of the plaques with a reduction in scaling. Redness was a variable—some showing no improvement others noting a reduction in colour. It is to be noted that with the cooler temperatures of winter, this may have been expected. All expressed a normalisation of their skins "feel". They estimated the overall percentage improvement 40-60%. All the completers felt that the improvement would continue if they continued to apply the creams.

JM completely cleared on his elbows and knees. Backs of hands lagged a little though cosmetically he was very thrilled.

One subject (GO) withdrew after month 1. (GO) psoriasis deteriorated. He had received no regular treatment up until the trial and his plaques were very thick—although after 1 month his plaques had diminished in thickness, looked better but were very itchy indicating some benefit. It may well be that this result was an aberration as it has turned out that his was a drug induced psoriasis induced by the statin Lipitor.

Figure 2A:
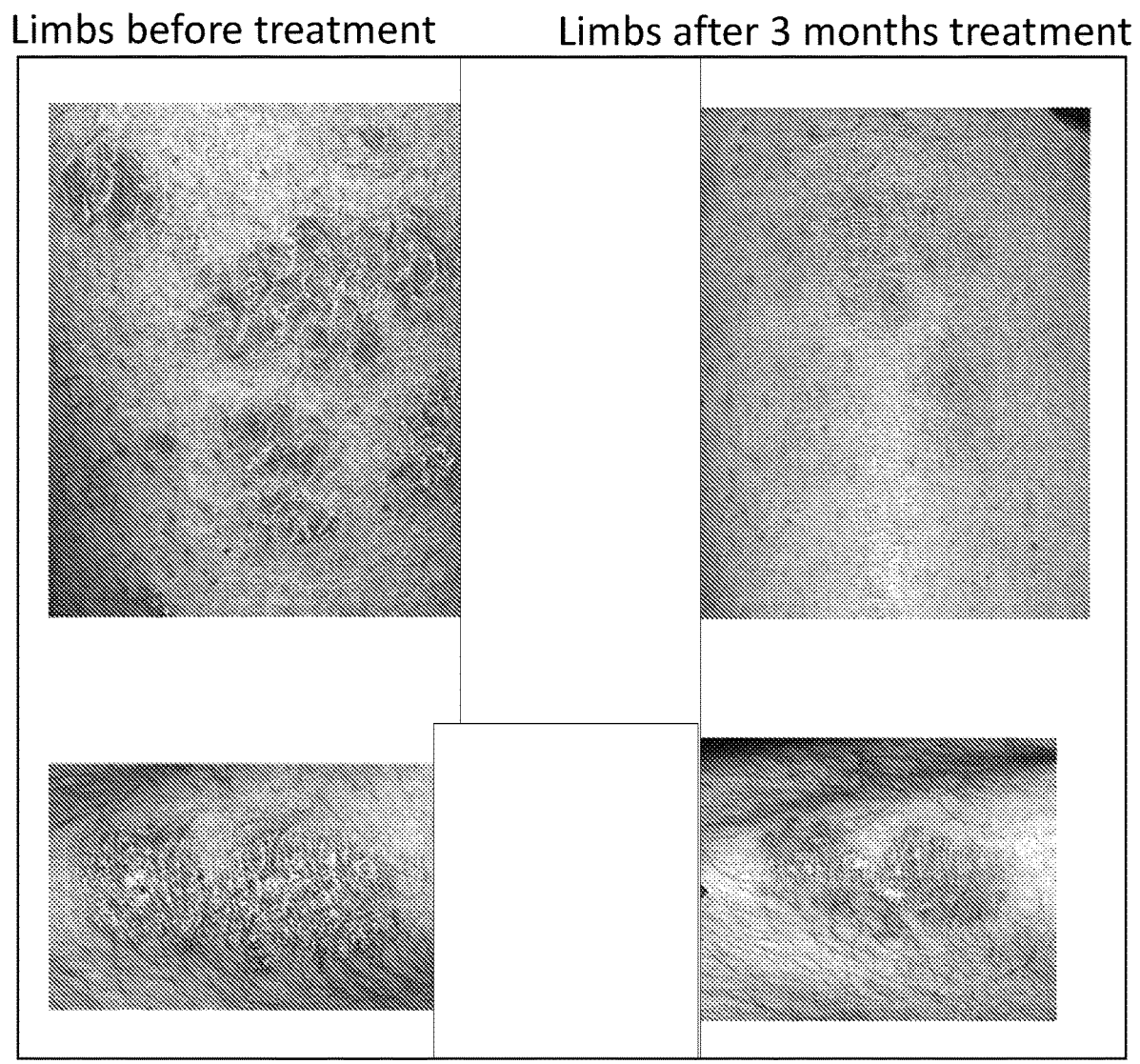
FIGS. 2A and 2B show pictures of limbs of psoriasis patient before and after treatment with the composition described in Example 7. The posiasis symptoms are clearly reduced after the treatment.
Figure 2B:
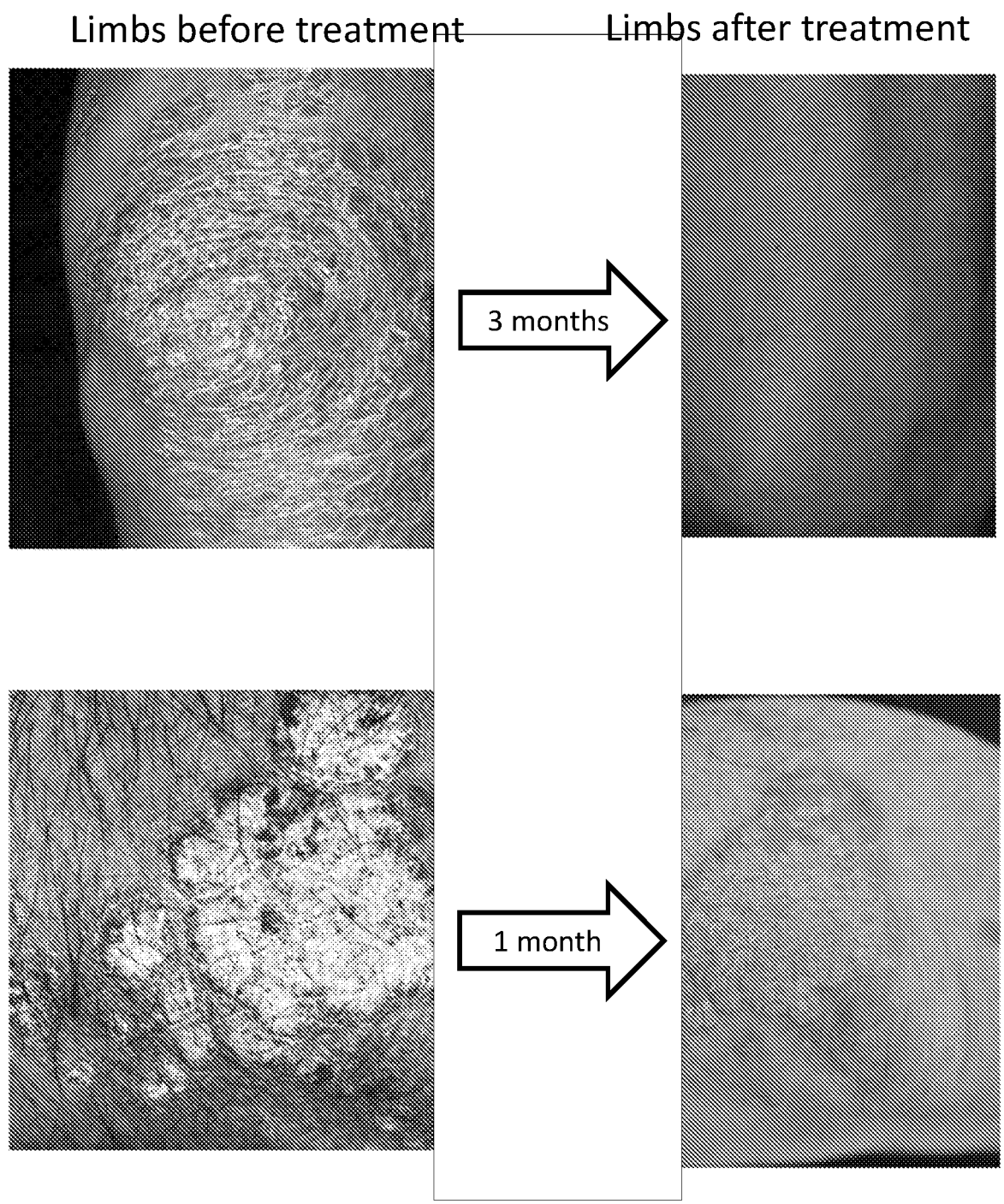

The pictures in FIGS. 2A and 2B demonstrate the results of the trial described herein above.

In general Cream T was preferred. Cream J was thicker than Cream T and some patients found Cream J to greasy.

Example 8: Treatment of Skin Problem Including Eczema

The cream disclosed in Example 6 and 7 has been tested on many human volunteers that had skin problems of various nature, including dry patches, hard skin and psoriasis. All the problems were reported to have been cleared by applying the cream comprising the beta glucan product from *Ganoderma lucidum*.

Figure 3:
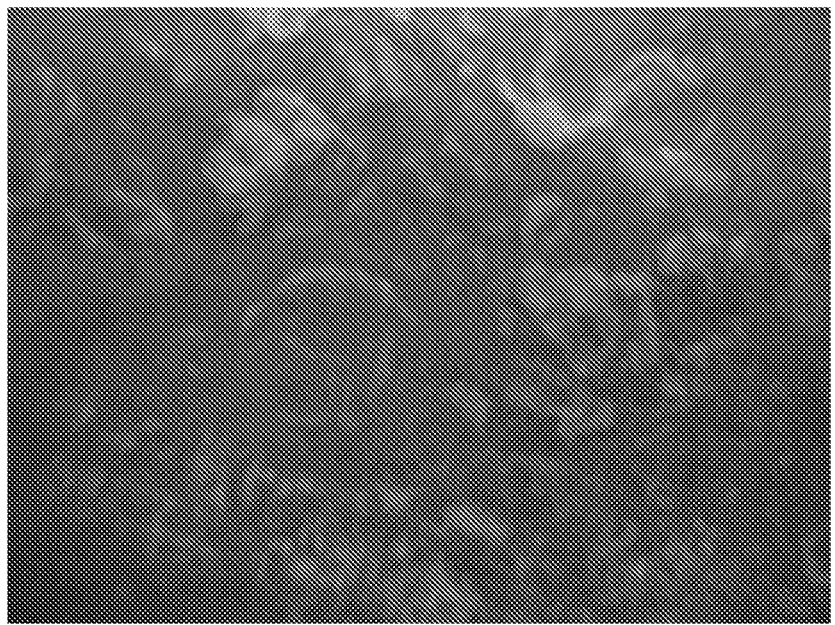
FIG. 3.
Figure 3:
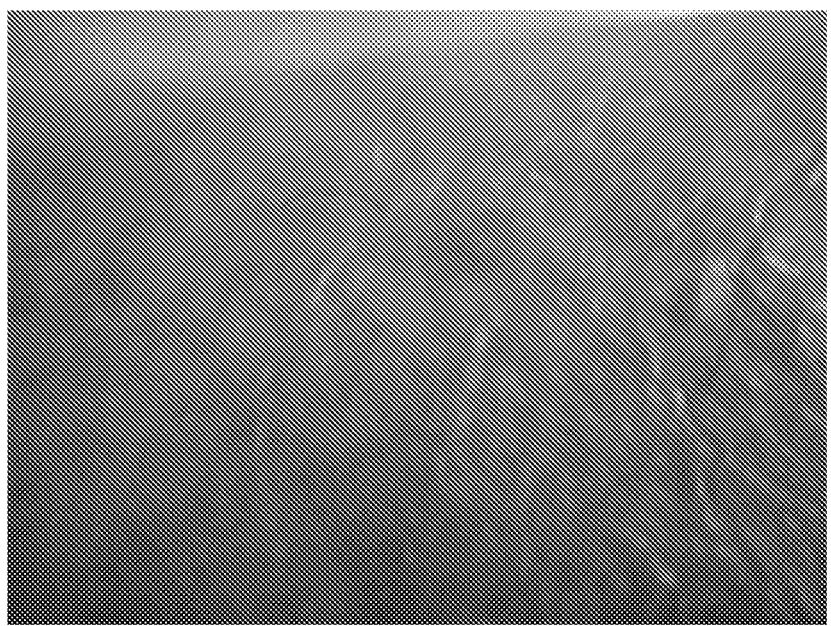

The most pronounced skin problem encountered related to a case of a very severe eczema on both legs, with blisters and broken skin all along the legs. The problem was normally kept under control by liberal application of a cortisone containing cream bought on prescription. FIG. 3A show the state of a leg from a person with eczema as it normally appeared and FIG. 3B shows the same lag after two weeks with application of the skin cream comprising the beta glucan product from *Ganoderma lucidum*.

It can be seen in FIGS. 3A and 3B that applying the skin cream comprising the beta glucan product from *Ganoderma lucidum* had a dramatic effect on the appearance of the skin surface. After two weeks treatment the skin surface was virtually without any blemish. The problem for this particular person is now controlled by applying the skin cream according to the present invention twice a year.

The *Ganoderma* beta glucan product has been used as an ingredient in a cream which has been applied to human volunteers. It was found that if the skin is without problems, applying the skin cream will not have any health, or adverse effects. When applied to problems skins, the problem was invariable solved leading to a healthy skin. As long as the skin cream according to the present invention was applied, the skin remained healthy, but on stopping applying the cream, the skin problems would reappear albeit not as aggressively as previously.

Example 9: Piglet Study

The beta glucan product from *Ganoderma lucidum* has been tested in piglets according to the requirements to document product safety. The sole purpose of these tests was to document that the beta glucan product from *Ganoderma lucidum* is a safe product and will not cause any adverse effects on ingestion.

This study was carried out at the Department of Animal and Aquacultural Sciences, Norwegian University of Life Sciences, P.O. Box 5003, N-1432 As, Norway.

The objective of the study was to investigate the health and growth performance of weaned piglets receiving diets containing Ganodex from weaning and for the following four weeks (up to an average live weight of 21.9 kg). The study was performed with 128 Noroc pigs [(*Norwegian Landrace×Yorkshire*)×(*Norwegian Landrace×Duroc*)] from 19 litters, at the experimental pig house of the Norwegian University of Life Sciences. There were four dietary treatments; one group was fed a control diet containing no *Ganoderma lucidium* beta glucans; one group received a diet containing 1.0 mg *Ganoderma lucidium* beta glucans/kg, one group received a diet containing 2.0 mg *Ganoderma lucidium* beta glucans/kg; and one group received a diet containing 3.0 mg *Ganoderma lucidium* beta glucans/kg. Each of the treatment groups consisted of 8 replicate pens (4 piglets in each pen).

Clinical Signs

All visible signs of ill health and any behavioral changes were recorded daily, and any deviation from normal was recorded. The following parameters were monitored:

Body weight
Feed consumption
Fecal scores
Hematology of blood samples

Observations:
No clinical problems arose from the dietary treatments. The animals showed good growth; in average for all of the pigs the daily gain (ADG) was 455 g for the overall experimental period.
No significant effects of *Ganoderma lucidum* beta glucans on weight gain, feed intake or feed conversion ratio.
No adverse effects.

Example 10: Rat Study

The beta glucan product from *Ganoderma lucidum* has been tested in rats according to the requirements to document product safety. The sole purpose of these tests was to document that the beta glucan product from *Ganoderma lucidum* is a safe product and will not cause any adverse effects on ingestion.

This was a three and six month oral toxicity study of *Ganoderma lucidum* beta glucans administered by Oral Gavage to Sprague Dawley Rats. The study was carried out at Science, Toxicology & Technology, Inc. (a division of ATOX RESEARCH), 655 Montgomery, Suite 800, San Francisco, Calif. 94111, USA.

Observations:
No toxicity was associated with *Ganoderma lucidum* beta glucans.
No adverse effects were found to occur Example 11: Mice Study The beta glucan product from *Ganoderma lucidum* has been tested in mice according to the requirements to document product safety. The sole purpose of these tests was to document that the beta glucan product from *Ganoderma lucidum* is a safe product and will not cause any adverse effects on ingestion.

Effect Recorded:
Stimulation of transcription factor NF-κB in the gut region of mice after a single oral dose of the beta glucan product from *Ganoderma lucidum*. NF-κB is an enhancer of B cell activation, which is a vital part of the immune system.

Observation:
A strong indication that the beta glucan product from *Ganoderma lucidum* is a powerful immune stimulant.

Example 12: Ex-Vivo Data

The immune stimulating characteristics of the beta glucan product from *Ganoderma lucidum* have been tested using a well known ex-vivo method developed by Professor E. Mollnes at the Ullevaal University Hospital, Oslo, Norway. Briefly, the beta glucan product from *Ganoderma lucidum* was added to human blood and the resulting immune response was measured. It was found that the beta glucan product from *Ganoderma lucidum* stimulated a series of cytokines and other signaling proteins that activate the immune system.

Observations:
Activation of IL-4, IL-6, IL8, IL-9, IL-16, IL-17, IL-2a, IL-1b, IFN-γ, TNG-α, GCSF, MCP, MIP Example 13: In-Vitro Data In-vitro tests are normally used as the first screen for potential immune stimulants. The technique is well known and used extensively throughout the world. Briefly, mouse cell lines are cultivated in selected media in which small amounts of the beta glucan product from *Ganoderma lucidum* were added.

Using the standard mouse cell line P388 it was shown that:
The beta glucan product from *Ganoderma lucidum* stimulated production of IL-1a and IL-6 and was thus found to be immune stimulating.

Example 14: Protocol for Cultivation of Basidiomycete Cells According to the Present Invention Cultivation Conditions:
Temperature: 25° C.±1° C.
pH: Medium pH
Water: Tap water
Medium:
  Glucose 30 g/l;
  Mycological peptone 10 g/l;
  Yeast extract 6 g/l
  Malt extract 6 g/l
Plate Cultivation of Basidiomycete Cells
  15 cm Petri dishes containing about 60 ml of the medium+agar at a concentration corresponding to 15 g/l. Inoculate the plates by scraping off the top layer of mycelium on a Petri dish using a sterile scalpel and spread it onto the new plate. One Petri dish will yield enough mycelium to inoculate three new plates. Cultivate the plates at 25° C. for at least three weeks prior to use. They can be kept at this temperature for a total of 7 more weeks before they should be discarded.
Shake Flask Cultivation of Basidiomycete Cells
  500 ml Ehrlenmeyer flasks containing 200 ml of medium. Scrape off the top layer of mycelium on two plates using a sterile scalpel and place in a 300 ml Ehrlenmeyer flask containing 100 ml of medium. Homogenize the resulting mixture. Inoculate the 500 ml flasks with 50 ml of the homogenised material per flask. Put on orbital shaker at 25° C. and 140 rpm and leave for 7-10 days. If required, longer fermentation periods can also be used, such as e.g. 15-30 days.
Fermenter (3 Litres) Cultivation of Basidiomycete Cells
  Place 1.7 litres of the medium in the fermenter and sterilise at 121° C. for 20 mins. Set the fermentation conditions: 25° C., 200-300 rpm and air at 0.2-0.5 vvm. Decant as much liquid as possible from two shake flasks and inoculate the fermenter with the remaining broth (this will normally amount to 300-500 ml). Add a suitable antifoam agent when required (normally throughout the run). Harvests after 6-8 days. If required, longer fermentation periods can also be used, such as e.g. 15-30 days.
Harvesting of Basidiomycete Cells
  Biomass:
  Remove the biomass from the broth using a nylon cloth with pore size 45 as a filter medium. Wash the biomass thoroughly with water and dry in a microwave oven set at defrost until dry (normal sample size will require about 15 mins). Store in a desiccator until cool and weigh.
  Fermentation Liquor:
  The concentration of bioactive agent in the fermentation liquor is determined by precipitation with abs ethanol. Sterile, distilled water is added if necessary to adjust the concentration to the desired level. The resulting liquid is autoclave and stored.
  Medical Grade:
  Pass the biomass-free fermentation liquor through a UF filter having a suitable cut-off value, such as e.g. a cut-off value of 300 kD. When 70-80% of the liquid has been removed add water to the retentate to wash the solution. Repeat until the solution has lost much (at least most of) its colour and appears clean.

Example 15: Protocol for Cultivation of *Trametes* sp.—and Polysaccharides Obtained from Such a Cultivation

*Trametes* Versicolour

A *Trametes* sp. fermentation, in the cultivation medium used in Example 12, takes about 7 days. The initial pH is 4.7, final pH is 3. The final biomass concentration is about 7 g/l and precipitated compound is about 0.3 g/l, the monosaccharide composition of which is about 1:0.15:1:4 (glucose:galactose:mannose). The fermentation liquid contains, after removal of biomass, no detectable free glucose,

Example 16: Protocol for Cultivation of *Schizophyllum* sp.—and Polysaccharides Obtained from Such a Cultivation

*Schizophyllum commune*

This fermentation, using the same medium as in example 12, takes about 3 days. pH falls from 4.7 to 3.3 and the biomass concentration at the end of the fermentation is about 8 g/l. The fermentation broth, after removal of biomass, contains no detectable free glucose. The precipitated product concentration is about 0.6 g/l. The monosaccharide composition is about 1:0.1:0.65.

Example 17: Bacteriostatic Effect

In this example it is demonstrated that the bioactive agent obtained by the method as described in example 12 (extracted from the Fermentation liquor) has a bacteriostatic effect on *E. coli* K12.

Method:

The bacteriostatic effect of the bioactive agent was determined by measuring the cell-density of *E. coli* K12 cultures grown in Antibiotic assay medium 3 with different dilutions of the bioactive agent. A culture without the bioactive agent in the medium was used as control.

Cells were grown in a 50 ml conical flask at 34° C. for 26 h. The dilutions of the bioactive agent in the growth medium were 1:10, 1:20 and 1:40. The optical density was measured robotically every 2 h at 660 nm.

Results:

The optical density significantly decreased in the cultures with a 1:10 and 1:20 dilution of the bioactive agent in the stationary phase (between 15 and 26 h). The incubation with a 1:40 dilution of the bioactive agent does not lead to a significant decrease in optical density in comparison with the control.

Conclusion:

The bioactive agent is shown to have a bacteriostatic effect on *E. coli* K12.

Example 18: Topical Beta Glucan Cream and its Efficacy in Chronic Olaque Psoriasis The beta glucan containing cream tested in this study is a cream wherein the beta glucans are Ganodex™ (produced as described in Example 1). The cream was produced as described in Example 6.

Objectives

To compare the efficacy and tolerability of a beta glucan containing cream versus the vehicle in patients with mild-to-moderate stable plaque psoriasis.

Patients and methods: This was a proof of concept controlled side to-side comparative study. Patients who were stable and tolerant to their psoriasis and not applying any medication to their affected skin were chosen. They were randomised to receive treatment with vehicle without the beta glucan cream or beta glucan containing cream, to be placed simultaneously twice daily for 12 weeks to selected left and right sided symmetrical target plaques of psoriasis either on the elbows or knees.

Clinical measurement used included photography and patient and investigator assessment of improvement at 12 weeks. Patients were assessed at zero, four, eight and 12 weeks and at point of withdrawal. Spontaneously reported and observed adverse events were noted.

Results

Eight patients out of 11 completed the study. All patients were evaluable up until the point of withdrawal or completion. Both groups showed decreases from baseline to end of treatment in global assessment score with topical beta glucan cream compared to vehicle. Improvement in plaque thickness and scaling was noted more in the beta glucan group than control. Irritation was less in the beta glucan group. Redness was improved by either cream.

Conclusion

Beta glucan containing cream is more effective than vehicle in mild to moderate psoriasis and represents a new opportunity for an over the counter product to treat psoriasis patients.

Introduction

There are few over-the-counter preparations specifically targeting psoriasis. Most are either bland emollients to encourage softening of the plaques or coal tar-based products both topical and bath preparations. Coal tar has long been regarded as the first-line treatment for chronic plaque psoriasis but compliance issues due mainly to odour, clothes staining and psychological reluctance limit its use. Topical beta glucan largely avoids these problems as both odour and texturally, it feels more agreeable when placed on the skin.

There have been no previous studies of a beta glucan containing cream used in skin conditions. Studies that have been performed using coal tar preparations show historical response rates of between 30 to 50%.

This proof of concept controlled side-to-side comparative study of target plaques compared the efficacy and tolerability of a beta glucan containing cream and a control vehicle cream for treatment of mild to moderate plaque psoriasis.

Efficacy was assessed using the accepted clinical measuring tools of disease severity—total signed score TSS which measures all three elements of erythema, induration and scaling and investigator global assessment of improvement.

Study Design

This was a proof of concept controlled side to-side comparative study of target plaques conducted in a bespoke hospital dermatology clinic and private dermatology outpatient centre, with full local ethical approval. Patients with stable plaque psoriasis of mild to moderate severity who had not been actively treated for the past three months were chosen. They had all given up treating their psoriasis with topical prescription products. All were using bland moisturizers for symptom control and to minimise scaling. After an initial washout period of seven days they were assigned a cream in accordance with a company produced computer generated randomization schedule. Symmetrical half body target psoriasis plaques affecting the elbows or knees were chosen as the signature sites. These were photographed at each and every stage follow-up appointment by DH. A baseline assessment using TSS was made. The investigator assessed the severity of erythema, induration, and scaling using five point scale ranging from 0=none to 4=severe. Because of the limited extent of the psoriasis the more commonly used PASI was felt to be an inappropriate assessment tool.

At the end of the 12 week treatment period the investigator and patients were asked to rate the overall effect of the study medication on the status of psoriasis using a 7 point global rating scale (ranging from 0=clear to 6=worse). Patients were also asked about the cosmetic feel of the creams, ease of use and smell. Would you recommend this product to others with psoriasis?

Subjects

Male and female patients aged at least 16 years with mild to moderate chronic plaque psoriasis not requiring systemic therapy, were patients attending a private hospital and private outpatient dermatology clinic or recruited by general practice centres. Excluded patients included those with pustular, palmar, plantar, erythrodermic, flexural, anal or genital psoriasis; known sensitivity to mushrooms or any of the constituents of the study medication: planned exposure to the sun during the study period, serious concomitant medical conditions: those likely to be non-compliant with the study procedures: women who were either pregnant, lactating or not using effective contraceptive measures. Treatment with systemic or ultraviolet therapy or any investigational drug in the four weeks prior to starting the study medication, or concomitant treatment with any medication thought likely to influence the course of psoriasis was prohibited.

Ethical Consent

The study was approved by the Ethics Committee of the Hospital of St John & St Elizabeth. Written informed consent was obtained from all patients prior to screening procedures and entry into the study.

Assessments

Two target psoriasis plaques of similar size, morphology and location, which were considered representative of the patient's disease, were selected for assessment in each patient by the investigator at entry to the washout period. Plaques were assessed using the Total Sign Score (TSS) (erythema, induration and scaling). At screening, and weeks 0, 4, 8 and 12 during the treatment period, the investigator assessed the severity of erythema, induration, and scaling, using 5-point scales ranging from O=none to 4=very severe.

At the end of the 12-week treatment period, both the investigators and patients were asked to rate the overall effect of the study medication on the status of the psoriasis using a 7-point global rating scale (ranging from 0=clear to 6=worse). Patients were also asked to assess the cosmetic acceptability of the two study treatments. Patients were asked to assign a score on a 5-point scale to the questions: "Was the product easy to use?", "Was there an unpleasant smell?", "Was the product greasy?", "Did the product stain your clothing?", "Did you like the product overall?", "How did the product compare with other products you have used?" Spontaneously reported and observed adverse events were noted at each visit during the 12-week treatment period.

Statistical Analysis

The primary endpoint was the percentage change from baseline (week 0) to week 12 (or last visit on study treatment) in mean TSS. Screening assessments were carried out at week −1 and no study medication was used between week −1 and week 0. Change from baseline=(Final value−Baseline value)/Baseline Value Results Of a total of 11 patients screened and randomised between August 2012 and October 2013, 3 were failed to complete the trial withdrawing for a flare of their psoriasis (2) and cosmetic intolerance (1—female). Therefore 8 patients (all male) applied the study treatments to completion.

At the time of screening, the mean duration of psoriasis was about 7 years, with psoriasis affecting about 2% of the body surface area. All the patients had previously used topical steroids, tar or calcipotriol. Most of the selected target lesions in each group were on the backs of the elbow or knees.

Efficacy

The percentage change in TSS scores from baseline (week 0) to week 12 was an average of 66%. If the patient PK is removed (withdrew) the percentage change rises to 76%.

The global rating assessment score by both patient (2.8) and physician (2.5) averaged 2.6 on the seven point scale where 0 is clear and 6 is worse. The slight discrepancy is accounted for by the withdrawal patients, two of whom CB & PK showed some clinical improvement in certain parameters despite pulling out of the study.

| Patient | Patient score | Physician score |
|---|---|---|
| B H | 2 | 2 |
| R A | 2 | 2 |
| J M | 0 | 1 |
| P I | 2 | 1 |
| J S | 0 | 0 |
| N M | 2 | 2 |
| G Y | 3 | 3 |
| S G | 3 | 3 |
| G O | 5 | 5 |
| P K | 7 | 6 |
| C B | 5 | 3 |

Average patient global rating score: 2.8

Average physician global rating score: 2.5

Combined average global rating score: 2.6

Cosmetic Acceptability

Cosmetic acceptability was high for both product and vehicle. There was little perceived difference between the two treatments. The level of cosmetic acceptability was high for the mushroom based product although the only lady in the trial felt that it was too malodorous and withdrew from the trial despite seeing a benefit in her skin. The number of patients agreeing with the each statement is shown below.

| Question | Answer | % |
|---|---|---|
| Was the product easy to use? | Moderately to very easy | 90% |
| Did the product have an unpleasant smell? | Not at all, or only slightly | 90% |
| Was the product greasy? | Moderately, quite a lot or very much | 72% |
| Did the product stain your clothing? | Not at all | 100% |
| Did you like the product overall? | Moderately, quite a lot or very much | 90% |
| How did the product compare with others you have used? | Better or much better | 72% |

Overall Average Cosmetic Acceptability: 85%

Discussion

The results of this study confirm the in-house belief that Beta Glucan containing creams derived from mushrooms may offer a new further organic safe therapeutic choice for those patients suffering from mild to moderate psoriasis thereby limiting or avoiding use of topical steroid creams.

The trial shows that the Beta Glucan cream preparation is effective in reducing the mean TSS, a composite evaluation of the extent of erythema, induration and scaling associated with psoriasis. The overall reduction from baseline of 66% in TSS is consistent with previously reported trials for a range of topical preparations in psoriasis [Mason J. Mason A R. Cork M J. Topical preparations for the treatment of psoriasis: a systematic review. Br J Dermatol (2002) 146: 351-64].

Unlike tar based products this preparation has high cosmetic acceptability with no potential for staining. It also, being a naturally derived product found in the dermis of all skin has no harmful side effects.

This trial demonstrates no obvious safety concerns associated with either trial cream or vehicle base. The inherent instability imbued within the nature of psoriasis means that the therapeutic agents which improve it—occasionally to clearance, can also irritate and cause it to flare. Patients with psoriasis will recognise that there are many reasons as to why it flares, concurrent coughs and colds, stress etc so it is not entirely surprising that two patients found themselves flaring Some patients experienced increased irritation and redness during the first month of treatment. In two patients a clear skin irritation was demonstrable and they withdrew. Those that persisted saw good improvement with abolition of itch and a decrease in redness till completion.

Drop outs were the only lady on the trial who did not like the aroma. The two other drop outs were males; one had the thickest hyperkeratotic plaques who stated increased irritation using the products. These two males noted increasing redness and irritation within three weeks of starting the trial preparations. Other patients had briefly experienced this entity but persisted and ended up getting improvement in their lesions. Unsolicited comments—"this is the best cream I have used for my psoriasis in 20 years" . . . "definitely helped" . . . "cream does something" . . . "my skin has come back" . . . "I would apply the cream forever as it is better to have no scales forever" . . . attest in an non scientific way to its efficacy.

Three patients felt that the cream enhanced more rapid clearing or improvement of their plaques in sunlight than they had experienced before. As many plants contain psoralens which are used in treating skin conditions using phototherapy, this may be an avenue of future research to pursue.

Further work needs to be undertaken to establish why beta glucan cream works in psoriasis but harnessing the potential of this novel natural and organic polysaccharide will certainly appeal to the ever increasing market of psoriasis sufferers who would like an accessible OTC product to control their condition without the attendant risks other agents bring.

| Summary |
|---|
| N = 11 |
| 10 males, 1 female |
| Average age 49 years (20 to 75 years) |
| 8 completed; 3 withdrew including female |
| Average Lesion Baseline Improvement TSS score: 66% |
| Averaged Psoriasis Global Rating Score: 2.6 (0 = clear; 6 = worse) |
| Cosmetic acceptability was good |
| Treaments were well tolerated |
| No serious adverse events |
| Worsening of psoriasis (2) |
| Application site reactions |
| Transient increased redness initially (2) |
| Minor itch (1) |
| Irritated in sea (1) |
| Withdrawal (3) |

Figure 4:
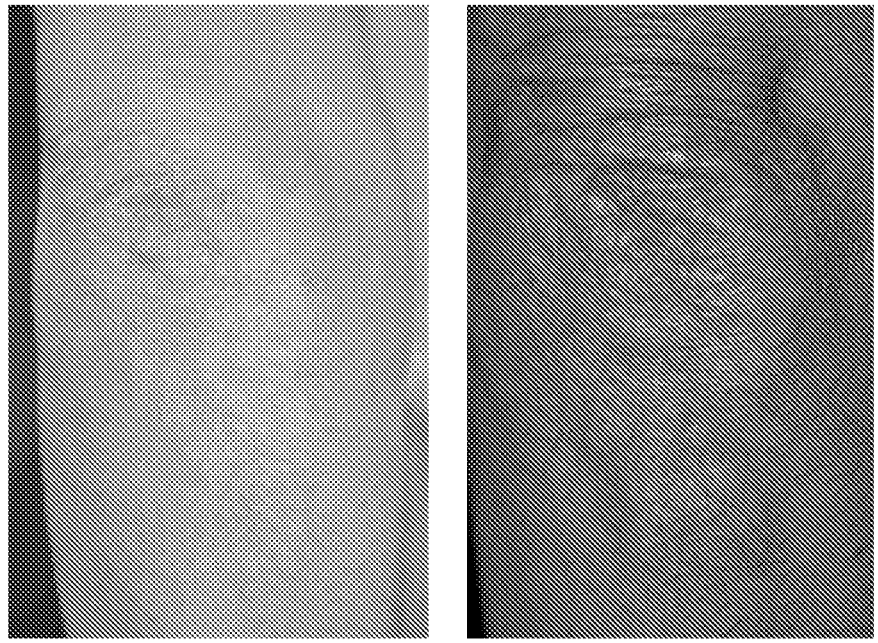
FIG. 4: Clinical photos of the pateints treated in Example 18 are shown in FIG. 4. The left hand columns are photos of the patients skin prior to treatment and the right hand columns are photos after treatment the the Ganodex™ cream as described in Example 18.
Figure 4:
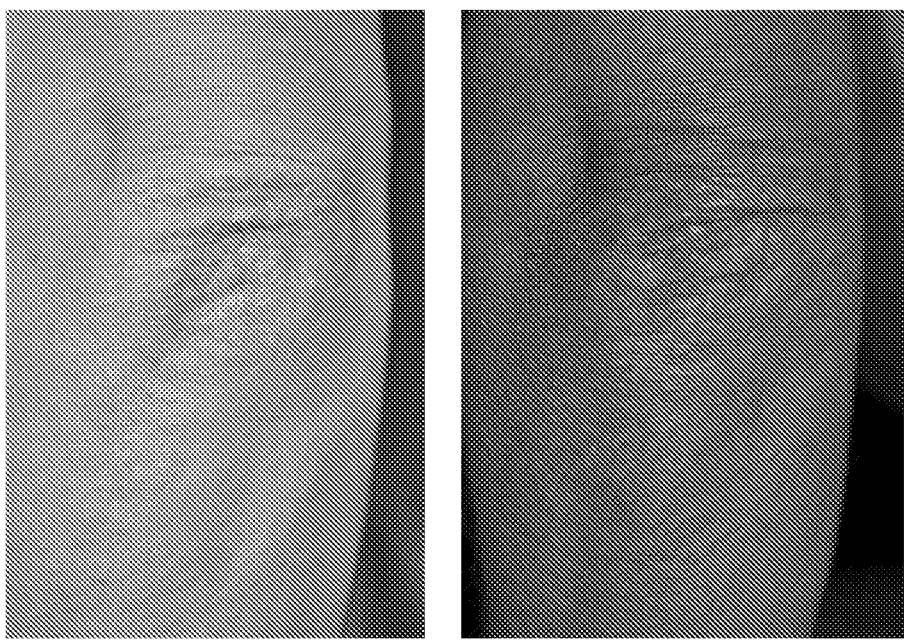
Figure 4:
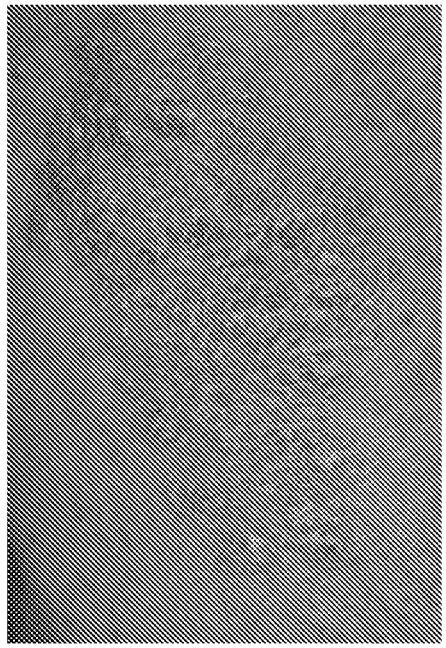
Figure 4:
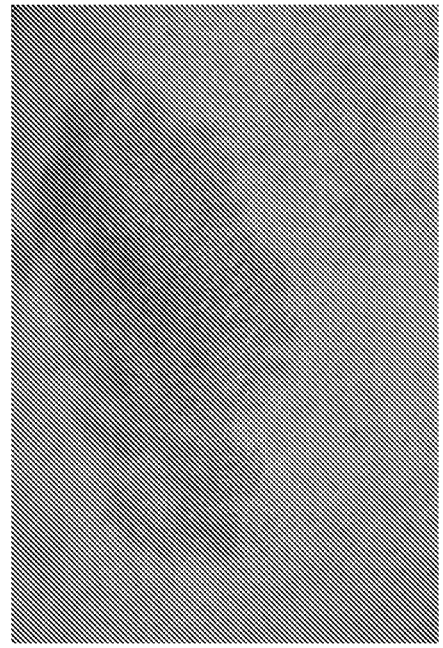
Figure 4:
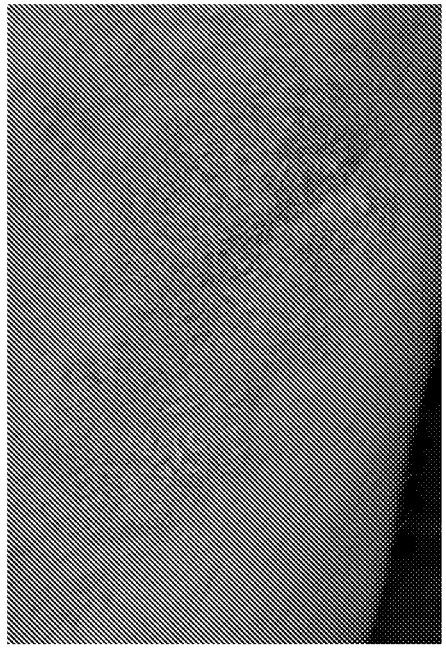
Figure 4:
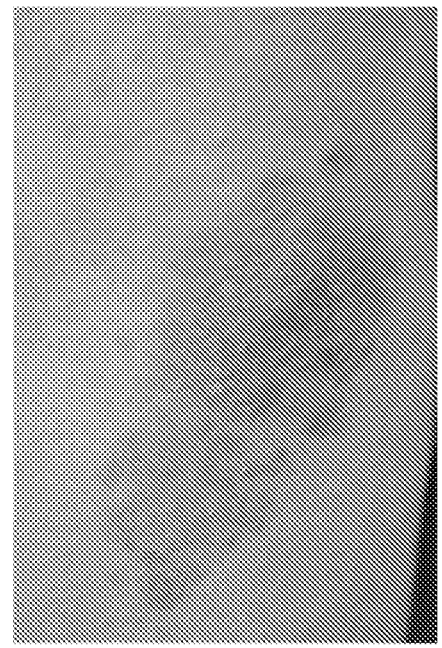
Figure 4:
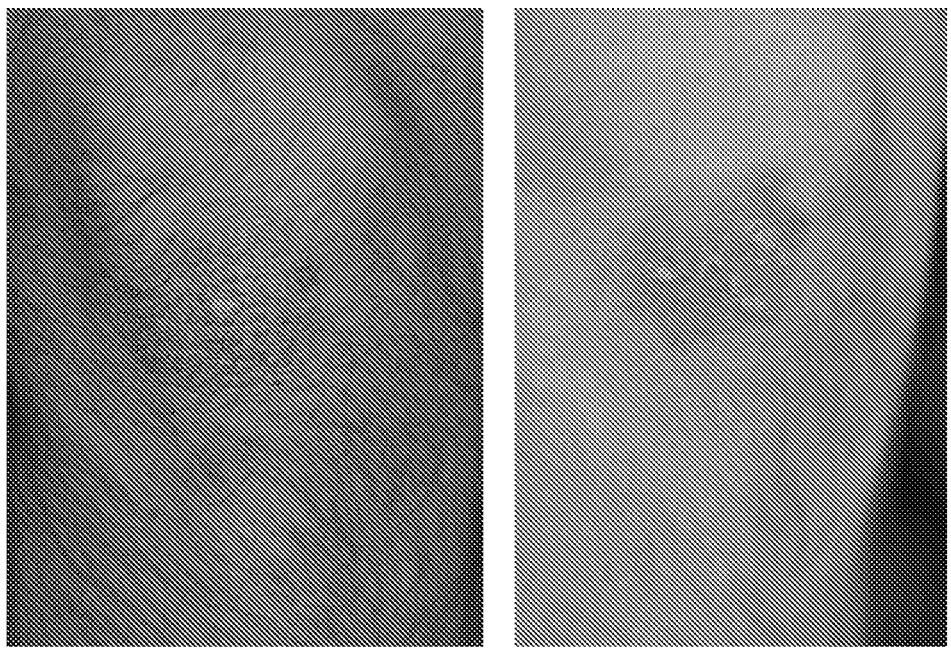
Figure 4:
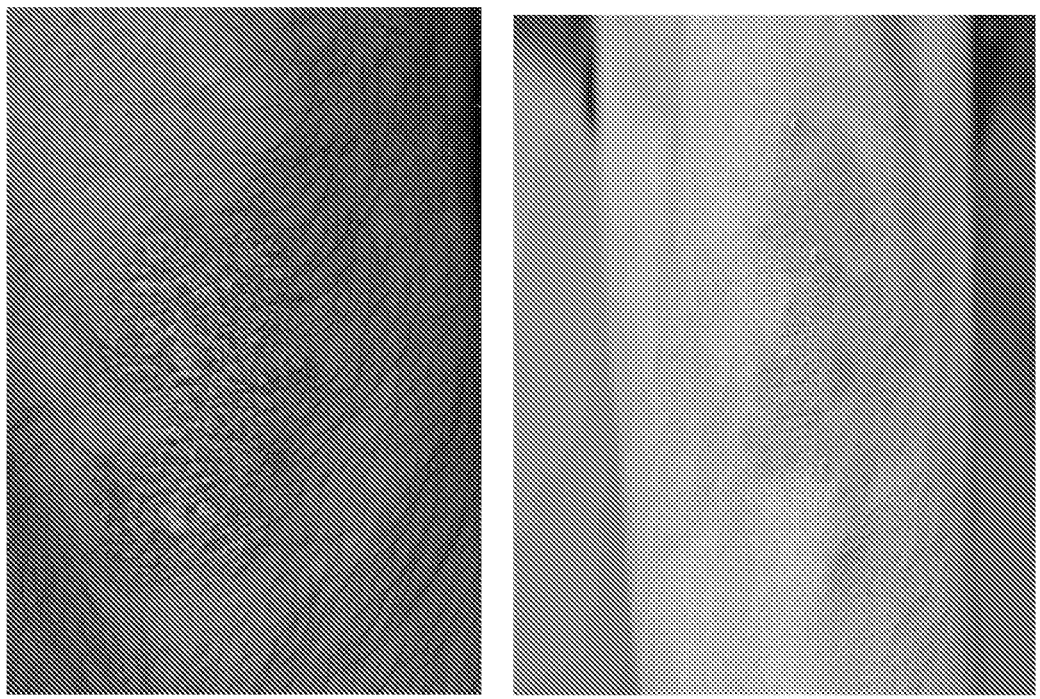
Figure 4:
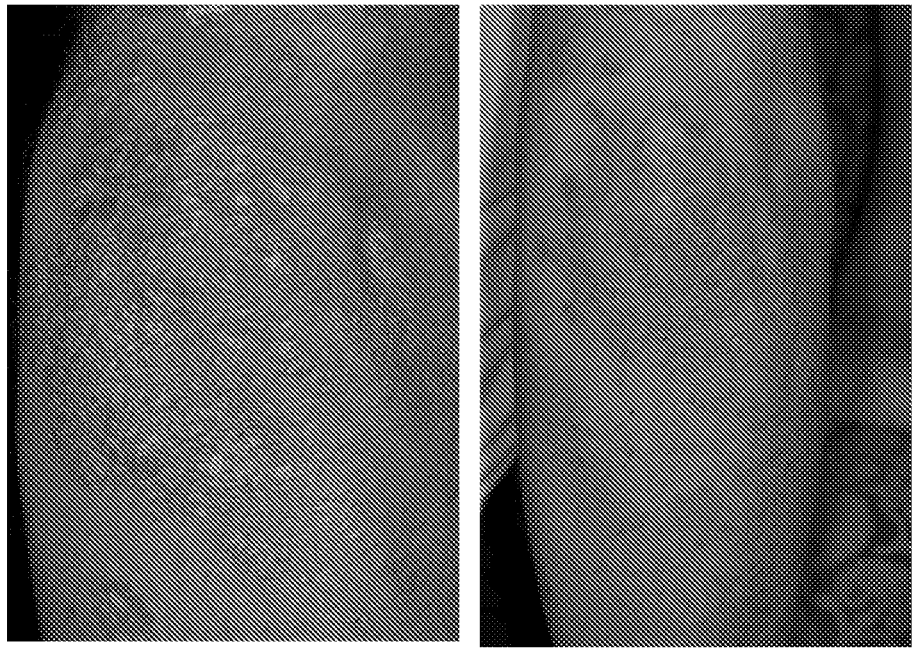
Figure 4:
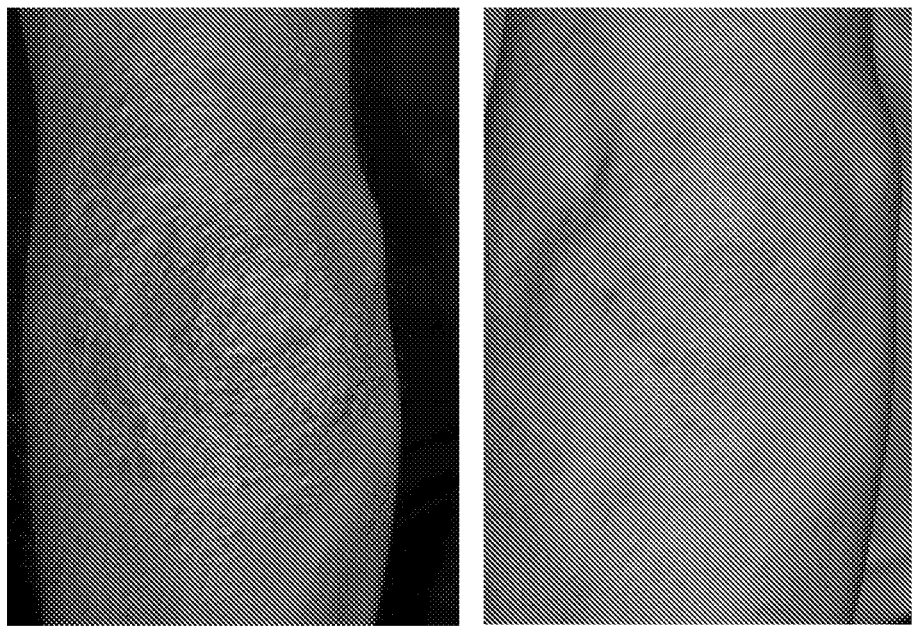
Figure 4:
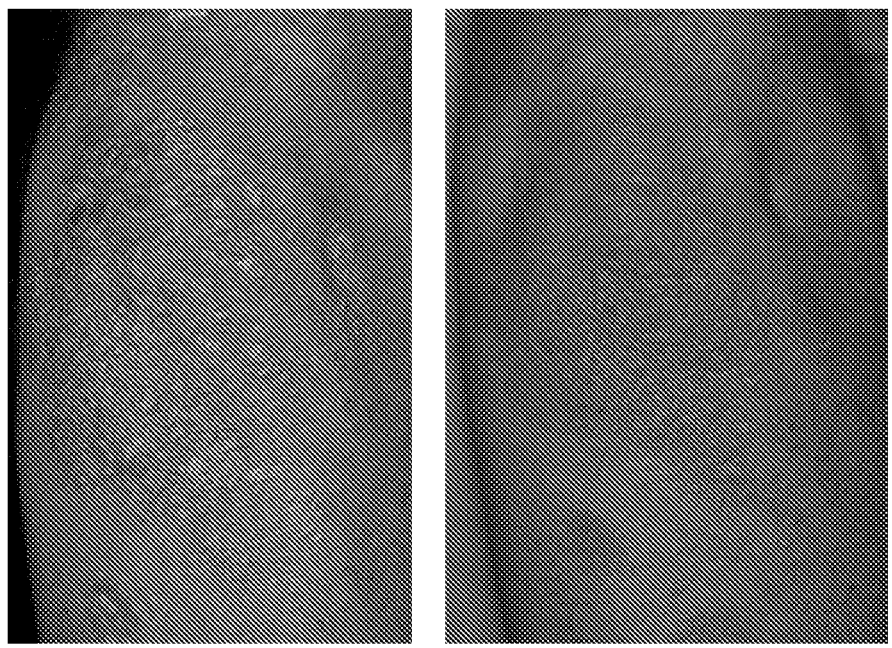
Figure 4:
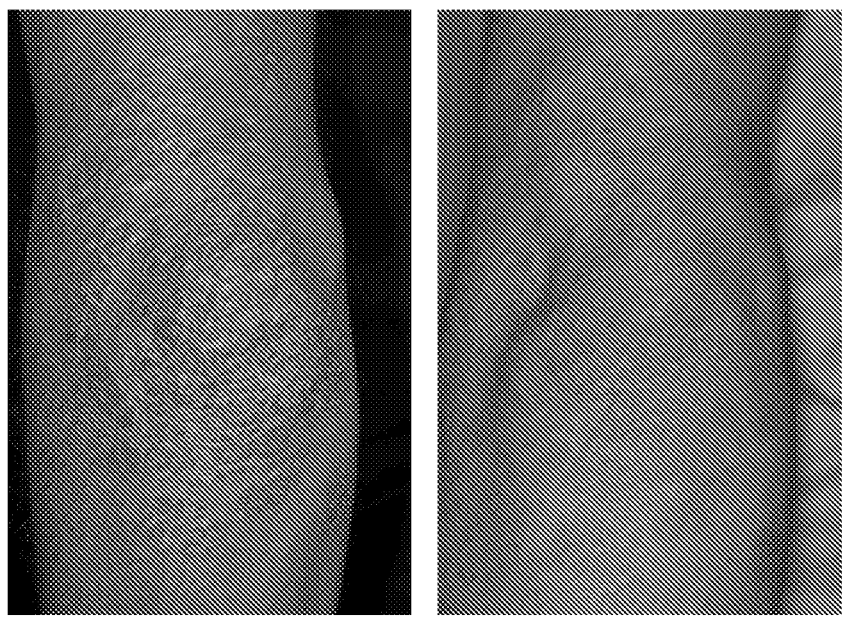
Figure 4:
Figure 4:
Figure 4:
Figure 4:
Figure 4:
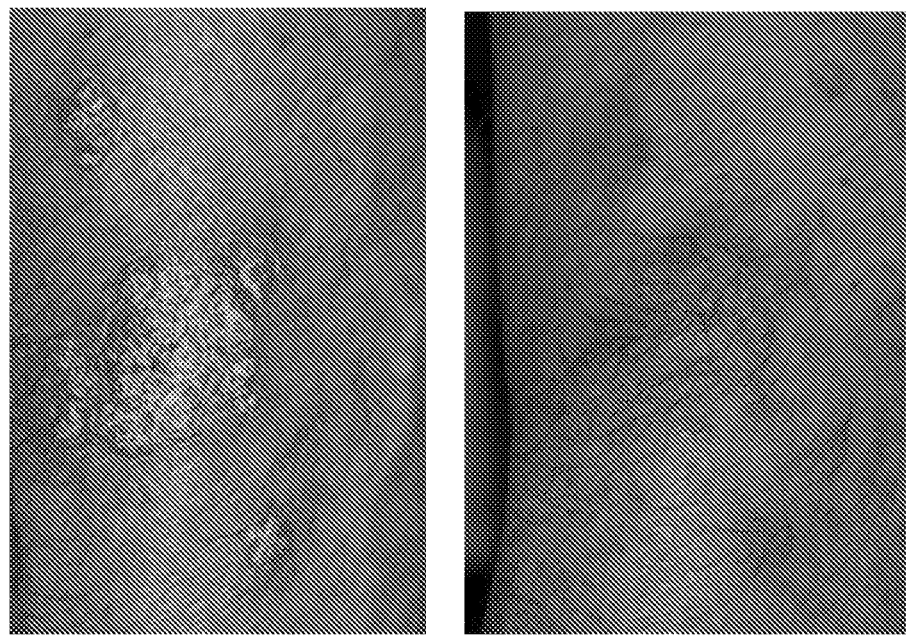
Figure 4:
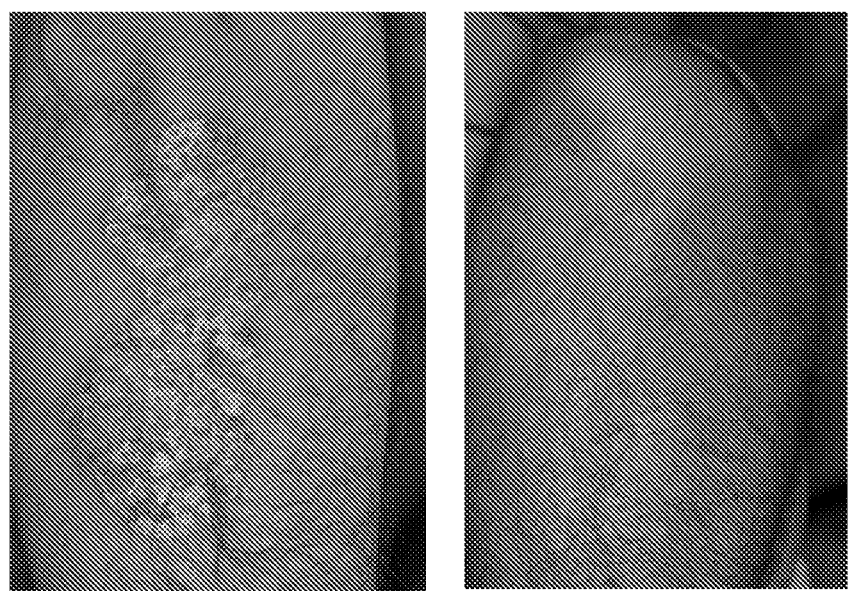
Figure 4:
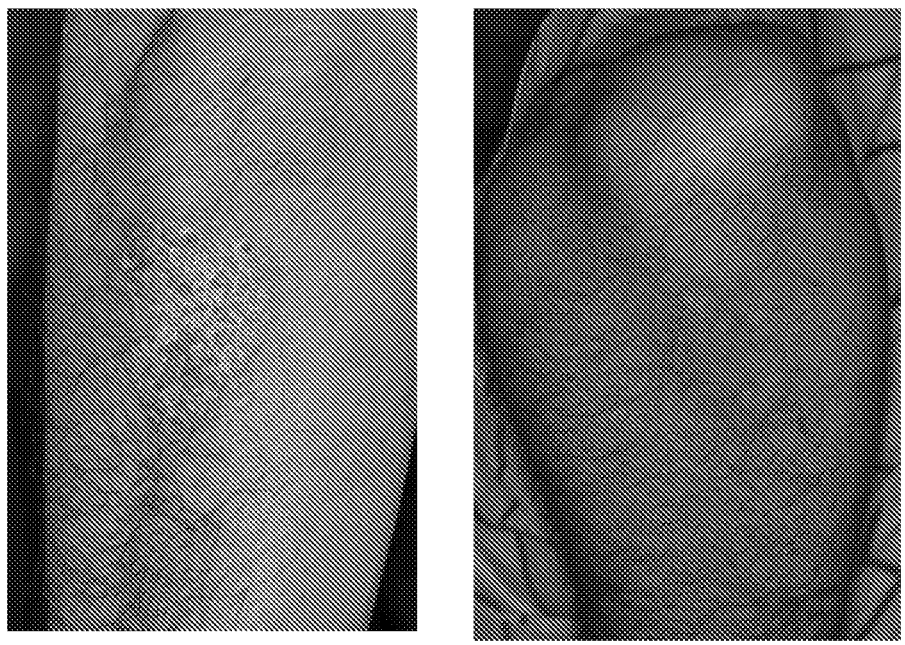
Figure 4:
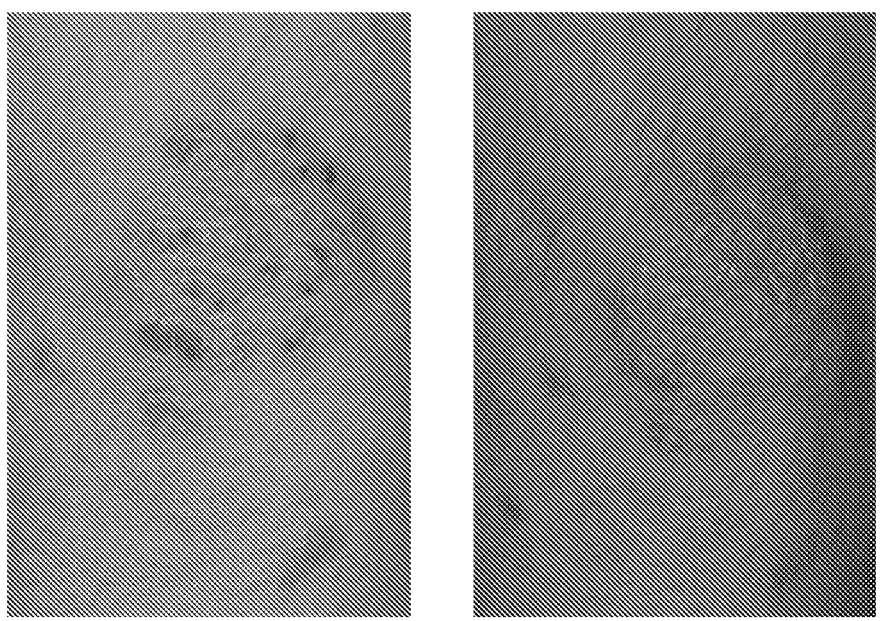
Figure 4:
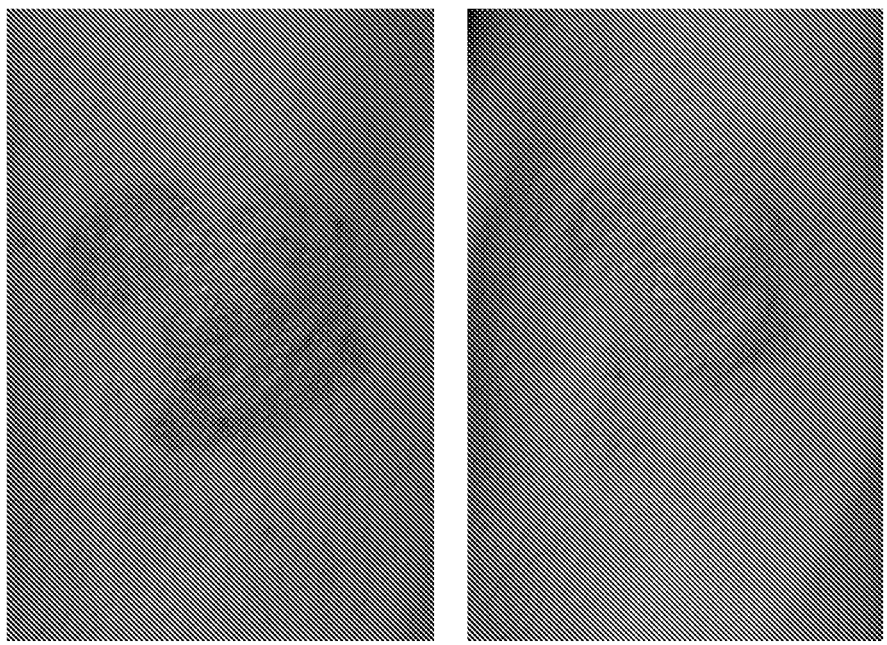
Figure 4:
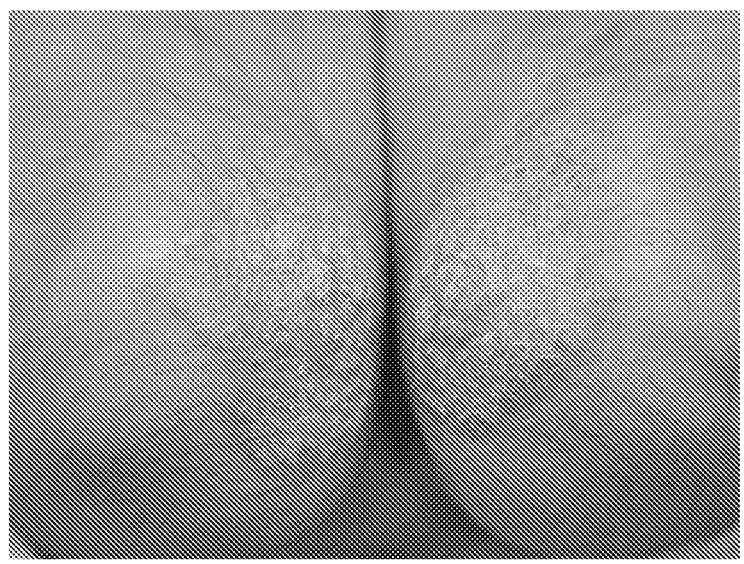
Figure 4:
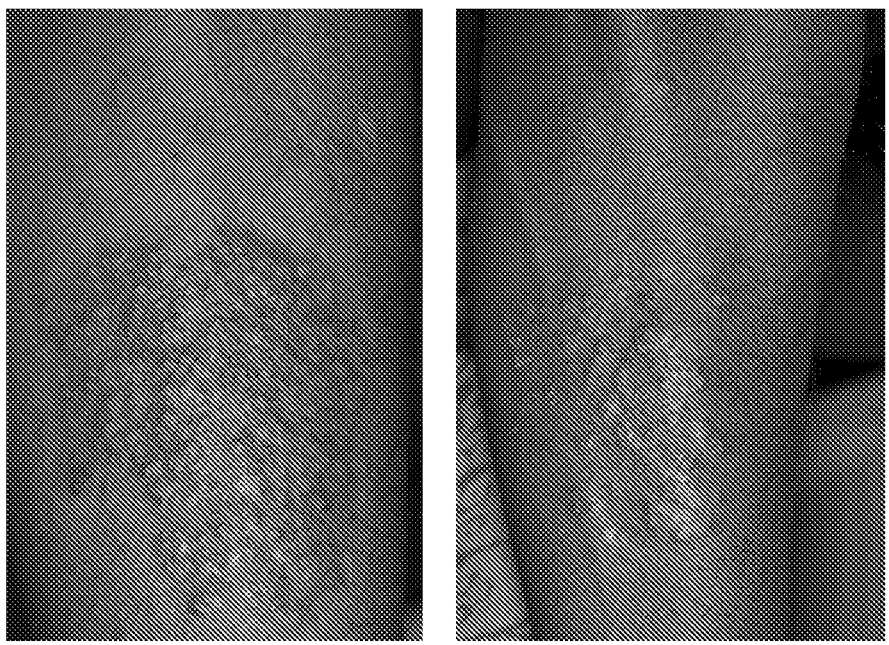
Figure 4:
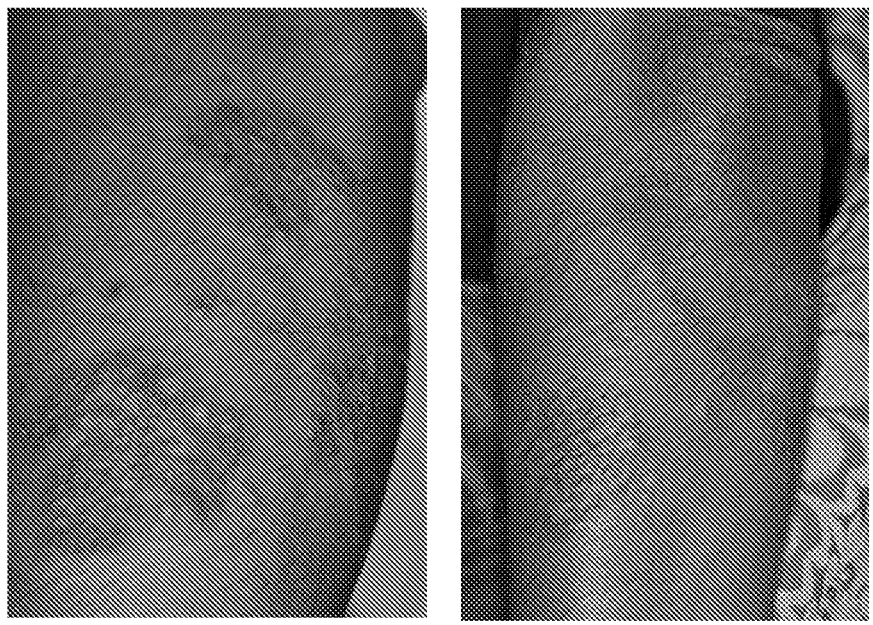
Figure 4:
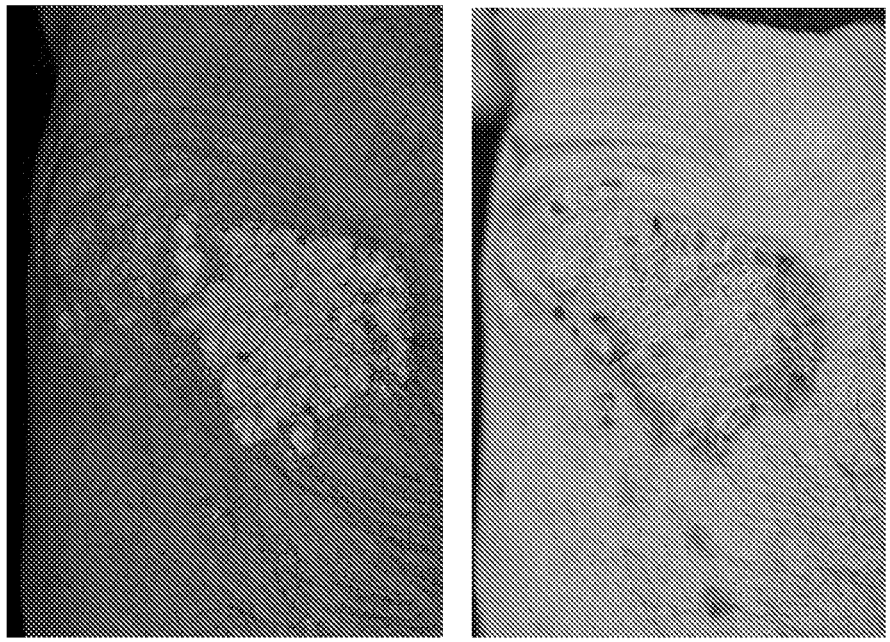
Figure 4:
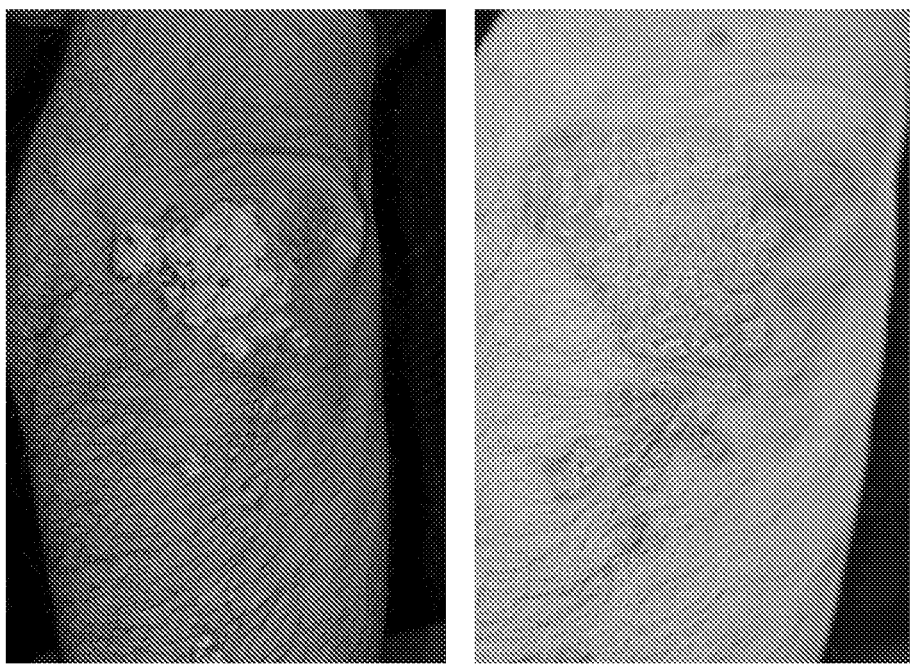
Figure 4:
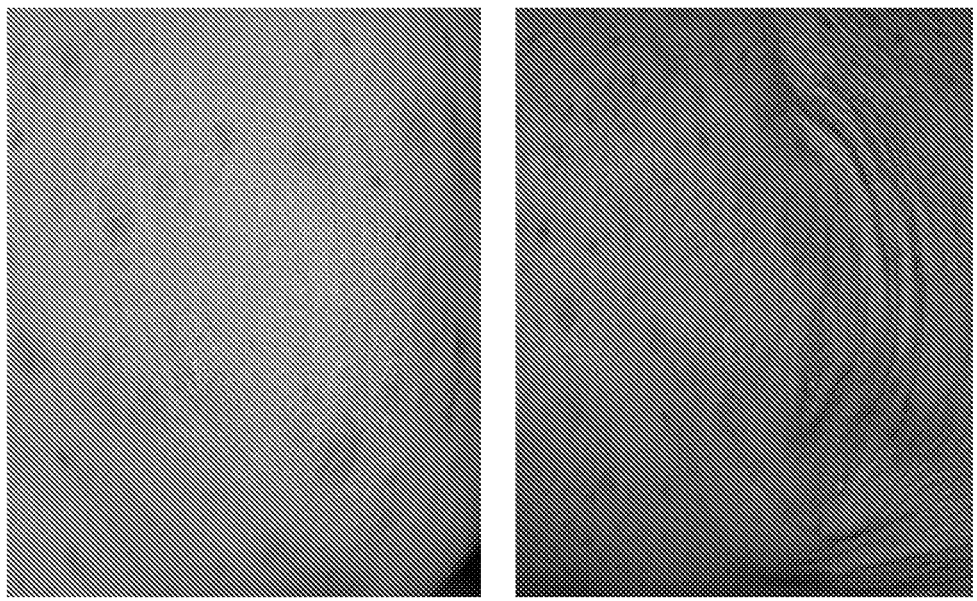
Figure 4:
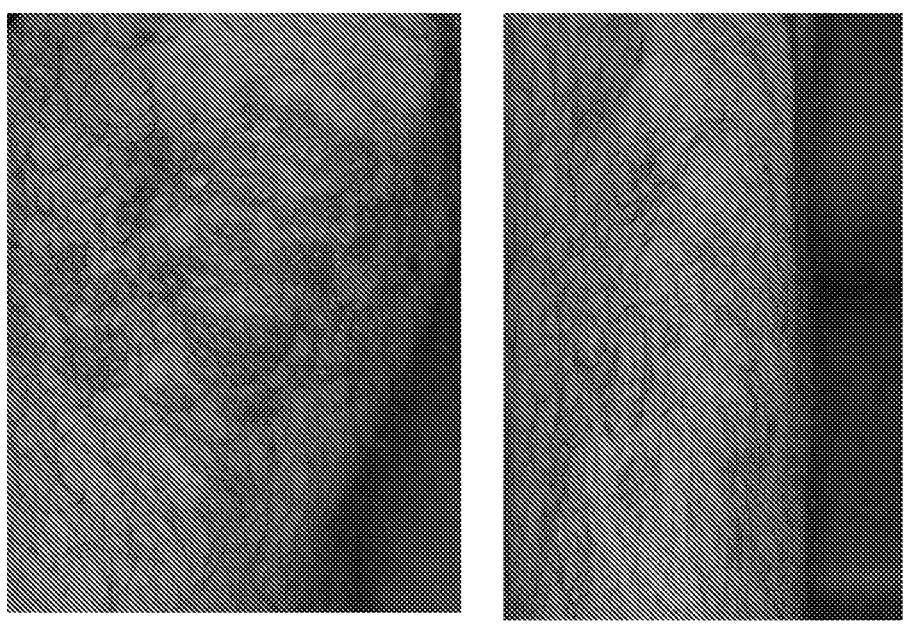
Figure 4:
Figure 4:
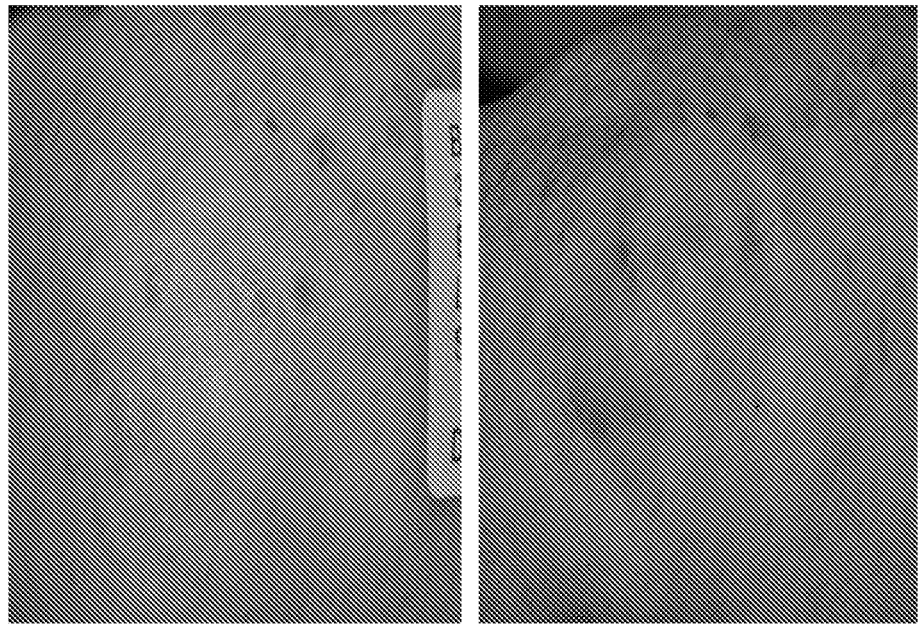

Clinical photos of the pateints are shown in FIG. 4. The left hand columns are photos of the patients skin prior to treatment and the right hand columns are photos after treatment the the Ganodex™ cream as described in Example 18.

Example 19: Effect of *Ganoderma lucidum* Product on (Ganodex™ Cream) in a Psoriasis Population The aim of this study was to evaluate possible changes reported after 2 and 4 weeks application of a cream comprising beta-glucans from *Ganoderma lucidum*, Ganodex™ in subjects suffering from psoriasis.

The Ganodex™ was produced as described in Example 1 and the cream was produced as described herein below.

Name of product: Ganodex ™ Skin Cream
Active substance: triple helix beta glucan
Title of survey: Effect of Ganodex ™ in a psoriatic population
Study centre: Domestic performance of effect-validation. Report sheets were returned to GlycaNova.

| Publication reference: | Subject Inclusion period: | Phase of development: |
|---|---|---|
| None | August and September 2013 | N/A |

Objectives:
Primary objective: The aim of this survey was to evaluate possible changes reported after 2 and 4 weeks application of a beta glucan cream, Ganodex ™, in subjects suffering from psoriasis.
Secondary objectives: Subjective opinions
Design: Open label, single group.
Number of subjects: Total 29 subjects, 20 (69%) females and 8 (28%) men. In one subject gender was missing.
Main eligibility criteria: Subjects, in all ages, with active psoriasis, were invited to participate
Investigational product, dose and mode of administration, batch number:
Ganodex ™ cream, 0.2% beta glucan, to be applied topical on the skin. Dose might vary individually.
Batch number: 15-130325
Duration of application: Two periods of 2 weeks, total 4 weeks application
Criteria for evaluation:
Primary endpoint: Reduction in symptoms, as marked on a scale with "percent reduction". Overall evaluation on a scale marking a semi-objective "percent improvement" of the skin.
Secondary endpoints. Single questions with regard to satisfaction and opinions.
Statistical methods: All results were normally distributed, parametric tests were used (t-test statistics), and Fisher's exact test if appropriate.
Summary of results:
The subject distribution, and the group score for each question, changed in a favourable direction for all questions and all reached statistical significance. As no pre-treatment values were asked, and only reduction (change) was asked for, mean pre-treatment is considered to be 0%.
The results from the primary endpoints show that there is a statistically significant and probable clinical relevant change towards a more favourable situation both for itching, scaling and redness for all questions. Over-all improvement was 44.4%. The results strongly indicate that application of the Ganodex™ cream for 4 weeks has favourable effects in a general psoriatic population. Further, duration of use may be of importance, as 4 weeks' application increased the positive results significantly compared to 2 weeks'.

The beta glucan in the cream was produced by Glycallova at Øra in Fredrikstad and made into a cream by the company Pharmatech. The cream was distributed to the subjects by post.

Questionnaires were distributed to the participants after a list received from The Norwegian Psoriasis and Eczema Association (PEF), which had invited members to participate. Questionnaires were returned to Glycanova, Fredrikstad.

An independent company, MedConsult, was responsible for processing the data, tabulation, statistics and evaluation of the results. The results are presented in this survey report, prepared by MedConsult.

Ganodex™ is a moisturizing cream for people suffering from psoriasis, eczema and other skin complaints. Daily application makes the skin smoother and softer, with increased elasticity. Those with problem skin who apply Ganodex 2-3 times daily have reported a vast, speedy improvement in their skin.

After interim results from a clinical study on-going in England, Dr. David Harris, FRCP, London Clinic of Dermatology, reported: "Glycallova has changed the premises for psoriasis treatment. The Ganodex™ cream represents a new agent with no adverse effects. This is revolutionary for psoriasis sufferers that previously had to rely on cortisone, with its well documented adverse effects."

This survey was undertaken to evaluate if possible semi-objective changes would be reported after 4 weeks' application of Ganodex™ cream in subjects with active psoriasis.

Survey Objectives

The aim of this survey was to evaluate possible changes in psoriatic skin, reported after 4 weeks of topical application of a beta glucan cream, in subjects invited to participate in the survey.

Survey Procedures

Subjects who, after invitation, volunteered to participate in the survey, were asked to fill in a one page form, estimating subjective opinion on percent changes in skin itching, scaling and skin redness after 2 and 4 weeks of treatment. Further they were asked to give an estimate of percent global improvement. Also general opinions were asked for.

Selection of Survey Population: Subjects, all ages and both genders, were invited to participate.

Efficacy Assessments: Efficacy assessments were selected on the background of the planned primary objectives.

Statistical Considerations: No sample size estimation was done, but a number of 50 subjects was chosen.

Eligibility Criteria

Inclusion Criteria: Subjects of both genders and all ages presenting an active psoriasis could be included.

Exclusion Criteria: None.

Identity of the Product Ingredients: Coconut fat, paraffin, stearic acid, honey, glycerol, cetyl alcohol, beta glucan, sorbate, benzoate. Tube containing 100 ml of a 0.2% cream.

Batch number: 15-130325

Dose of the Product

Ganodex should be applied to problem skin at least twice daily and always after showering or bathing. Avoid contact with eyes. Cream can be used as long as required. Total dose: Ad libitum.

Administration of the Product

The cream was applied to the deceased skin twice daily or more.

Handling of the Product

The product was manufactured, packed and released by Glycallova and Pharmatech. The cream was stored at room temperature and sent to the subjects by post.

Efficacy and Safety Assessments

Overview of Endpoints

The primary endpoint was the determination of any changes in distribution of subjects in percent score groups. Also the mean group score was computed. As there were no pretreatment scores, it is assumed that no mean change (equals 0) were present.

Primary Endpoint:

The primary endpoint was changes in percent score, for the 3 symptoms, itching, scaling and skin redness.

| Reduction in itching | Reduction in scaling | Reduction in skin redness | improvement |
|---|---|---|---|

The table includes the 4 outcome groups.

Secondary Endpoint:

Single questions with regard to satisfaction and opinions.

Safety Assessments

Adverse Events

An adverse event is any unfavourable, unintended event (symptom) reported by a subject or observed during the survey period and which does not necessarily have a causal relationship with the product. An adverse event (AE) can therefore be any unfavourable and unintended sign, symptom, or disease temporally associated with the use of the cream, whether or not related to the cream.

Data Management

MedConsult was responsible for data processing and control of data quality.

Statistical Evaluation MedConsult performed the statistical analyses. All analyses and tabulations were performed using Excel for Windows Version 2003 and Minitab release 14. Appropriate descriptive statistics were presented for each variable. Statistical tests were performed using 5% as the nominal level of significance and interval estimates were constructed using 95% as the level of confidence. All tests were two-sided.

Statistical Methods

Differences were tested for normality (Kolgomorov-Smirnov). As the observed differences in general were normally distributed, parametric tests as one-sample and paired T-test were used. Missing data were substituted with 0 (no effect). Fischer's exact test was used were appropriate.

Analysis of Efficacy Endpoints

Disposition of Subjects:

29 (58%) subjects completed the survey.

Demographic and Other Baseline Characteristics

The table herein below presents age and gender distribution

| | Variable | Value |
|---|---|---|
| Age (years) | Mean ± SD | 41.9 ± 19.29 |
| | Range | 4-68 |
| Gender | Female n (%) | 20 (69.0) |
| | Male n (%) | 8 (27.6) |
| | Missing n (%) | 1 (3.4) |

Results
Exposure to Direct Sun During the Test Period.
The table herein below presents the daily exposure to direct sun.

| Duration of direct sunlight exposure per day | |
|---|---|
| <1 hour | 69.0% |
| <5 hours | 13.8% |
| >5 hours | 6.9% |
| missing | 10.3% |

Daily Administrations of the Cream
The table herein below presents the distribution of number of daily cream application (percent of total).

| Number of applications pr day given as percent of total | |
|---|---|
| 1 | 17.2% |
| 2 | 58.6% |
| 3 | 6.9% |
| 4 | 10.3% |
| >4 | 3.4% |
| Missing | 3.4% |

Amount of Cream Per Application
Due to the open question without a measure (gram, ml or other), the interpretation of the results are not meaningful.
Results after 2 Weeks Treatment
Itching
The table herein below presents the distribution of subjects with percent reduction of itching after 2 weeks of cream application.

| Reduction of itching | Number of subjects |
|---|---|
| 0% | 6 |
| 20% | 6 |
| 40% | 8 |
| 60% | 1 |
| 80% | 5 |
| 100% | 1 |
| Missing | 2 |

Figure 5:
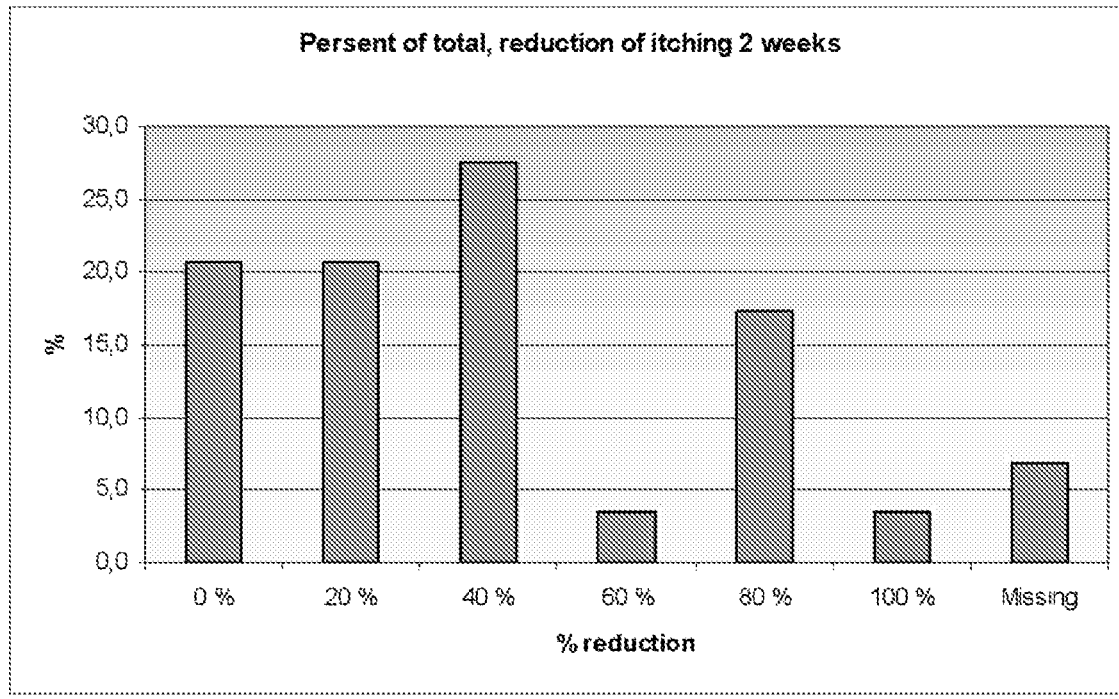
FIG. 5: Percent distribution of percent reduction of itching after 2 weeks of treatment.

0%, may indicate no effect, but may also reflect the lack of symptom at start of treatment.
52% of subjects experienced a reduction of more than 20%. The percent distribution of subjects is given in FIG. 5.
Scaling
The table herein below presents the distribution of subjects with percent reduction of scaling after 2 weeks of cream application

| Reduction of scaling at 2 weeks | Number |
|---|---|
| 0% | 6 |
| 20% | 8 |
| 40% | 7 |
| 60% | 3 |
| 80% | 3 |
| 100% | 0 |
| Missing | 2 |

Figure 6:
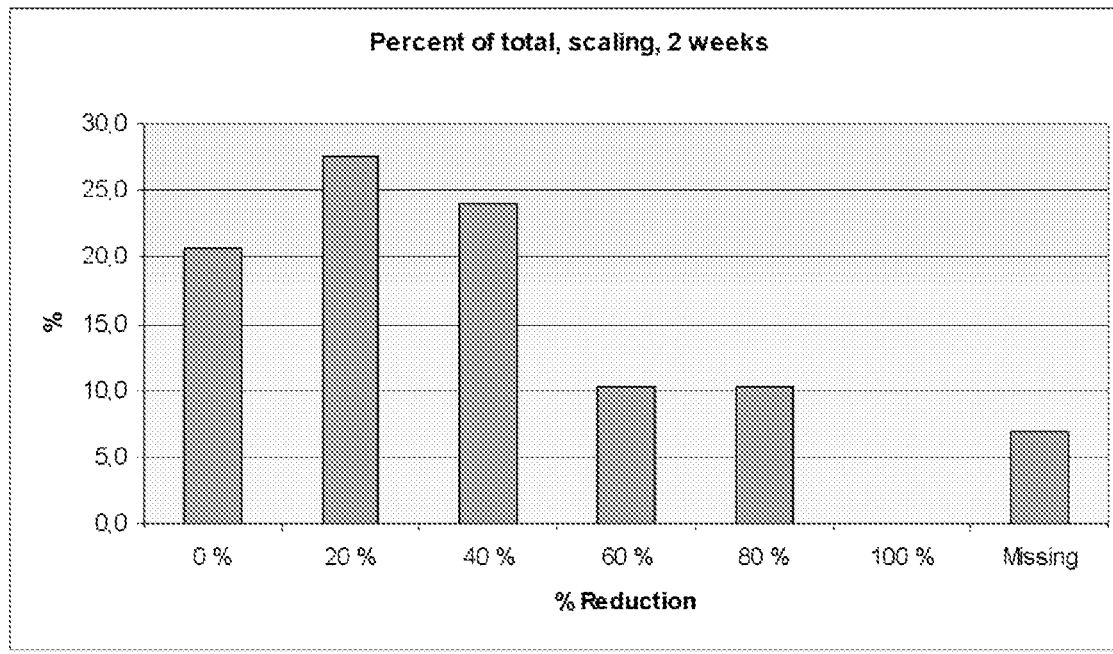
FIG. 6: Percent distribution of percent reduction of scaling after 2 weeks of treatment

0%, may indicate no effects, but may also reflect the lack of symptom at start of treatment.
45% of subjects experienced a reduction in scaling of more than 20%. The percent distribution of subjects is given in FIG. 6.

Skin Redness
The table herein below presents the distribution of subjects with percent reduction of skin redness after 2 weeks of cream application.

| Reduction | Number |
|---|---|
| 0% | 10 |
| 20% | 7 |
| 40% | 8 |
| 60% | 1 |
| 80% | 2 |
| 100% | 0 |
| Missing | 1 |

Figure 7:
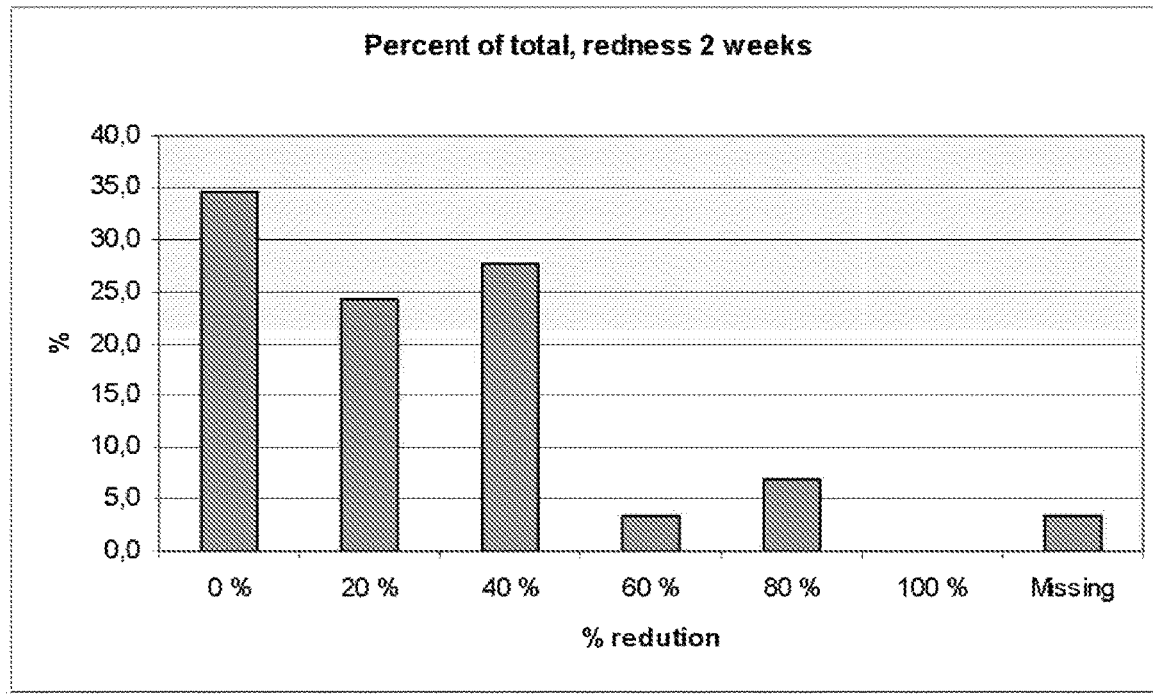
FIG. 7: Percent distribution of percent reduction of redness after 2 weeks of treatment.

0%, may indicate no effects, but may also reflect the lack of symptom at start of treatment.
38% of subjects experienced a reduction in skin redness of more than 20%. The percent distribution of subjects is given in FIG. 7.
Mean Reduction.
The mean percent reduction from pre-treatment after 2 weeks treatment is given in the table herein below.
Mean Percent Reduction from Pre-Treatment

| Variable 2 weeks | Mean | SD | SEM | p-value |
|---|---|---|---|---|
| Itching | 34.48 | 30.66 | 5.69 | 0.000 |
| Scaling | 29.65 | 25.97 | 4.82 | 0.000 |
| Redness | 23.45 | 23.95 | 4.45 | 0.000 |

Itching was reduced by 34% which is statistically significant ($p<0.000$), (assuming a zero mean reduction pre-treatment)
Scaling has a mean reduction of almost 30% from pre-treatment ($p<0.000$) but redness is only reduced by 23% ($p<0.000$). This might indicate that not all presented with redness at start of the survey, or it takes more than 2 weeks treatment to observe any reduction.
Reduction after 4 Weeks of Treatment
Itching
The table herein below presents the distribution of subjects with percent reduction of itching after 4 weeks of cream application.

| Reduction | Number |
|---|---|
| 0% | 4 |
| 20% | 6 |
| 40% | 6 |
| 60% | 1 |
| 80% | 5 |
| 100% | 4 |
| Missing | 3 |

Figure 8:
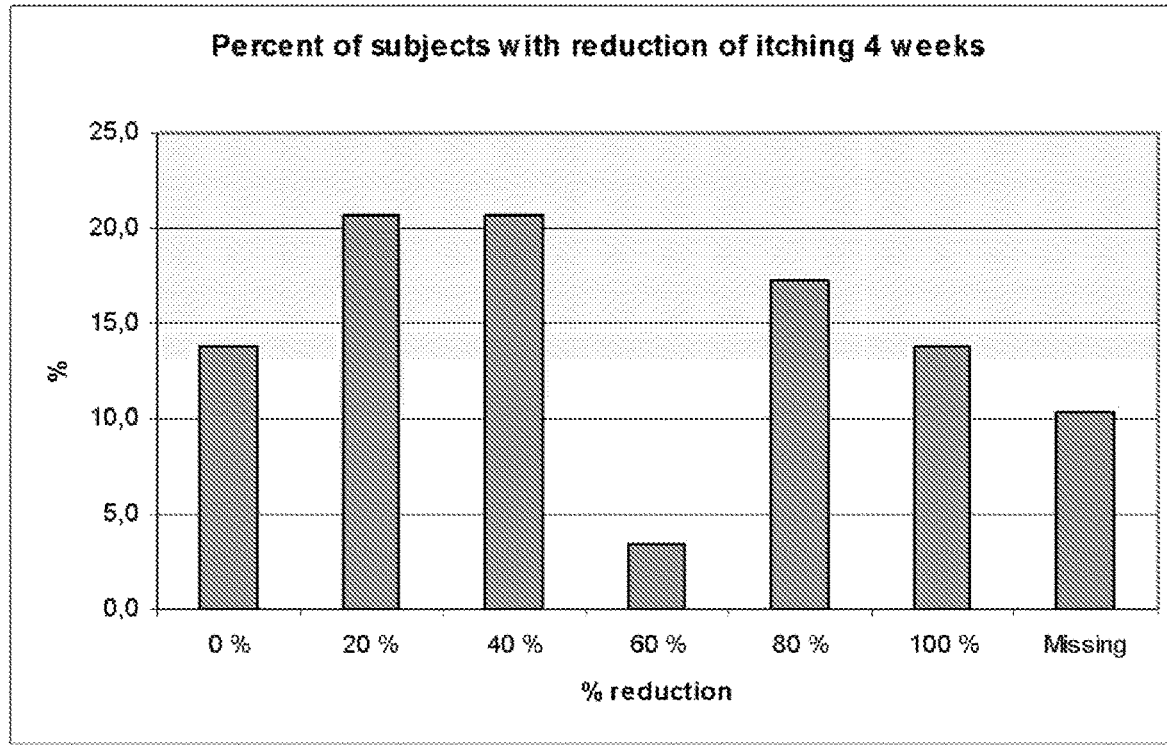
FIG. 8: Percent distribution of percent itching after 4 weeks of treatment.

0%, may indicate no effects, but may also reflect the lack of symptom at start of treatment.
55.2% of subjects experienced a reduction in itching of more than 20%. The percent distribution of subjects is given in FIG. 8.
Scaling
The table herein below presents the distribution of subjects with percent reduction of scaling after 4 weeks of cream application.

| Reduction | number |
|---|---|
| 0% | 4 |
| 20% | 5 |
| 40% | 6 |
| 60% | 4 |
| 80% | 4 |
| 100% | 3 |
| Missing | 3 |

0%, may indicate no effects, but may also reflect the lack of symptom at start of treatment.

Figure 9:
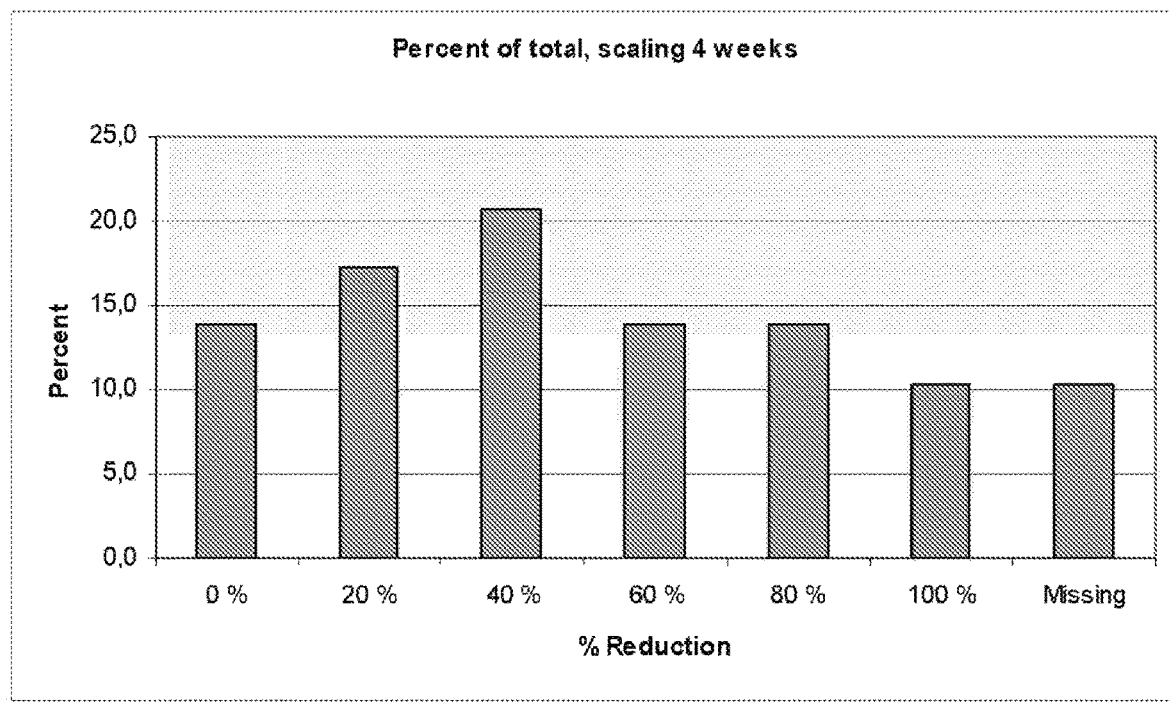
FIG. 9: Percent distribution of percent scaling after 4 weeks of treatment.

58.6% of subjects experienced a reduction in scaling of more than 20%. The percent distribution of subjects is given in FIG. 9.

The table herein below presents the distribution of subjects with percent reduction of redness after 4 weeks of treatment.

| Reduction | Number |
|---|---|
| 0% | 6 |
| 20% | 4 |
| 40% | 8 |
| 60% | 3 |
| 80% | 4 |
| 100% | 2 |
| Missing | 2 |

0%, may indicate no effects, but may also reflect the lack of symptom at start of treatment.

Figure 10:
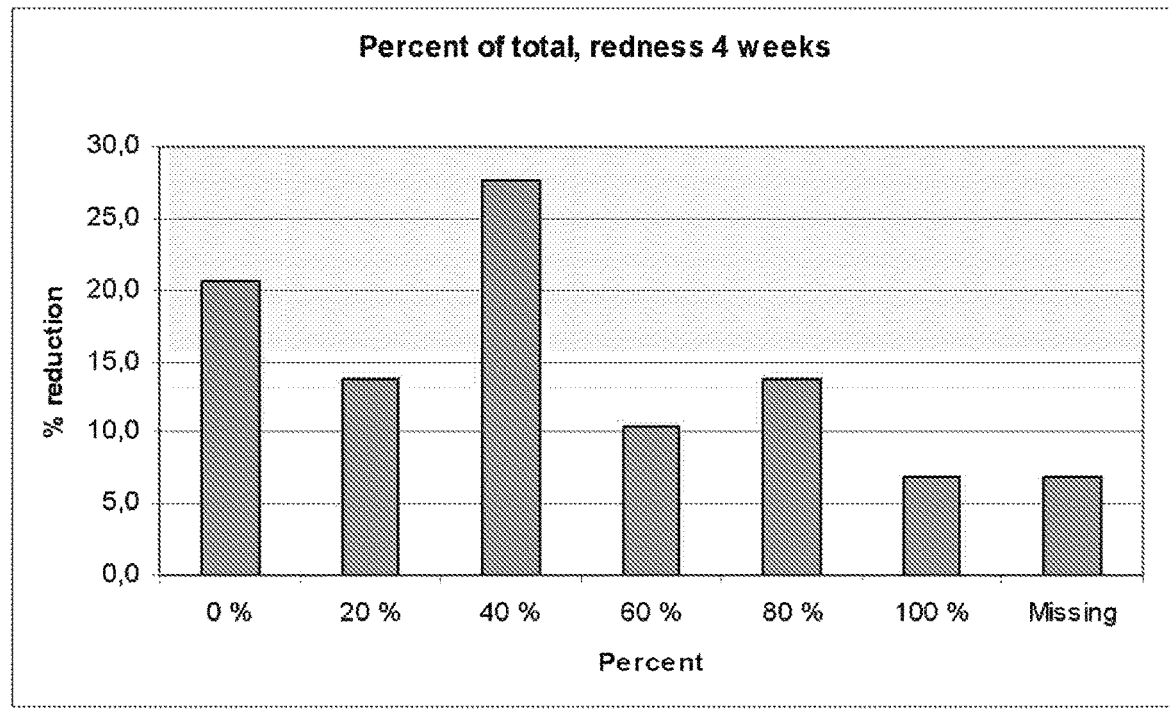
FIG. 10: Percent distribution of percent redness after 4 weeks of treatment.

Skin Redness 58.6% of subjects experienced a reduction in redness of more than 20%. The percent distribution of subjects is given in FIG. 10.

Mean Reduction at 4 Weeks

The mean percent reduction from pre-treatment after 4 weeks treatment is given in the table herein below.

Mean Percent Reduction from Pre-Treatment

| 4 weeks | Mean | ±SD | ±SEM | p-value |
|---|---|---|---|---|
| Itching | 42.07 | 35.99 | 6.68 | 0.000 |
| Scaling | 41.38 | 33.77 | 6.27 | 0.000 |
| Redness | 37.93 | 32.22 | 5.98 | 0.000 |

After 4 weeks treatment, Itching was reduced by 42%, which is statistically significant (p<0.000), Scaling has a mean reduction of 41% from pre-treatment (p<0.000).

Redness is still the lowest, but stepping up to 38% (p<0.000) indicates that one might need a longer time to fully eradicate the skin symptom redness. This might also indicate that not all presented with redness at start of the survey.

Figure 11:
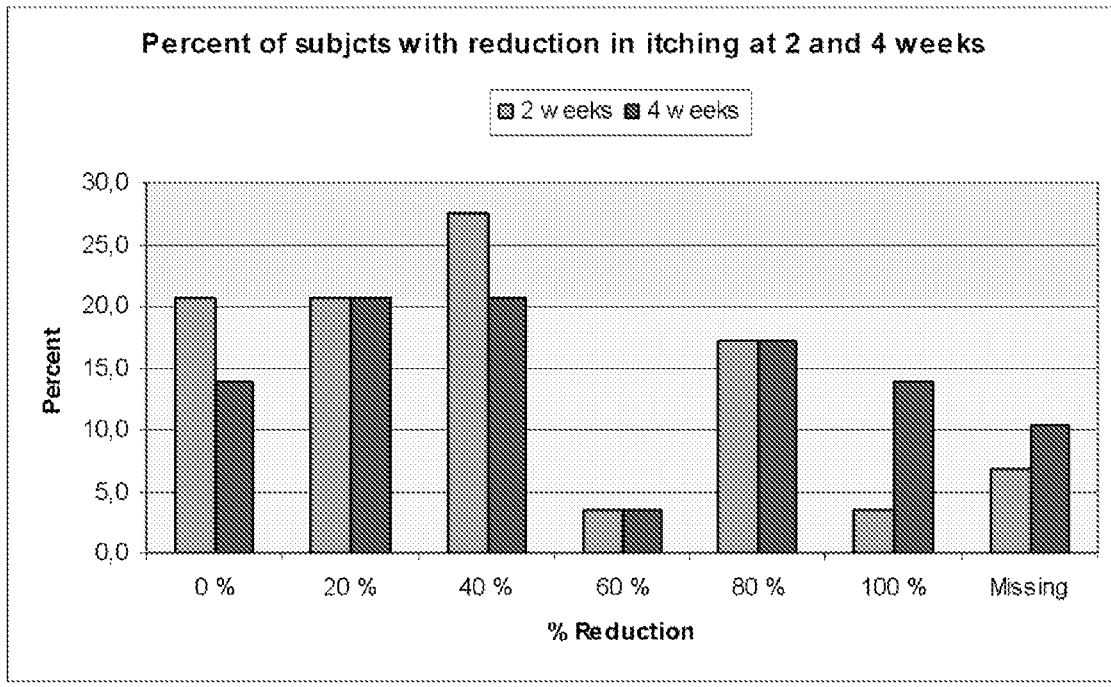
FIG. 11: Comparison of itching after 2 weeks and 4 weeks treatment.
Figure 12:
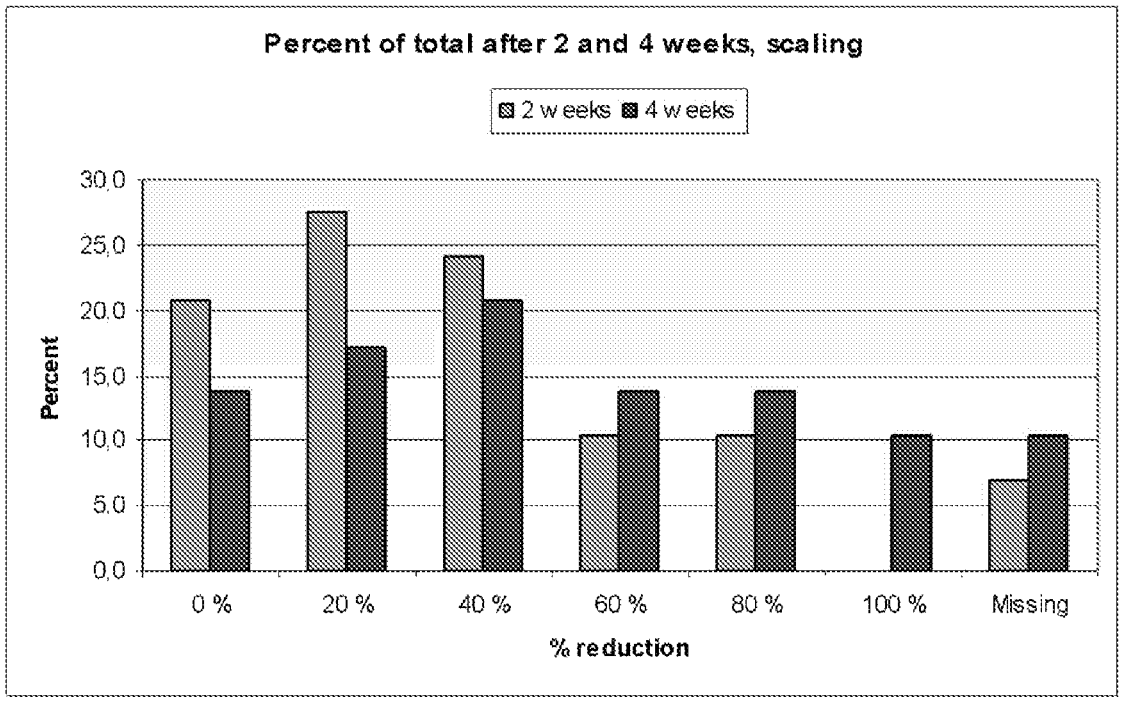
FIG. 12: Comparison of scaling after 2 weeks and 4 weeks treatment.
Figure 13:
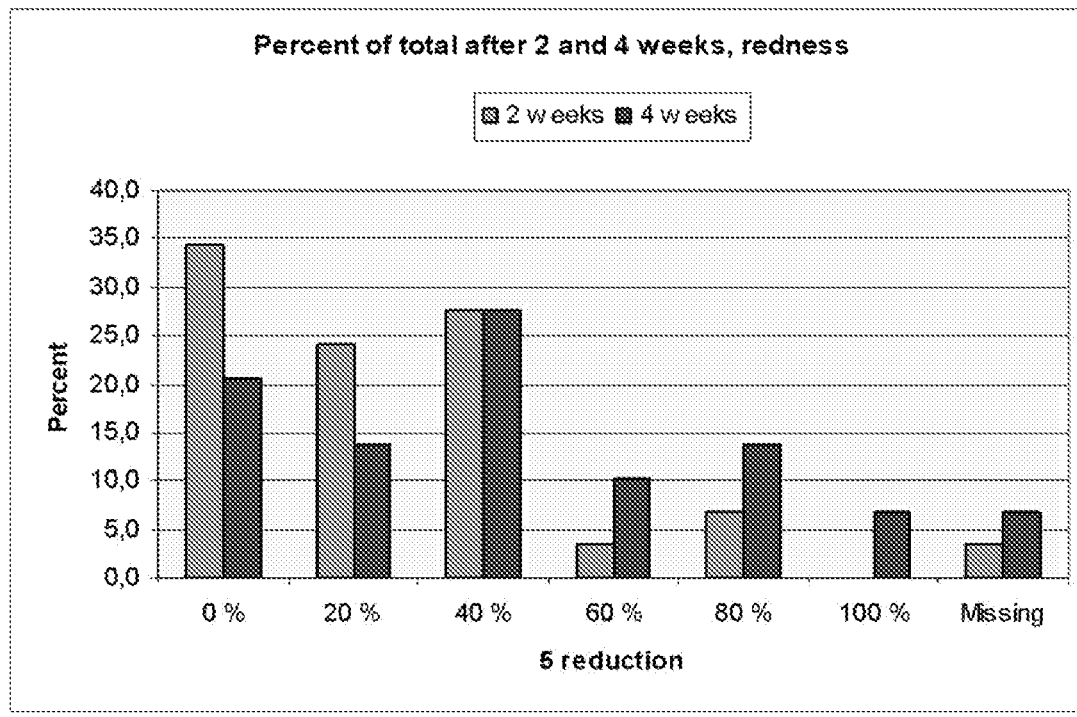
FIG. 13: Comparison of redness after 2 weeks and 4 weeks treatment.

The following FIGS. 11, 12 and 13, sum up the results. The change in distribution of subjects from 2 to 4 weeks is not statistically significant, but an indication that 4 weeks treatment might give an additional effect, is present.

Figure 14:
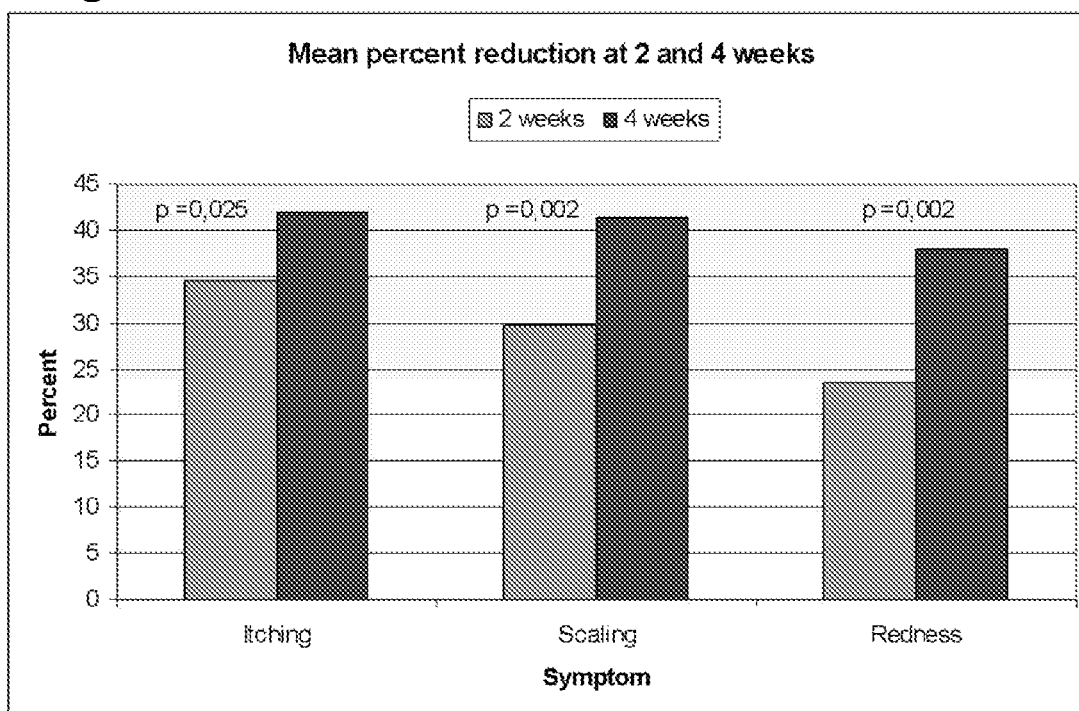
FIG. 14: Distribution of mean percent reduction the 2 and 4 weeks treatments.

The mean difference in mean percent reduction after 2 and 4 weeks is visualised in FIG. 14. The mean difference in Itching was statistically (p=0.025) in favour of 4 weeks' treatment. Both differences in scaling and skin redness were significantly better after 4 weeks compared with 2 weeks. p-values are given in FIG. 14.

Global Opinion

Figure 15:
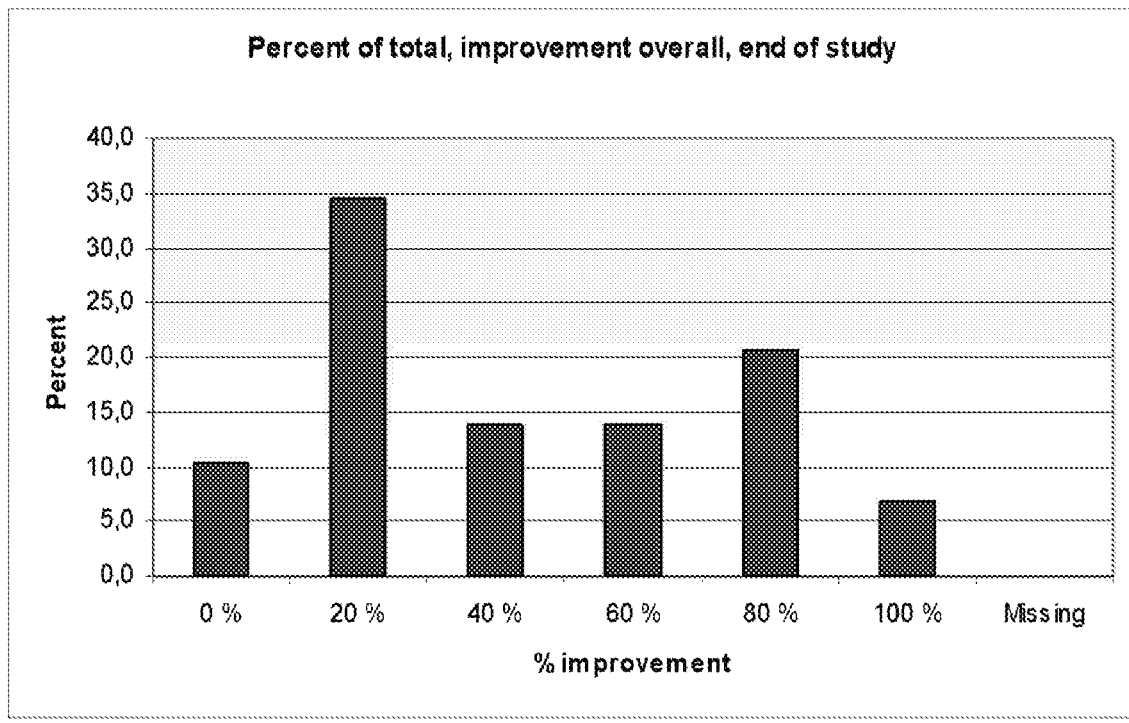
FIG. 15: Distribution of percent improvement after 4 weeks of treatment.

The participants were asked to mark their opinion on improvement, and the results are presented in FIG. 15.

The mean Global improvement was 44.4% (±30.88%) and is highly statistically significant, p=0.000. As it might be difficult to first estimate percent reduction and then change to improvement, we performed a regression analysis to see if there was, in fact, a relation between the global improvement and the 4 weeks percent reduction in the 3 symptoms.

Figure 16:
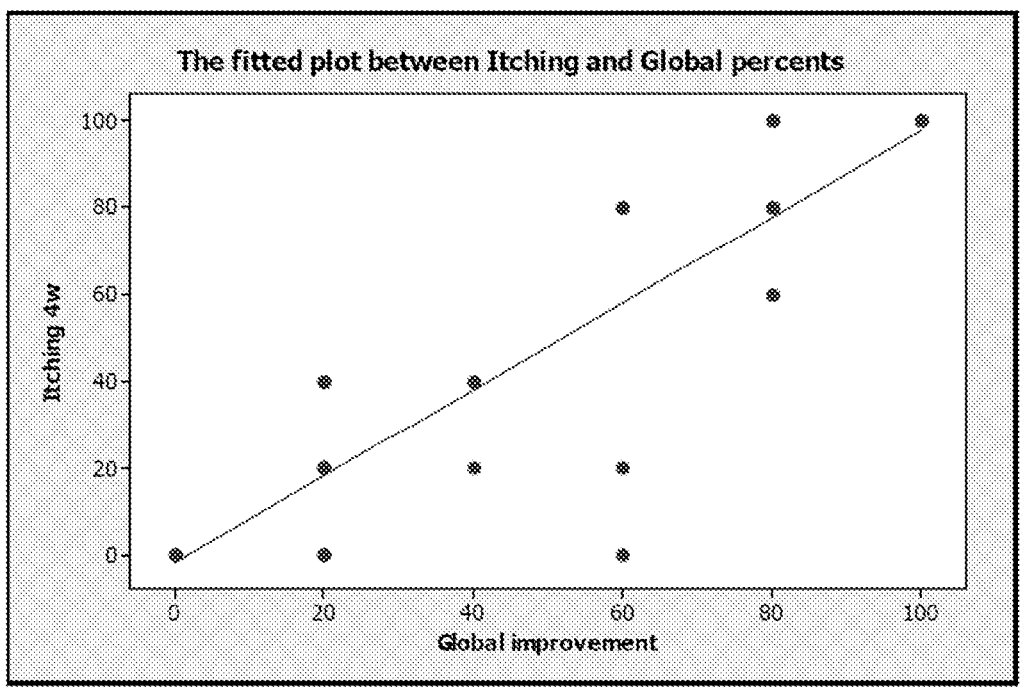
FIG. 16: Line-plot of regression for itching.
Figure 17:
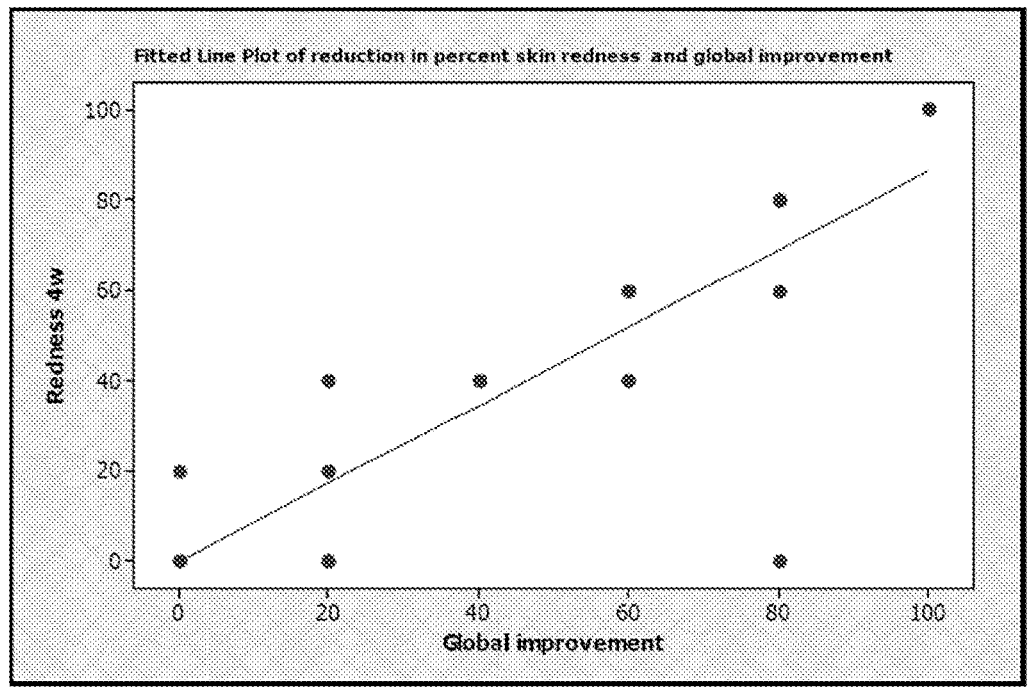
FIG. 17: Line-plot of regression for redness.

FIG. 16 and FIG. 17 can be examples on the correlation between the Global improvement, and the reduction of each symptom. All regressions were statistically significant (p=0.000).

In other words, the Global percent improvement mirror the estimated reduction in the three symptoms asked for.

General Opinion

After 4 weeks (end of treatment) three questions were asked.

Are you satisfied with Ganodex™? 3.4% did not know, 72.4% were satisfied and 21.0% were not satisfied. Three percent did not answer.

Would you like to continue with Ganodex? 45% would like to continue, while 31% would not. 21% did not know and 3% did not answer.

Figure 18:
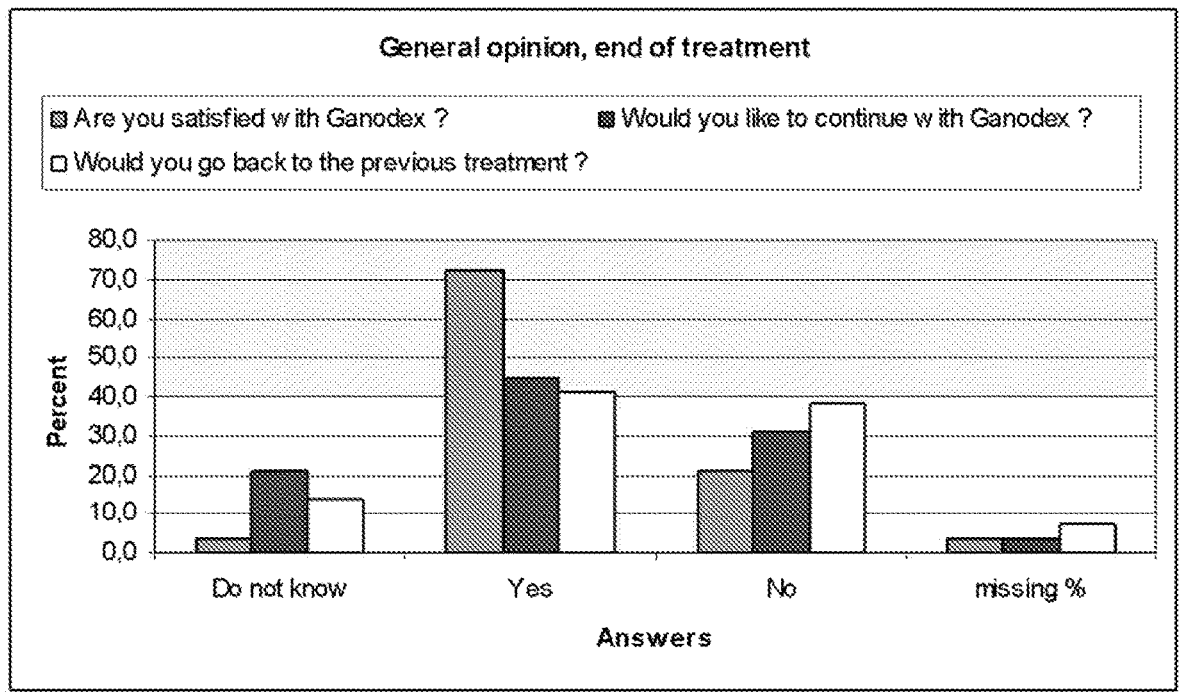
FIG. 18: General opinion at end of survey.

Would you prefer to go back to the previous treatment? 41% would return to their previous treatment, while almost as many 38% would not. 7% did not answer and 14% did not know. Results are shown in FIG. 18.

Unwanted Effects

There was not a specific question about unwanted effects, but some subjects volunteered symptoms in their comment. Symptoms and frequency are given in the table herein below. One subject may report more than one symptom.

| Symptom | number | % |
|---|---|---|
| Thinner skin | 1 | 3.4 |
| Worsening redness | 1 | 3.4 |
| Itching worse | 3 | 10.3 |
| Worsening psoriasis | 1 | 3.4 |
| Burning sensation | 1 | 3.4 |

An unpleasant odour was reported by 7, which was the reason for discontinuing the use of Ganodex™.

Participation

To participate in the survey you should have psoriasis. However, 6 did not state their diagnosis and one had keratosis pilaris, 3 presented with atopic dermatitis, and one with acne. They are all included in the survey.

SUMMARY AND CONCLUSION

Psoriasis can occur at any age, although it most commonly appears for the first time between the ages of 15 and 25 years. The prevalence of psoriasis in Western populations is estimated to be around 2-3%. Psoriasis affects both sexes equally.

In our survey, 69% females and 28% males which indicate a higher response rate in females in this survey. The over-all response rate was 58%. Both the skewed gender distribution and the response rate should be taken into account when generalizing the results.

The subjects were asked to mark one of six possible boxes, with each box containing a given percent reduction (0% to 100%). This might have been difficult for some, resulting in a lower score.

An example can be given, looking at the before and the after treatment in a subject with hand psoriasis.

Figure 19:
FIG. 19: A) Psoriatic hand before treatment with Ganodex™; B) Reduced psoriatic plaque (scaling) after 4 weeks' treatment with Ganodex™.
Figure 19:

A 63 year old male with psoriasis on his hands. Only the right hand is shown as there is little difference from the left hand. The pictures in FIG. 19 are taken by the subject, before (A) and after (B) treatment.

He has marked 40% reduction in scaling and 0% reduction in redness after 4 weeks of treatment. He marked 20% over-all improvement. I think the 20% over-all is far too low, and indicates a possible uncertainty in the understanding of percent change Probably the more correct marking would have been 80% reduction in scaling and 40% reduction in redness, and consequently 60%-80% over-all improvement.

There was no significant difference in distribution of subjects at 4 weeks compared to 2 weeks. The different mean reduction in symptoms is statistically significant for all 3 symptoms comparing 4 weeks with 2 weeks.

Also the mean over-all improvement of the Global question indicated a positive effect of the cream. The mean Global improvement was 44.4%, (±30.88%) and is highly statistically significant, p=0.000. As it might be difficult to first estimate percent reduction and then change to improvement, we performed a regression analysis to see if there in fact was a relation between the global improvement and the 4 weeks percent reduction, in the 3 symptoms. This was found, so the global results are with regard to improvement reflecting the change in mean reduction of symptoms.

The results strongly indicate that application of Ganodex™ cream for 4 weeks has favourable effects in a general psoriatic population. Further, duration of use may be of importance, as 4 weeks' application increased the positive results significantly compared to 2 weeks'.

No serious adverse events were reported, and few adverse symptoms were presented.

The invention claimed is:

1. A method of treating a skin disease selected from psoriasis and eczema in a human subject in need thereof, comprising:
    applying a therapeutically effective amount of a composition comprising isolated extracellular *Ganoderma lucidum* polysaccharides as a bioactive agent to the skin of the human subject for a period of time sufficient to treat the skin disease, wherein the composition is essentially free of *Ganoderma lucidum* mycelium, and wherein the composition is prepared by the process of:
    (i) providing a liquid culture comprising the *Ganoderma lucidum* mycelium;
    (ii) fermenting the liquid culture under conditions sufficient for the *Ganoderma lucidum* mycelium to produce extracellular polysaccharides in an extracellular fraction of a fermented liquid culture;
    (iii) isolating the extracellular fraction from the fermented liquid culture to separate the extracellular *Ganoderma lucidum* polysaccharides from the *Ganoderma lucidum* mycelium;
    (iv) obtaining isolated extracellular *Ganoderma lucidum* polysaccharides essentially free of *Ganoderma lucidum* mycelium; and
    (v) preparing the composition comprising the isolated extracellular *Ganoderma lucidum* polysaccharides.

2. The method of claim 1, wherein the bioactive agent in the composition consists essentially of the extracellular *Ganoderma lucidum* polysaccharides.

3. The method of claim 2, wherein the bioactive agent in the composition consists essentially of extracellular *Ganoderma lucidum* polysaccharides having a molecular weight of from 30 kDa to 1000 kDa.

4. The method of claim 2, wherein the bioactive agent in the composition consists essentially of extracellular *Ganoderma lucidum* polysaccharides having a molecular weight of at least 100 kDa.

5. The method of claim 2, wherein the bioactive agent in the composition consists essentially of extracellular *Ganoderma lucidum* polysaccharides having a molecular weight of at least 1000 kDa.

6. The method of claim 1, wherein the isolated extracellular *Ganoderma lucidum* polysaccharides have a molecular weight of at least 100 kDa.

7. The method of claim 1, wherein the isolated extracellular *Ganoderma lucidum* polysaccharides have a molecular weight of at least 1000 kDa.

8. The method of claim 1, wherein the method for treating the skin disease is a method for ameliorating the skin disease.

9. The method of claim 1, wherein the extracellular polysaccharides are hetero-polysaccharides.

10. The method of claim 9, wherein the hetero-polysaccharides comprise glucose monosaccharide units in combination with further monosaccharide units selected from the group consisting of glucuronic acid, galactose, mannose, arabinose, xylose, and any combination thereof.

11. The method of claim 10, wherein the further monosaccharide units are selected from the group consisting of galactose, mannose, and a combination thereof.

12. The method of claim 1, wherein the isolated fraction consists essentially of extracellular *Ganoderma lucidum* polysaccharides having a molecular weight of from 30 kDa to 1000 kDa.

13. The method of claim 1, wherein the isolated fraction consists essentially of extracellular *Ganoderma lucidum* polysaccharides having a molecular weight of at least 100 kDa.

14. The method of claim 1, wherein the isolated fraction consists essentially of extracellular *Ganoderma lucidum* polysaccharides having a molecular weight of at least 1000 kDa.

15. The method of claim 1, further comprising subjecting the isolated extracellular *Ganoderma lucidum* polysaccharides to at least one further step selected from a purification step and a precipitation step.

16. The method of claim 15, wherein the isolated extracellular *Ganoderma lucidum* polysaccharides are precipitated by ultracentrifugation.

17. The method of claim 16, wherein the isolated extracellular *Ganoderma lucidum* polysaccharides are size fractionated prior to ultracentrifugation.

* * * * *